US012630615B2

(12) United States Patent
Jin et al.

(10) Patent No.: US 12,630,615 B2
(45) Date of Patent: May 19, 2026

(54) NEUTRALIZING ANTI-AMYLOID BETA ANTIBODIES FOR THE TREATMENT OF ALZHEIMER'S DISEASE

(71) Applicants: THE BRIGHAM AND WOMEN'S HOSPITAL, INC., Boston, MA (US); SANOFI, Paris (FR)

(72) Inventors: Ming Jin, Boston, MA (US); Laurent Pradier, Paris (FR); David Reczek, Bridgewater, NJ (US); Dennis Selkoe, Boston, MA (US); Tara Travaline, Bridgewater, NJ (US); Dominic Walsh, Boston, MA (US)

(73) Assignees: THE BRIGHAM AND WOMEN'S HOSPITAL, INC., Boston, MA (US); SANOFI, Paris (FR)

( * ) Notice: Subject to any disclaimer, the term of this patent is extended or adjusted under 35 U.S.C. 154(b) by 1106 days.

(21) Appl. No.: 17/624,309

(22) PCT Filed: Jul. 15, 2020

(86) PCT No.: PCT/US2020/042161
§ 371 (c)(1),
(2) Date: Dec. 31, 2021

(87) PCT Pub. No.: WO2021/011673
PCT Pub. Date: Jan. 21, 2021

(65) Prior Publication Data
US 2023/0107034 A1 Apr. 6, 2023

Related U.S. Application Data

(60) Provisional application No. 62/874,724, filed on Jul. 16, 2019.

(51) Int. Cl.
*C07K 16/18* (2006.01)
*A61P 25/28* (2006.01)

(52) U.S. Cl.
CPC .............. *C07K 16/18* (2013.01); *A61P 25/28* (2018.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 5,731,168 A | 3/1998 | Carter et al. |
| 5,814,014 A | 9/1998 | Elseberry et al. |
| 5,837,821 A | 11/1998 | Wu et al. |
| 5,989,830 A | 11/1999 | Davis et al. |
| 6,093,180 A | 7/2000 | Elseberry et al. |
| 6,193,980 B1 | 2/2001 | Efstathiou et al. |
| 7,612,181 B2 | 11/2009 | Wu et al. |
| 2010/0226923 A1 | 9/2010 | Rao et al. |
| 2017/0209604 A1 | 7/2017 | Krafft et al. |

FOREIGN PATENT DOCUMENTS

| | | |
|---|---|---|
| EP | 1870459 A1 | 12/2007 |
| JP | 2006-508072 A | 3/2006 |
| WO | WO 1993/008829 A1 | 5/1993 |
| WO | WO 1994/009817 A1 | 5/1994 |
| WO | WO 1996/027011 A1 | 9/1996 |
| WO | WO 1998/050431 A2 | 11/1998 |
| WO | WO 2002/002781 A1 | 1/2002 |
| WO | WO 2003/104437 A2 | 12/2003 |
| WO | WO 2004/031400 A2 | 4/2004 |
| WO | WO 2005/018572 A2 | 3/2005 |
| WO | WO 2008/150949 A1 | 12/2008 |
| WO | WO 2008/156622 A1 | 12/2008 |
| WO | WO 2009/089004 A1 | 7/2009 |
| WO | WO 2011/133919 A1 | 10/2011 |
| WO | WO 2012/009442 A2 | 1/2012 |

OTHER PUBLICATIONS

Stern et al., Brain 2022: 145; 2528-2540 (Year: 2022).*
The advertisement from Trianni, Inc., published Sep. 2016, available at biopharmadealmakers.nature.com (Year: 2016).*
Hong et al., Acta Neuropathologica (2018) 136:19-40 (Year: 2018).*
Wang et al., Acta Neuropathologica Communications (2023) 11:39 (Year: 2023).*
Ashkenazi et al., "Immunoadhesins: An Alternative to Human Monoclonal Antibodies", Methods, Oct. 1995, 8(2): 104-115.
Atwell et al., "Stable heterodimers from remodeling the domain interface of a homodimer using a phage display library", J. Mol. Biol., Jul. 4, 1997, 270(1): 26-35.
Brennan et al., "Preparation of bispecific antibodies by chemical recombination of monoclonal immunoglobulin G1 fragments", Science, Jul. 5, 1985, 229(4708): 81-83.
Chen et al., "Amyloid beta: structure, biology and structure-based therapeutic development", Acta Pharmacologica Sinica, Jul. 10, 2017, 38(9): 1205-1235.
Ebersbach et al., "Affilin-novel binding molecules based on human gamma-B-crystallin, an all beta-sheet protein", J. Mol. Biol., Sep. 7, 2007, 372(1): 172-185.

(Continued)

*Primary Examiner* — Christina M Borgeest
(74) *Attorney, Agent, or Firm* — LATHROP GPM LLP; James H. Velema, Esq.; Judith L. Stone-Hulslander, Esq.

(57) ABSTRACT

Binding polypeptides (e.g., antibodies and antigen-binding fragments thereof) that specifically bind one or more species of soluble, AD brain-derived synaptotoxic amyloid beta (Aβ) without binding to classical monomeric, protofibrillar or fibrillar Aβ, are provided. Pharmaceutical compositions comprising binding polypeptides that specifically bind one or more species of soluble, synaptotoxic Aβ are provided. Methods of making binding polypeptides that specifically bind one or more species of soluble, synaptotoxic Aβ are provided. Methods of treating Alzheimer's disease using binding polypeptides that specifically bind one or more species of soluble, synaptotoxic Aβ are provided. Methods of reducing one or more symptoms of Alzheimer's disease using binding polypeptides that specifically bind one or more species of soluble, synaptotoxic Aβ are provided.

17 Claims, 69 Drawing Sheets

Specification includes a Sequence Listing.

(56) References Cited

OTHER PUBLICATIONS

Glenner, "Reprint of Alzheimer's disease: Initial report of the purification and characterization of a novel cerebrovascular amyloid protein", Biochem. Biophys. Res. Commun., May 16, 2012, 425(3): 534-539.

Golde, "Open questions for Alzheimer's disease immunotherapy", Alzheimer's Res. Ther., Jan. 7, 2014, 6(1): 3.

Goldsbury et al., "Studies on the in vitro assembly of a beta 1-40: implications for the search for a beta fibril formation inhibitors", J. Struct. Biol., Jun. 2000, 130(2-3): 217-231.

Grabulovski et al., "A novel, non-immunogenic Fyn SH3-derived binding protein with tumor vascular targeting properties", J. Biol. Chem., Feb. 2, 2007, 282(5): 3196-3204. Epub Nov. 27, 2006.

Gruber et al., "Efficient tumor cell lysis mediated by a bispecific single chain antibody expressed in *Escherichia coli*", J. Immunol., Jun. 1, 1994, 152(11): 5368-5374.

Haass et al., "Cellular processing of beta-amyloid precursor protein and the genesis of amyloid beta-peptide", Cell, Dec. 17, 1993, 75(6): 1039-1042.

Hefti et al., "The case for soluble Aβ oligomers as a drug target in Alzheimer's disease", Trends in Pharmacological Sciences, May 1, 2013, 34(5): 261-265. Epub Apr. 10, 2013.

Holliger et al., ""Diabodies": small bivalent and bispecific antibody fragments.", PNAS USA, Jul. 15, 1993, 90(14): 6444-6448.

International Search Report and Written Opinion for PCT International Patent Application No. PCT/US2020/042161, mailed May 11, 2021.

Isaacs, "Immunoadhesins for immunomodulation of autoimmune and rheumatic disease.", Brit. J. Rheum., Mar. 1, 1997, 36(3): 305-307.

Jin et al., "An invitro paradigm to assess potential anti-Aβ antibodies for Alzheimer's disease", Nature Communications, Jul. 11, 2018, 9(1): 2676.

Jones, "Proteinase mutants of *Saccharomyces cerevisiae*", Genetics, Jan. 1977, 85(1): 23-33.

Kayed et al., "Common Structure of soluble amyloid oligomers implies common mechanism of pathogenesis", Science, Apr. 18, 2003, 300(5618): 486-489.

Kingsman et al., "Replication in Saccharomyces cerevisiae of plasmid pBR313 carrying DNA from the yeast trpl region", Gene, Oct. 1979, 7(2): 141-152.

Kohyama et al., "Alzheimer's disease and immunotherapy: what is wrong with clinical trials?", Immunotargets Ther., Jan. 8, 2015, 4: 27-34.

Koide et al., "Monobodies: antibody mimics based on the scaffold of the fibronectin type III domain", Methods Mol. Biol., 2007, 352: 95-109.

Kostelny et al., "Formation of a bispecific antibody by the use of leucine zippers", J. Immunol., Mar. 1, 1992, 148(5): 1547-1553.

Krehenbrink et al., J. Mol. Biol., "Artificial binding proteins (Affitins) as probes for conformational changes in secretin PulD", Nov. 28, 2008, 383(5): 1058-1068. Epub Sep. 16, 2008.

Lambert et al., "Monoclonal antibodies that target pathological assemblies of A beta", Journal of Neurochemistry, Jan. 2007, 100(1): 23-35. Epub Nov. 20, 2006.

Lambert et al., "Vaccination with soluble Aβ oligomers generates toxicity-neutralizing antibodies", Journal of Neurochemistry, Nov. 2001, 79(3): 595-605.

Lashuel et al., "Mixtures of wild-type and a pathogenic (E22G) form of Abeta40 in vitro accumulate protofibrils, including amyloid pores", J. Mol. Biol., Sep. 26, 2003, 332(4): 795-808.

Lefranc et al., "IMGT unique numbering for immunoglobulin and T cell receptor variable domains and Ig superfamily V-like domains", Dev. Comp. Immunol., Jan. 2003, 27)1: 55-77.

Li et al., "Decoding the synaptic dysfunction of bioactive human AD brain soluble Aβ to inspire novel therapeutic avenues for Alzheimer's disease", Acta Neuropathol. Commun., Nov. 8, 2018, 6(1): 121.

Li et al., "Soluble Aβ Oligomers Inhibit Long-Term Potentiation through a Mechanism Involving Excessive Activation of Extrasynaptic NR2B-Containing NMDA Receptors", J. Neurosci., May 4, 2011, 31(18): 6627-6638.

Liu et al., "A cellular complex of BACE1 and γ-secretase sequentially generates Aβ from its full-length precursor", J. Cell Biol., Feb. 4, 2019, 218(2): 644-663. Epub Jan. 9, 2019.

Liu et al., "Antibody-Based Drugs and Approaches Against Amyloid-β Species for Alzheimer's Disease Immunotherapy", Drugs Aging, Oct. 2016, 33(10): 685-697.

Liu et al., "Differential roles of ERK, JNK and p38 MAPK in pain-related spatial and temporal enhancement of synaptic responses in the hippocampal formation of rats: multi-electrode array recordings", Brain Res., Mar. 25, 2011, 1382: 57-69. Epub Jan. 31, 2011.

Merchant et al., "An efficient route to human bispecific IgG", Nature Biotech., Jul. 1998, 16(7): 677-681.

Milstein et al., "Hybrid hybridomas and their use in immunohistochemistry", Nature, Oct. 1983, Nature, 305(5934): 537-540.

Nichols et al., "Growth of beta-amyloid(1-40) protofibrils by monomer elongation and lateral association. Characterization of distinct products by light scattering and atomic force microscopy", Biochemistry, May 14, 2002, 41(19): 6115-6127.

Nixon et al., "Engineered protein inhibitors of proteases", Curr. Opin. Drug Discov. Devel., May 2006, 9(2): 261-268.

Ridgway et al., "Knobs-into-holes' engineering of antibody CH3 domains for heavy chain heterodimerization", Protein Eng., Jul. 1996, 9(7): 617-621.

Roux et al., "Comparisons of the ability of human IgG3 hinge mutants, IgM, IgE, and IgA2, to form small immune complexes: a role for flexibility and geometry", J. Immunol., Oct. 15, 1998, 161(8): 4083-4090.

Ryan et al., "An Improved Method for Generating Consistent Soluble Amyloid-beta Oligomer Preparations for In Vitro Neurotoxicity Studies", J. Neurosci. Methods, Jul. 15, 2010, 190(2): 171-179. Epub May 7, 2010.

Selkoe et al., "The amyloid hypothesis of Alzheimer's disease at 25 years", EMBO Mol Med, Jun. 1, 2016, 8(6): 595-608.

Shankar et al., "Amyloid β-Protein Dimers Isolated Directly from Alzheimer Brains Impair Synaptic Plasticity and Memory", Nat. Med., Jun. 22, 2008, 14(8): 837-842.

Shughrue et al., "Anti-ADDL antibodies differentially block oligomer binding to hippocampal neurons", Neurobiology of Aging, Feb. 2010, 31(2): 189-202.

Silverman et al., "Multivalent avimer proteins evolved by exon shuffling of a family of human receptor domains", Nat. Biotechnol., Dec. 2005, 23(12): 1556-1561.

Skerra et al., "Alternative binding proteins: anticalins—harnessing the structural plasticity of the lipocalin ligand pocket to engineer novel binding activities", FEBS J., Jun. 2008, 275(11): 2677-2683.

Soreghan et al., "Surfactant properties of Alzheimer's A beta peptides and the mechanism of amyloid aggregation", J. Biol. Chem., Nov. 18, 1994, 269(46): 28551-28554.

Stumpp et al., "DARPins: a new generation of protein therapeutics", Drug Discov. Today, Aug. 2008, 13(15-16): 695-701. Epub Jul. 11, 2008.

Tomic et al., "Soluble Fibrillar Oligomer Levels are Elevated in Alzheimer's Disease Brian and Correlate with Cognitive Dysfunction", Neurobiol Dis, Sep. 2009, 35(3): 352-358. Epub Jun. 10, 2009.

Traunecker et al., "Bispecific single chain molecules (Janusins) target cytotoxic lymphocytes on HIV infected cells", EMBO J., Dec. 1991, 10(12): 3655-3659.

Tutt et al., "Trispecific F(ab')3 derivatives that use cooperative signaling via the TCR/CD3 complex and CD2 to activate and redirect resting cytotoxic T cells", J. Immunol., Jul. 1, 1991, 147(1): 60-69.

Van Dyck, "Anti-Amyloid-β Monoclonal Antibodies for Alzheimer's Disease: Pitfalls and Promise", Biol. Psychiatry, Feb. 15, 2018, 83(4): 311-319. Epub Aug. 24, 2017.

Walsh et al., "Amyloid beta-protein fibrillogenesis. Detection of a protofibrillar intermediate", J. Biol. Chem., Aug. 29, 1997, 272(35): 22364-22372.

(56) References Cited

OTHER PUBLICATIONS

Ying et al., "Preparation and characterization of a monoclonal antibody with affinity for soluble Aβ oligomers", Hybridoma, Oct. 2009, 28(5): 349-454.

Zago et al., "Neutralization of Soluble, Synaptotoxic Amyloid β Species by Antibodies Is Epitope Specific", J. Neurosci, Feb. 22, 2012, 328(8): 2696-2702.

* cited by examiner

ELISA: Pre-Fusion Bleed Sera Titers
Fusions A, B, and C
Coat: ADDLS @ 1ug/ml

PFB-A
PFB-B
PFB-C

*Fig. 1*

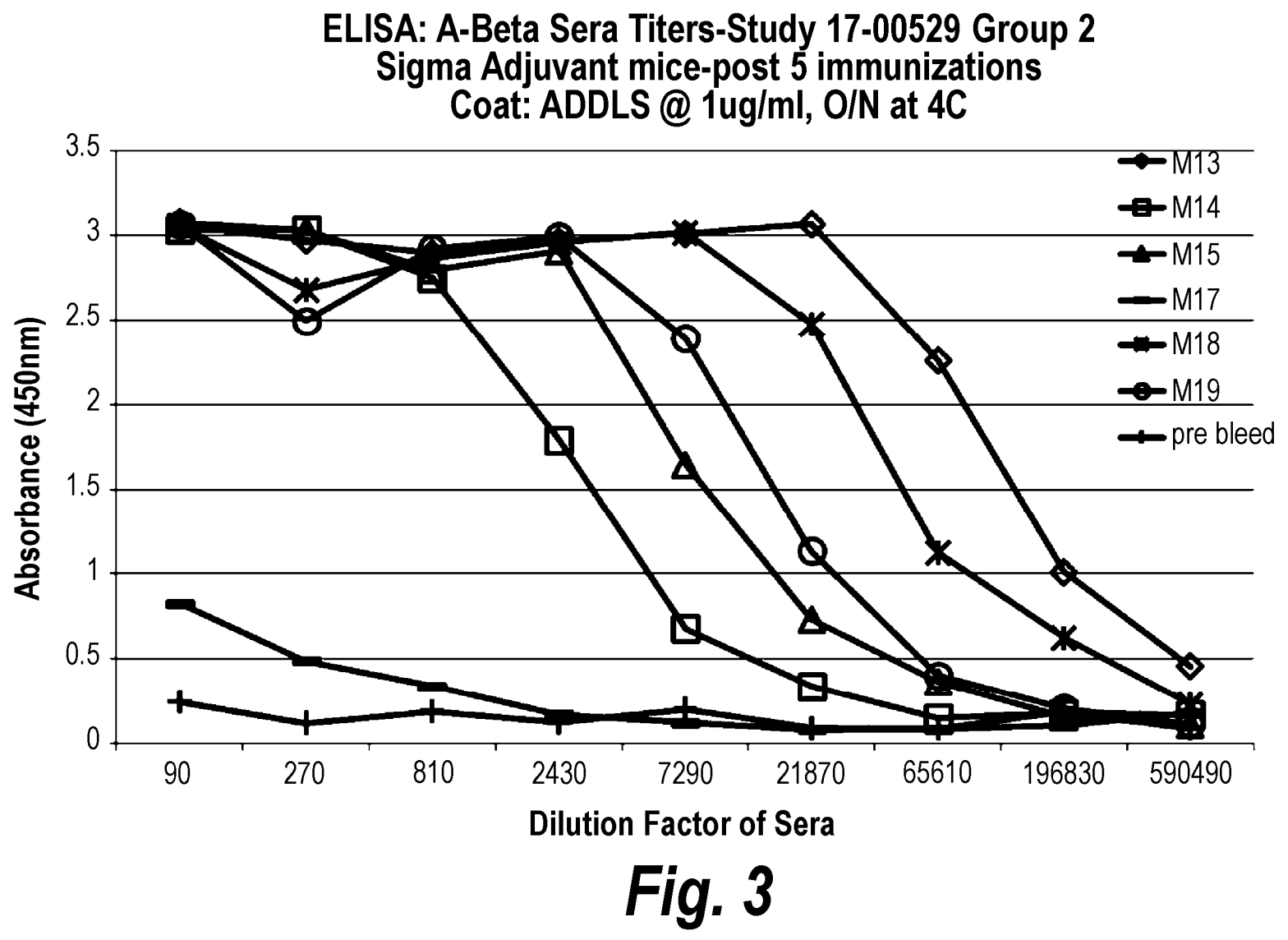

ELISA: A-Beta Sera Titers-Study 17-00529 Group 2
Sigma Adjuvant mice-post 5 immunizations
Coat: ADDLS @ 1ug/ml, O/N at 4C M13
M14
M15
M17
M18
M19
pre bleed Absorbance (450nm)

Dilution Factor of Sera

*Fig. 3*

| Clone | ELISA (supes) ADDLs (1ug/mL) | PFs (1ug/mL) | SDS-PAGE | aSEC | ELISA titration (Ab) on PFs | Isotype | SPR offrate (mono) | Octet kinetics | SPR kinetics | Abeta Fibrils | asyn fibrils (in house) | asyn fibrils (comm) | SOD1 | iN Assay | VH/VL Seq | Recomb |
|---|---|---|---|---|---|---|---|---|---|---|---|---|---|---|---|---|
| B24 | 2.984 | 1.724 | | | low affinity | IgG2b, k | no | done | done | low | no | no | low | rescue | Y | pending |
| B28 | 3.06 | 3.119 | | | low affinity | IgG2b, k | no | done | done | low | no | no | low | rescue | Y | pending |
| B51 | 3.097 | 3.192 | | | med affinity | IgG2b, k | low | done | done | high | low | low | low-med low | rescue | Y | pending |
| B54 | 3.097 | 3.162 | | | high affinity | IgG2b, k | low | done | done | med-hi | no | very low | low | rescue | Y | pending |
| B73 | 2.925 | 3.166 | | | med affinity | IgG1, λ | no | done | done | med | no | no | low | rescue | Y | pending |
| B90 | 3.132 | 3.144 | | | high affinity | IgG2b, k | low | done | done | med-hi | no | very low | low | rescue | Y | pending |

*Fig. 4*

Fig. 5
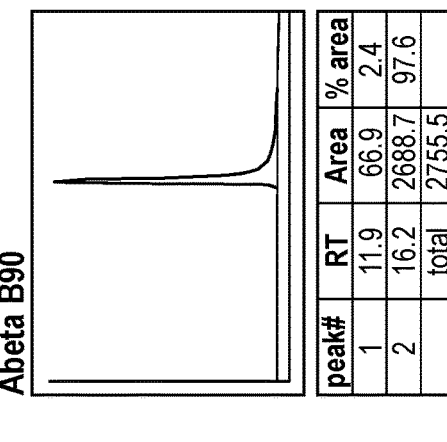
Abeta B90
| peak# | RT | Area | % area |
|---|---|---|---|
| 1 | 11.9 | 66.9 | 2.4 |
| 2 | 16.2 | 2688.7 | 97.6 |
| | total | 2755.5 | |
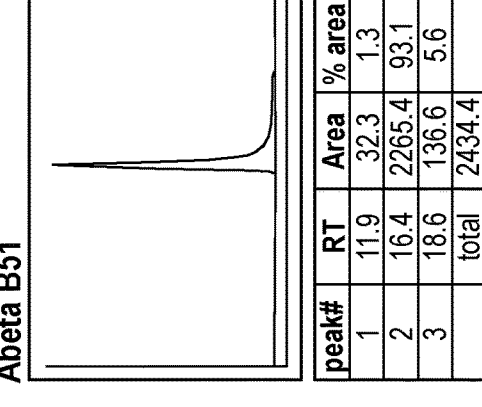
Abeta B28
| peak# | RT | Area | % area |
|---|---|---|---|
| 1 | 11.9 | 89.7 | 1.8 |
| 2 | 16.2 | 4917.4 | 98.2 |
| | total | 5007.1 | |
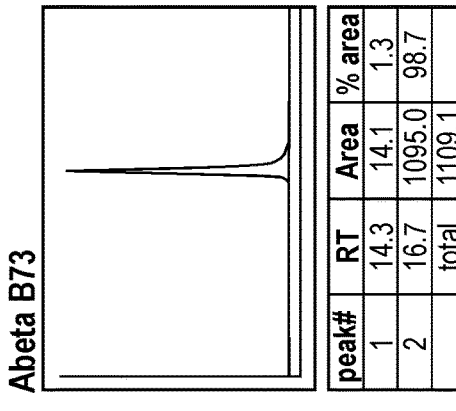
Abeta B60
| peak# | RT | Area | % area |
|---|---|---|---|
| 1 | 11.9 | 15.0 | 1.0 |
| 2 | 16.1 | 1342.2 | 90.6 |
| 3 | 17.8 | 123.6 | 8.3 |
| | total | 1480.8 | |
Abeta B51
| peak# | RT | Area | % area |
|---|---|---|---|
| 1 | 11.9 | 32.3 | 1.3 |
| 2 | 16.4 | 2265.4 | 93.1 |
| 3 | 18.6 | 136.6 | 5.6 |
| | total | 2434.4 | |
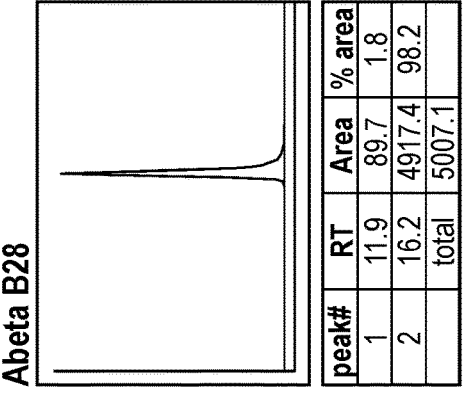
Abeta B73
| peak# | RT | Area | % area |
|---|---|---|---|
| 1 | 14.3 | 14.1 | 1.3 |
| 2 | 16.7 | 1095.0 | 98.7 |
| | total | 1109.1 | |
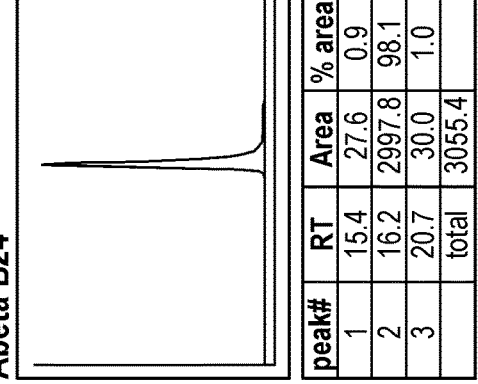
Abeta B24
| peak# | RT | Area | % area |
|---|---|---|---|
| 1 | 15.4 | 27.6 | 0.9 |
| 2 | 16.2 | 2997.8 | 98.1 |
| 3 | 20.7 | 30.0 | 1.0 |
| | total | 3055.4 | |
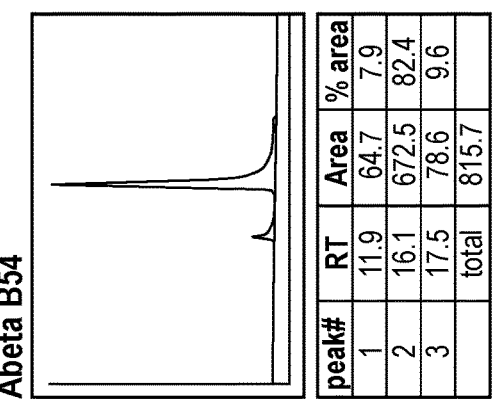
Abeta B54
| peak# | RT | Area | % area |
|---|---|---|---|
| 1 | 11.9 | 64.7 | 7.9 |
| 2 | 16.1 | 672.5 | 82.4 |
| 3 | 17.5 | 78.6 | 9.6 |
| | total | 815.7 | |

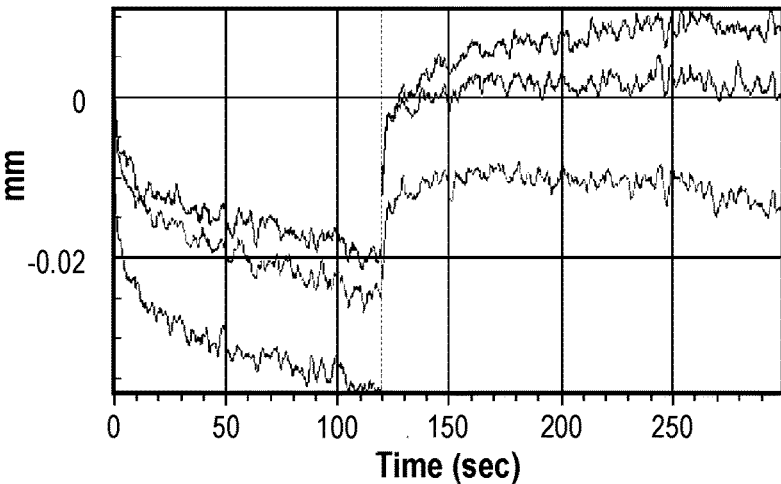
Loading Sample ID: B24; Sample ID: Ab1-40
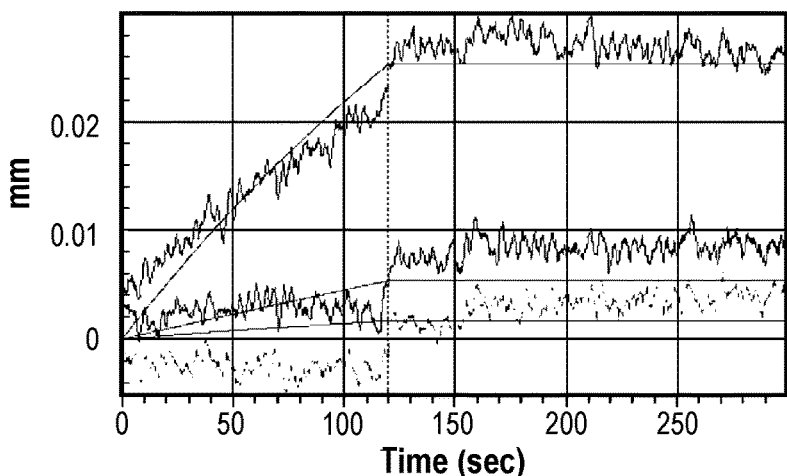
Loading Sample ID: B24; Sample ID: PF
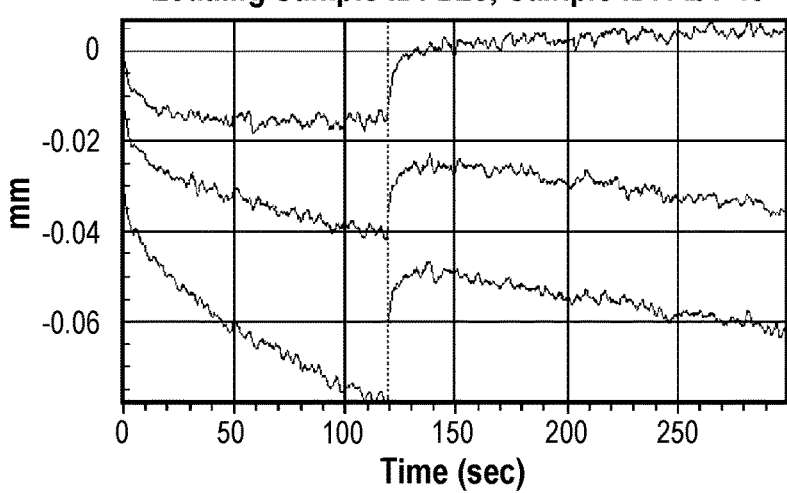
Loading Sample ID: B28; Sample ID: Ab1-40
*Fig. 8*

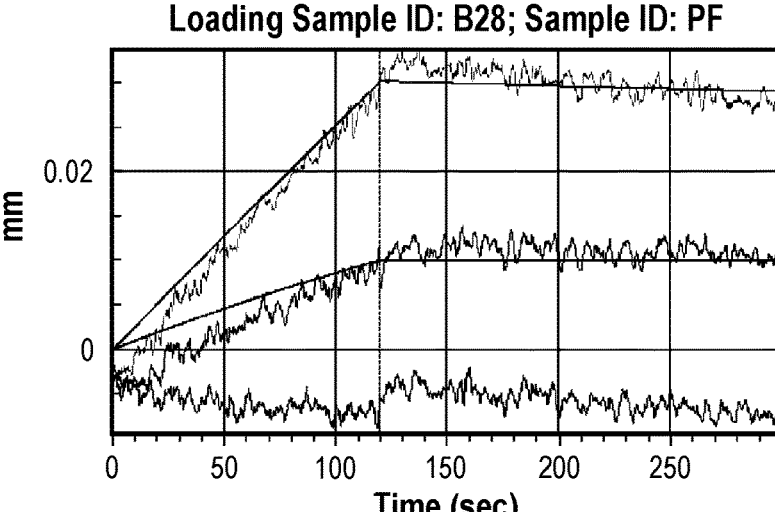
Loading Sample ID: B28; Sample ID: PF
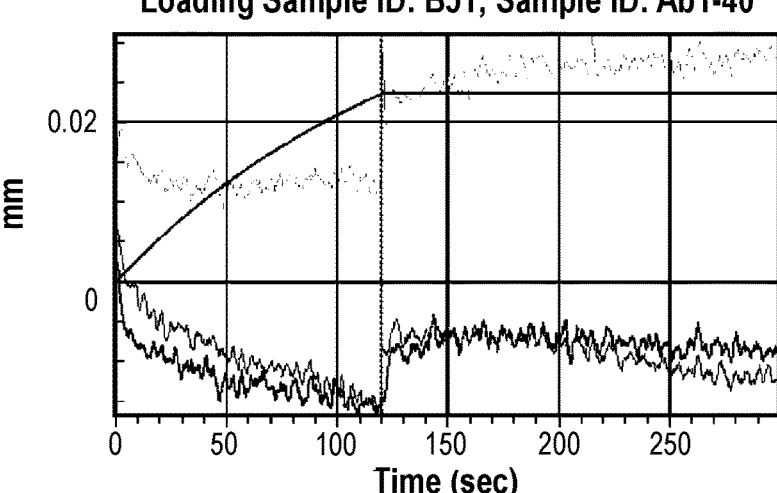
Loading Sample ID: B51; Sample ID: Ab1-40
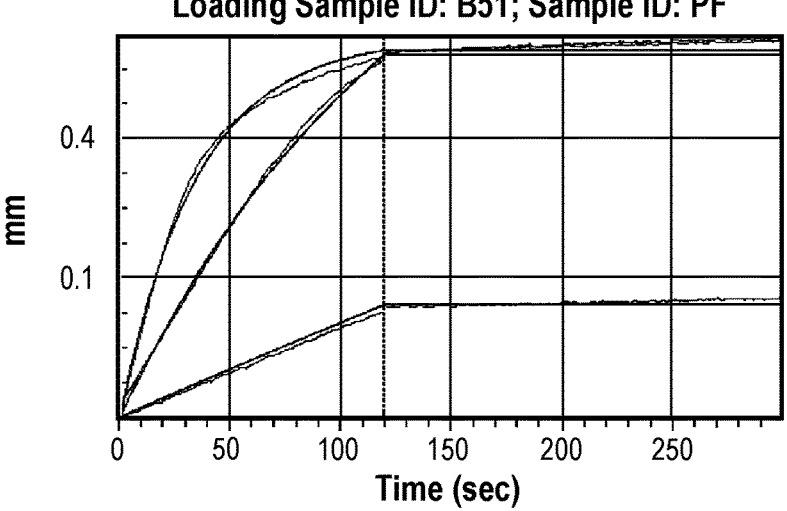
Loading Sample ID: B51; Sample ID: PF
*Fig. 8 (continued)*

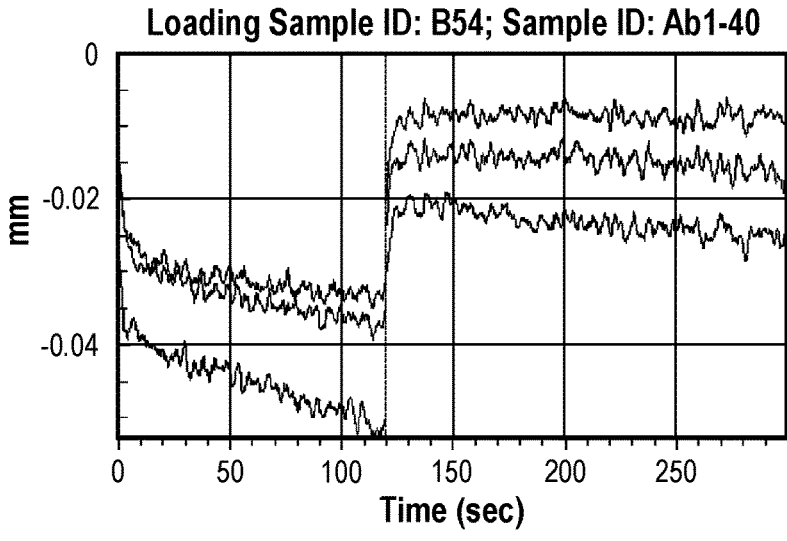
Loading Sample ID: B54; Sample ID: Ab1-40
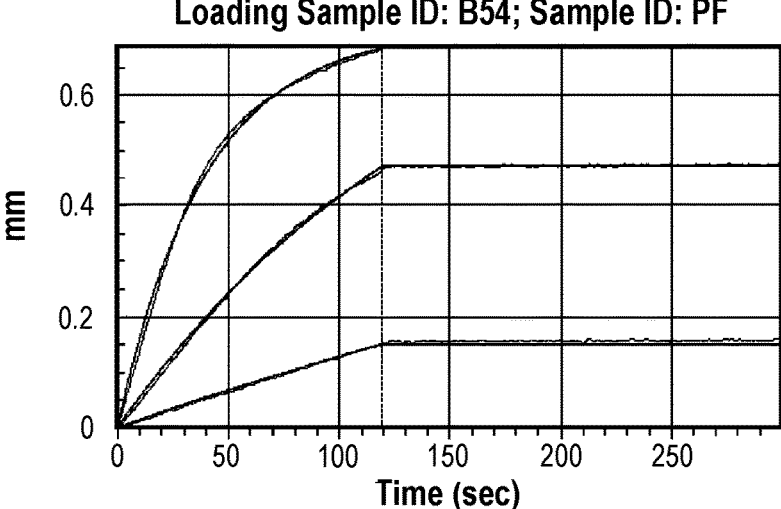
Loading Sample ID: B54; Sample ID: PF
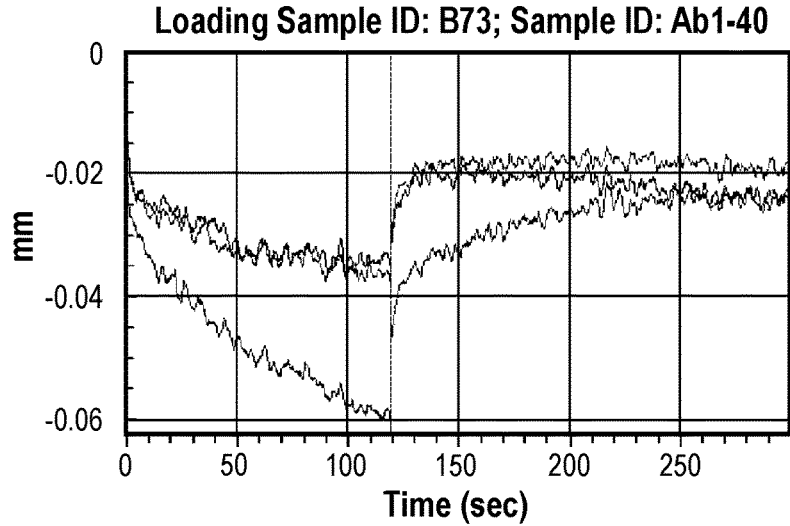
Loading Sample ID: B73; Sample ID: Ab1-40
*Fig. 8 (continued)*

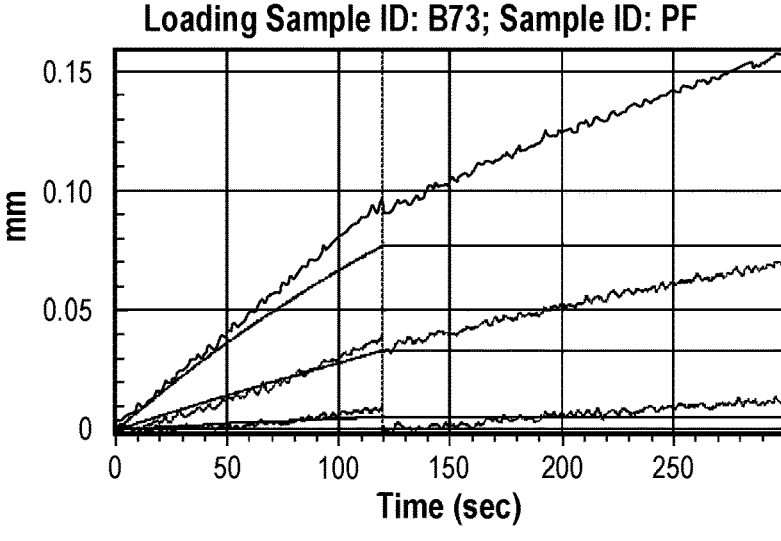
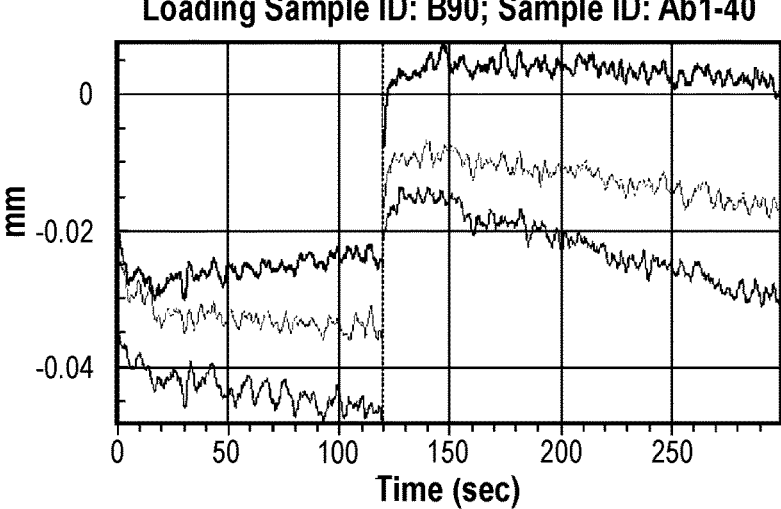
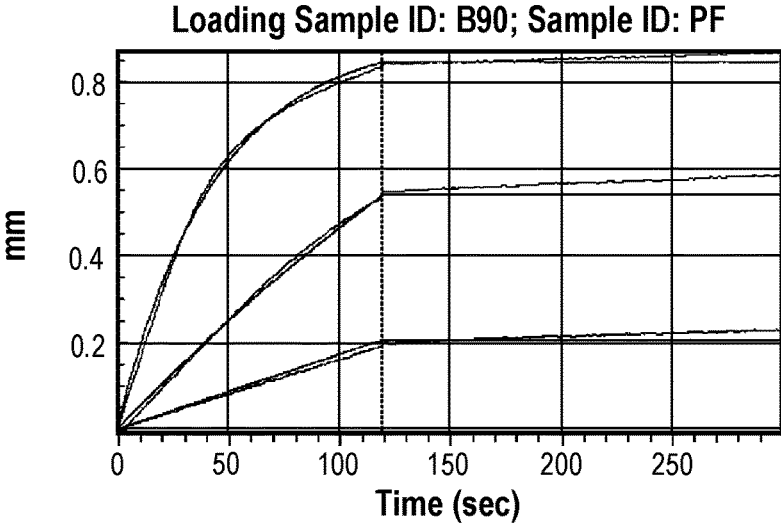
*Fig. 8 (continued)*

| Sensor Type | Loading Sample ID | Sample ID | Conc. (nM) | Response | KD (M) | kon (1/Ms) | kdis (1/s) | RMax |
|---|---|---|---|---|---|---|---|---|
| Protein G | B24 | Ab1-40 | 62.2 | NB | NB | NB | NB | 0 |
| Protein G | B24 | Ab1-40 | 250 | NB | NB | NB | NB | 0 |
| Protein G | B24 | Ab1-40 | 1000 | NB | NB | NB | NB | 0 |
| Protein G | B24 | PF | 0.9167 | LB | <1.0E-12 | 3.04E+06 | <1.0E-07 | 0.006 |
| Protein G | B24 | PF | 3.67 | LB | <1.0E-12 | 1.95E+05 | <1.0E-07 | 0.0654 |
| Protein G | B24 | PF | 14.7 | LB | <1.0E-12 | 2.53E+05 | <1.0E-07 | 0.0704 |
| Protein G | B28 | Ab1-40 | 62.2 | NB | NB | NB | NB | 0 |
| Protein G | B28 | Ab1-40 | 250 | NB | NB | NB | NB | 0 |
| Protein G | B28 | Ab1-40 | 1000 | NB | NB | NB | NB | 0 |
| Protein G | B28 | PF | 0.9167 | + | 2.16E+17 | 8.52E+04 | 1.84E+22 | 0.0197 |
| Protein G | B28 | PF | 3.67 | + | <1.0E-12 | 7.78E+05 | <1.0E-07 | 0.0344 |
| Protein G | B28 | PF | 14.7 | + | 2.18E-08 | 9.78E+03 | 2.14E-04 | 1.7868 |
| Protein G | B51 | Ab1-40 | 62.2 | NB | NB | NB | NB | 0 |
| Protein G | B51 | Ab1-40 | 250 | NB | NB | NB | NB | 0.0168 |
| Protein G | B51 | Ab1-40 | 1000 | NB | NB | NB | NB | 0.0407 |
| Protein G | B51 | PF | 0.9167 | ++ | <1.0E-12 | 6.76E+05 | <1.0E-07 | 2.2581 |
| Protein G | B51 | PF | 3.67 | ++ | <1.0E-12 | 2.07E+06 | <1.0E-07 | 0.8704 |
| Protein G | B51 | PF | 14.7 | ++ | <1.0E-12 | 1.95E+06 | <1.0E-07 | 0.544 |
| Protein G | B54 | Ab1-40 | 62.2 | NB | NB | NB | NB | 0 |
| Protein G | B54 | Ab1-40 | 250 | NB | NB | NB | NB | 0 |
| Protein G | B54 | Ab1-40 | 1000 | NB | NB | NB | NB | 0 |
| Protein G | B54 | PF | 0.9167 | ++ | <1.0E-12 | 2.07E+06 | <1.0E-07 | 0.7425 |
| Protein G | B54 | PF | 3.67 | ++ | <1.0E-12 | 1.74E+06 | <1.0E-07 | 0.8828 |
| Protein G | B54 | PF | 14.7 | ++ | <1.0E-12 | 1.71E+06 | <1.0E-07 | 0.7202 |
| Protein G | B73 | Ab1-40 | 62.2 | NB | NB | NB | NB | 0 |
| Protein G | B73 | Ab1-40 | 250 | NB | NB | NB | NB | 0 |
| Protein G | B73 | Ab1-40 | 1000 | NB | NB | NB | NB | 0 |
| Protein G | B73 | PF | 0.9167 | + | <1.0E-12 | 5.73E+06 | <1.0E-07 | 0.0116 |
| Protein G | B73 | PF | 3.67 | + | <1.0E-12 | 3.15E+05 | <1.0E-07 | 0.2575 |
| Protein G | B73 | PF | 14.7 | + | <1.0E-12 | 2.68E+05 | <1.0E-07 | 0.2052 |
| Protein G | B90 | Ab1-40 | 62.2 | NB | NB | NB | NB | 0 |
| Protein G | B90 | Ab1-40 | 250 | NB | NB | NB | NB | 0 |
| Protein G | B90 | Ab1-40 | 1000 | NB | NB | NB | NB | 0 |
| Protein G | B90 | PF | 0.9167 | ++ | <1.0E-12 | 1.71E+05 | <1.0E-07 | 11.1467 |
| Protein G | B90 | PF | 3.67 | ++ | <1.0E-12 | 8.06E+05 | <1.0E-07 | 1.809 |
| Protein G | B90 | PF | 14.7 | ++ | <1.0E-12 | 1.54E+06 | <1.0E-07 | 0.9073 |

*Fig. 9*

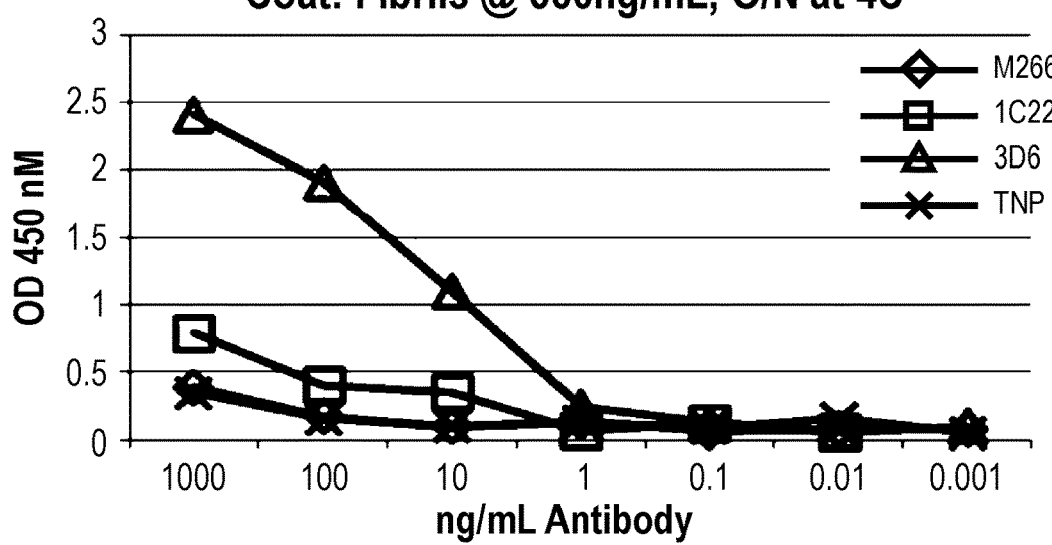
ELISA: Positive and Negative Controls
3D6, 1C22, M266 and TNP
Coat: Fibrils @ 500ng/mL, O/N at 4C
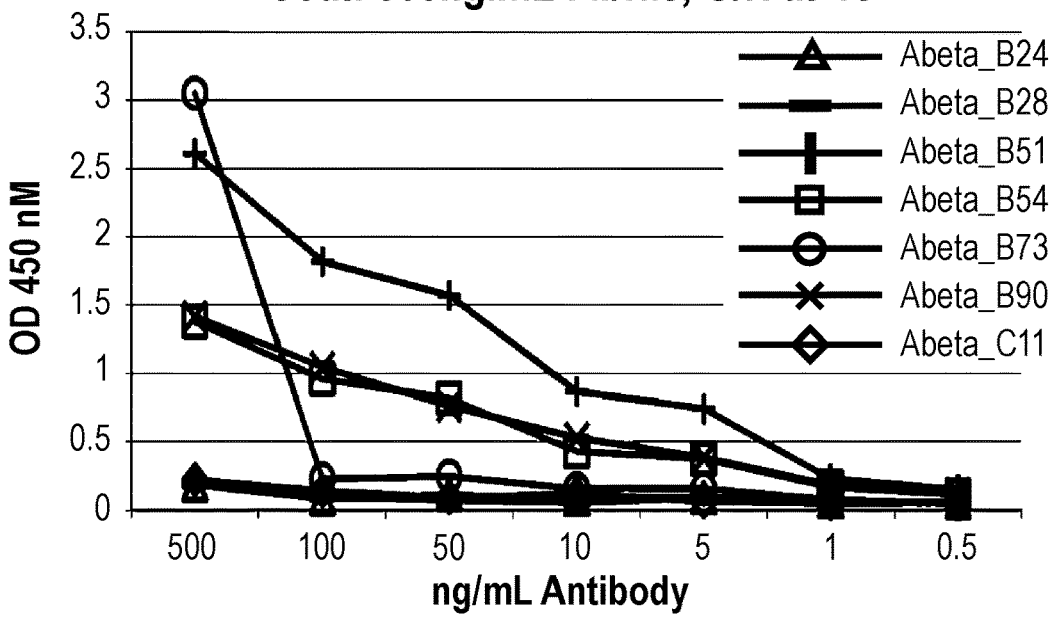
Indirect ELISA :
Abeta Clones- Titration against Fibrils
Coat: 500ng.mL Fibrils, O/N at 4C
*Fig. 10*

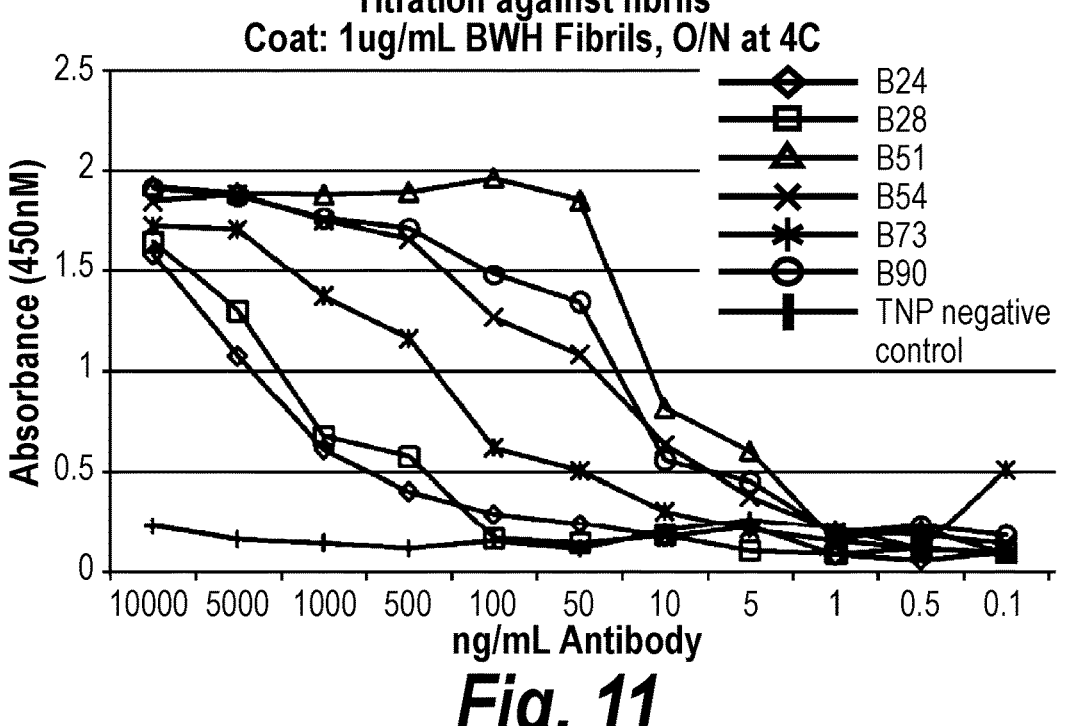
Indirect ELISA:
Abeta Purified Fusion B Clones
Titration against fibrils
Coat: 1ug/mL BWH Fibrils, O/N at 4C
*Fig. 11*
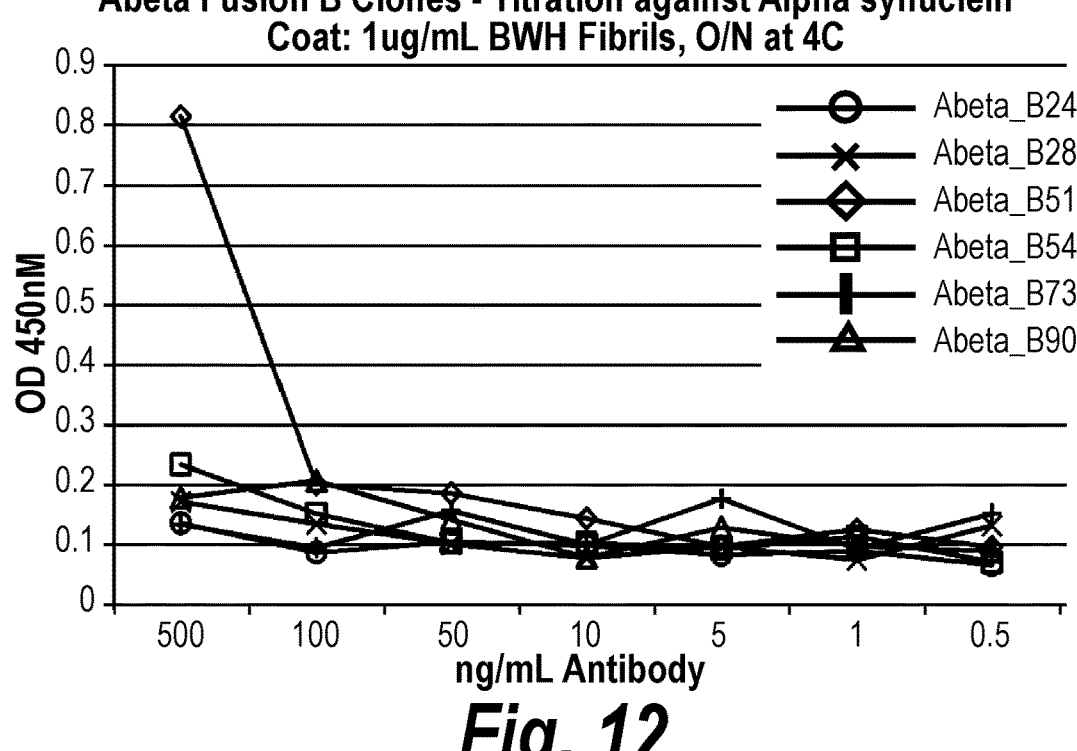
Indirect ELISA:
Abeta Fusion B Clones - Titration against Alpha synuclein
Coat: 1ug/mL BWH Fibrils, O/N at 4C
*Fig. 12*

Abeta Purified Fusion B Clones
Counterscreen against aggregated alpha synuclein
Coat: 1ug/mL human alpha synuclein filaments (Proteos), O/N at 4C

Indirect ELISA:
Abeta Purified Fusion B and C Clones
Counterscreen against aggregated alpha synuclein
Coat: 1ug/mL human alpha synuclein filaments (Proteos), O/N at 4C

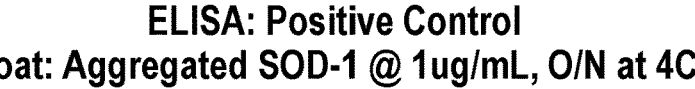
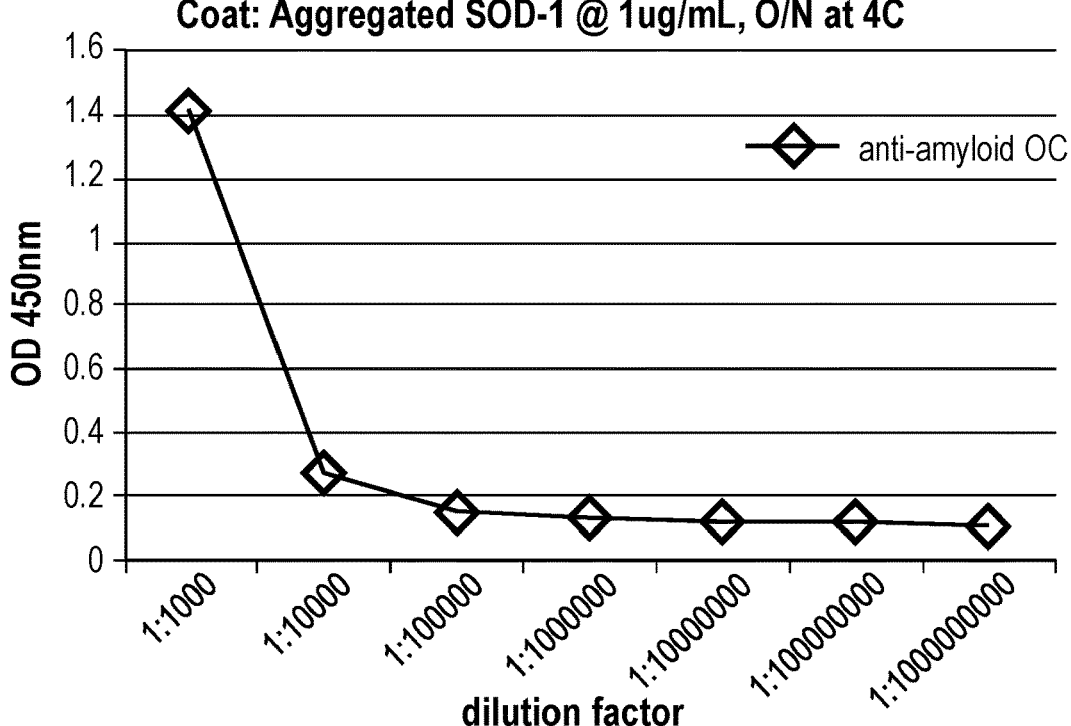
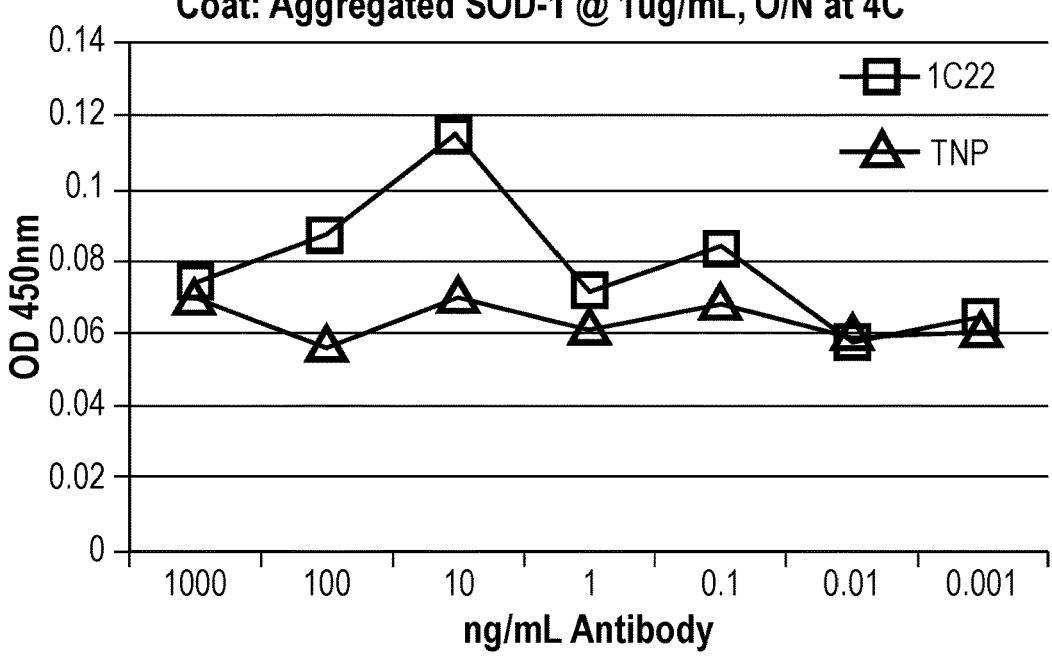
Fig. 15

Indirect ELISA:
Abeta Lead B and C Clones - Titration against Aggregated SOD-1
Coat: 1ug/mL aggregated SOD-1, O/N at 4C Abeta_B24
Abeta_B28
Abeta_B51
Abeta_B54
Abeta_B73
Abeta_B90
Abeta_C11

OD 450nM ng/mL Antibody

ELISA: Positive Control for Counterscreen ELISA
anti-amyloid OC rabbit polyclonal
Coat: aggregated SOD-1 @ 1ug/mL, O/N at 4C
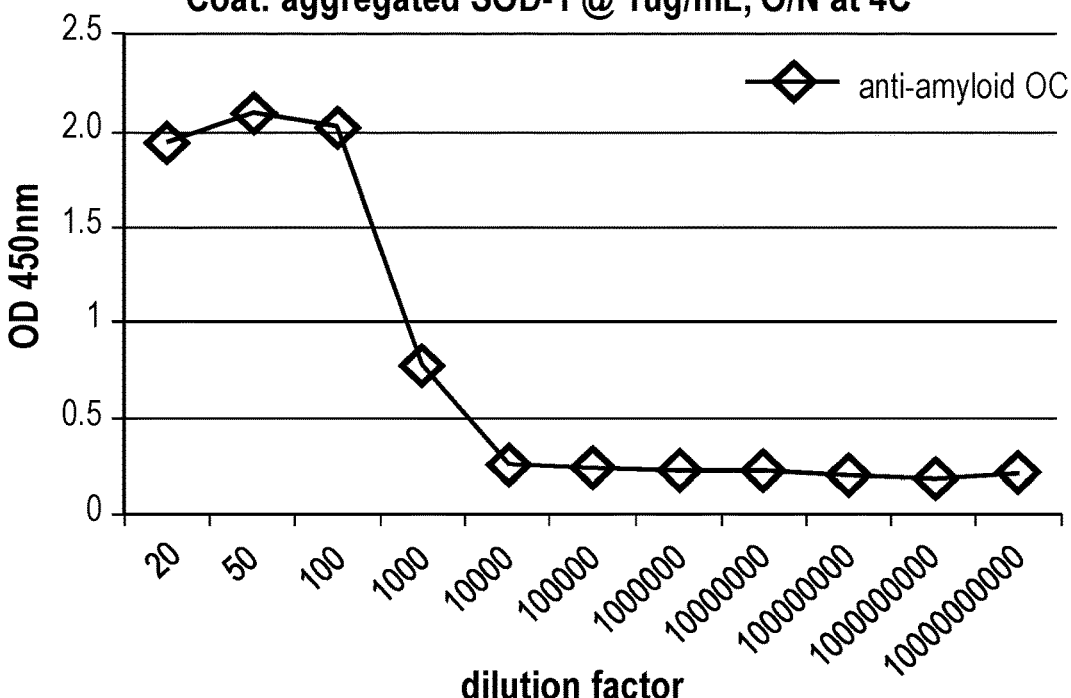
ELISA: Negative Control for Counterscreen ELISA
anti-amyloid OC rabbit polyclonal
Coat: aggregated SOD-1 @ 1ug/mL, O/N at 4C
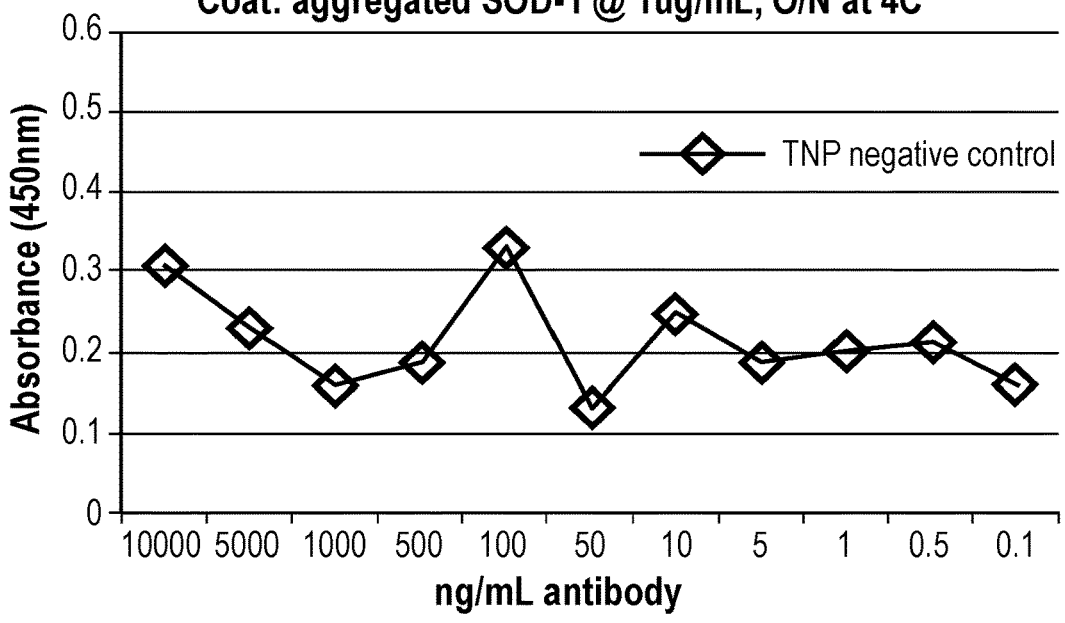
*Fig. 16*

Fig. 17

| CLONE_ID | VH_CDR1 | | | | | | | | VH_CDR2 | | | | | | | | VH_CDR3 | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | H27 | H28 | H29 | H30 | H35 | H36 | H37 | H38 | H56 | H57 | H58 | H59 | H62 | H63 | H64 | H65 | H105 | H106 | H107 | H108 | H109 | H110 | H111 | H111.1 | H111.2 | H111.3 | H112.3 | H112.2 | H112.1 | H112 | H113 | H114 | H115 | H116 | H117 |
| ABETA_B24 | G | F | T | F | S | S | Y | A | I | S | G | S | G | I | R | T | A | K | D | G | L | T | G | D | · | · | · | · | R | R | W | Y | F | D | L |
| ABETA_B73 | G | F | T | F | S | S | Y | G | I | W | Y | D | G | K | N | K | A | R | E | D | D | D | L | I | G | Y | Y | E | D | D | Y | Y | G | D | V |
| ABETA_B90 | G | F | T | F | S | S | Y | G | I | W | Y | D | G | S | K | K | A | R | R | G | R | V | G | A | · | Y | Y | · | Y | Y | Y | S | M | D | V |
| ABETA_B54 | G | F | T | F | S | [T] | Y | G | I | W | Y | D | G | S | K | K | A | R | R | G | R | V | G | [V] | T | R | D | [N] | Y | Y | Y | [G] | M | D | V |
| ABETA_B51 | G | F | T | F | S | S | H | G | I | W | Y | D | G | S | N | K | A | R | R | G | R | V | G | V | T | R | D | N | Y | Y | Y | Y | G | M | D | V |
| ABETA_B28 | G | F | T | F | S | S | [Y] | G | I | W | [F] | D | G | S | N | [E] | A | R | R | G | R | V | G | V | T | R | N | Y | Y | Y | Y | [N] | M | D | V |

ELISA: A-Beta Sera Titers - Study 17-00529 Group 3
Sigma Adjuvant mice-post 5 immunizations
Coat: ADDLs @ 1ug/ml, O/N at 4C

| Clone | ELISA (supes) | | SDS-PAGE | aSEC | ELISA titration (Ab) on PFs | Isotype | SPR offrate (mono) | Octet kinetics | SPR kinetics | Abeta Fibrils | asyn | SOD1 | iN Assay | VH/ VL Seq | Recomb |
|---|---|---|---|---|---|---|---|---|---|---|---|---|---|---|---|
| | ADDLs (1ug/mL) | PFs (1ug/mL) | | | | | | | | | | | | | |
| C11 | 0.174 | 0.183 | | | neglible | IgG2b,k | no | done | NB | | | | strong rescue | Y | Y |

*Fig. 19*

| Clone ID | 1st MWS ELISA:ADDLS 5/3/2018 | 2nd MWS ELISA-Protofibrils 5/8/2018 | 2nd MWS ELISA:ADDLS 5/8/2018 | 24 well screen ELISA:ADDLS 5/18/2018 |
|---|---|---|---|---|
| | | | | |
| 1 | 0.359 | 0.1983 | 0.1653 | 0.3186 |
| 2 | 0.3017 | neg | neg | 0.0986 |
| 3 | 0.2037 | neg | 0.1519 | 0.0922 |
| 4 | 0.2392 | neg | neg | 0.0774 |
| 5 | 0.2289 | 0.2413 | 0.184 | 0.2519 |
| 6 | 0.2212 | neg | neg | 0.0938 |
| 7 | 0.2005 | neg | neg | 0.0736 |
| 8 | 0.2151 | neg | neg | 0.0813 |
| 9 | 0.2106 | neg | neg | 0.0963 |
| 10 | 0.2064 | 0.1833 | 0.1741 | 0.1151 |
| 11 | 0.2278 | neg | 0.2248 | 0.1697 |
| 12 | 0.2208 | neg | neg | 0.0615 |
| 13 | 0.2707 | neg | neg | 0.3399 |
| 14 | 0.2212 | neg | neg | 0.062 |
| 15 | 0.2427 | neg | neg | 0.1252 |
| 16 | 0.3673 | 0.1528 | neg | 0.0816 |
| 17 | 0.2237 | neg | neg | 0.1495 |
| 18 | neg | 0.161 | neg | 0.0612 |
| 19 | neg | neg | 0.1624 | 0.1069 |
| 20 | neg | 0.2287 | 0.2119 | 0.1914 |
| 21 | neg | 0.1502 | neg | 0.1032 |
| 22 | neg | 0.1752 | neg | 0.1025 |
| 23 | neg | 0.2971 | 0.1989 | 0.0996 |
| 24 | neg | 0.1608 | neg | 0.0906 |
| 25 | neg | 0.2151 | neg | 0.0659 |
| 26 | neg | 0.1838 | neg | 0.1065 |
| 27 | neg | 0.1562 | neg | 0.0939 |
| 28 | neg | 0.4715 | neg | 0.0616 |
| 29 | neg | 0.1619 | 0.3391 | 0.0991 |
| 3D6 | | 2.33 | 2.34 | 3.0612 |

➤ All OK

- Average % area: 97.43%
- Average Retention Time: 16.26 min anti-Abeta_C13

DAD1E, Sig=280.4 Ref=300.100 (000418NewColumn\TT MB LS 060410 2618-06-04 15-66066v1BG-1591.0)

| File Information | |
|---|---|
| LC-File | 1BC-1501.D |
| File Path | C:\Chem32\1\Data\Q50418NewColumn\TT MB LS … |
| Date | 05-Jun-18, 00:20:41 |
| Sample | ABETA C15 |
| Sample Info | |
| Bar code | |
| Operator | SYSTEM |
| Method | SEC-FLD.M |
| Reference | C:\Chem32\1\Data\Q50415NewColumn\TT MB LS … |
| Analysis Time | 29.993 min |
| Sampling Rate | 0.0067 min (3.402 sec), 4500 datapoints |

Time    Area    Height    Width    Area%    Symmetry

- No peak detected due to very low concentration (negative A280 by nanodrop)

*Fig. 21 (continued)* anti-Abeta_C5

DAD1E, Sig=280.4 Ref=360.500 (050418NewColumn\TT MB LS 060410 2018-06-04 16-00-00\1BG-0901.0)

| # | Time | Area | Height | Width | Area% | Symmetry |
|---|------|------|--------|-------|-------|----------|
| 1 | 11.909 | 12.6 | 1.4E-1 | 1.1545 | 7.434 | 2.605 |
| 2 | 16.151 | 15.7 | 3.2E-1 | 0.8233 | 9.225 | 5.632 |
| 3 | 16.977 | 141.8 | 3.2 | 0.7407 | 83.341 | 0.795 |

File Information

| LC-File | 18D-1302.0 |
| File Path | C:\Chem32\1\Data\Q5Q418NewColumn\TT MB LS … |
| Date | 04-Jun-18, 23:18:07 |
| Sample | ABETA C11 |
| Sample Info | |
| Bar code | |
| Operator | SYSTEM |
| Method | SEC-FLD.34 |
| Reference | C:\Chem32\1\Data\Q5Q418NewColumn\TT MB LS … |
| Analysis Time | 29.993 min |
| Sampling Rate | 0.0067 min (0.402 sec), 4500 datapoints |

- Average % area: 83.34%
- Average Retention Time: 16.98 min

*Fig. 21 (continued)* anti-Abeta_C20

DAD1E, Sig=280.4 Ref=360.500 (050418NewColumn\TT MB LS 060410 2018-06-04 16-00-00\1BG-1701.0)

| # | Time | Area | Height | Width | Area% | Symmetry |
|---|------|------|--------|-------|-------|----------|
| 1 | 11.9 | 24.4 | 3.3E-1 | 1.2407 | 9.919 | 0.267 |
| 2 | 16.969 | 214.9 | 5.4 | 0.6592 | 87.305 | 0 |
| 3 | 18.419 | 6.8 | 1.5E-1 | 0.7448 | 2.765 | 5.26E-2 |

File Information

| LC-File | 1BF-1701.0 |
|---------|-----------|
| File Path | C:\Chem32\1\Data\Q50418NewColumn\TT MB LS … |
| Date | 05-Jun-18, 01:23:24 |
| Sample | ABETA C20 |
| Sample Info | |
| Bar code | |
| Operator | SYSTEM |
| Method | SEC-FLD.M |
| Reference | C:\Chem32\1\Data\Q50418NewColumn\TT MB LS … |
| Analysis Time | 29.993 min |
| Sampling Rate | 0.0067 min (0.402 sec), 4500 datapoints |

- Average % area: 87.32%
- Average Retention Time: 16.97 min

*Fig. 21 (continued)*

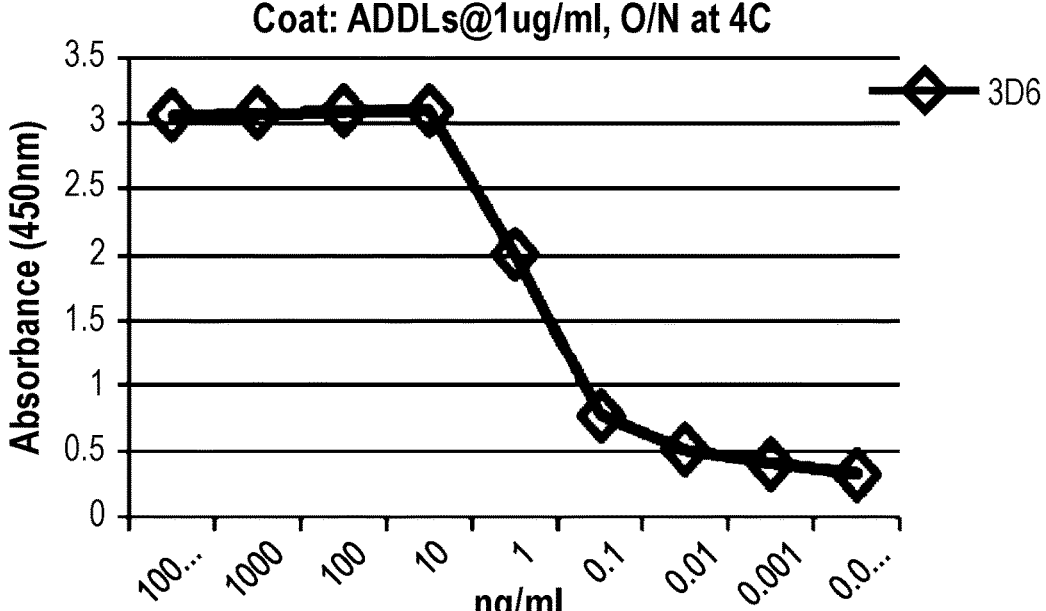
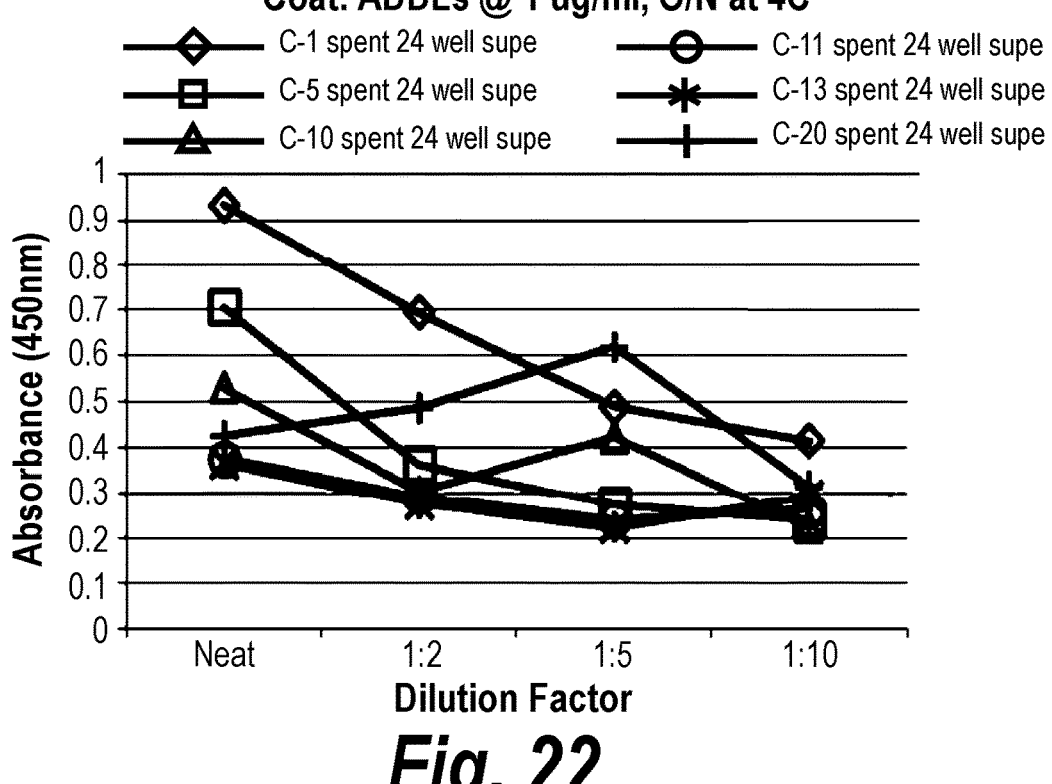
*Fig. 22*

ELISA: A-Beta Fusion C Clones
6 well supes
Coat: ADDLs @ 1ug/ml, O/N at 4C

Indirect ELISA:
Abeta Fusion C Clones - Titration against Protofibrils
Coat: 1ug/mL Protofibrils, O/N at 4C

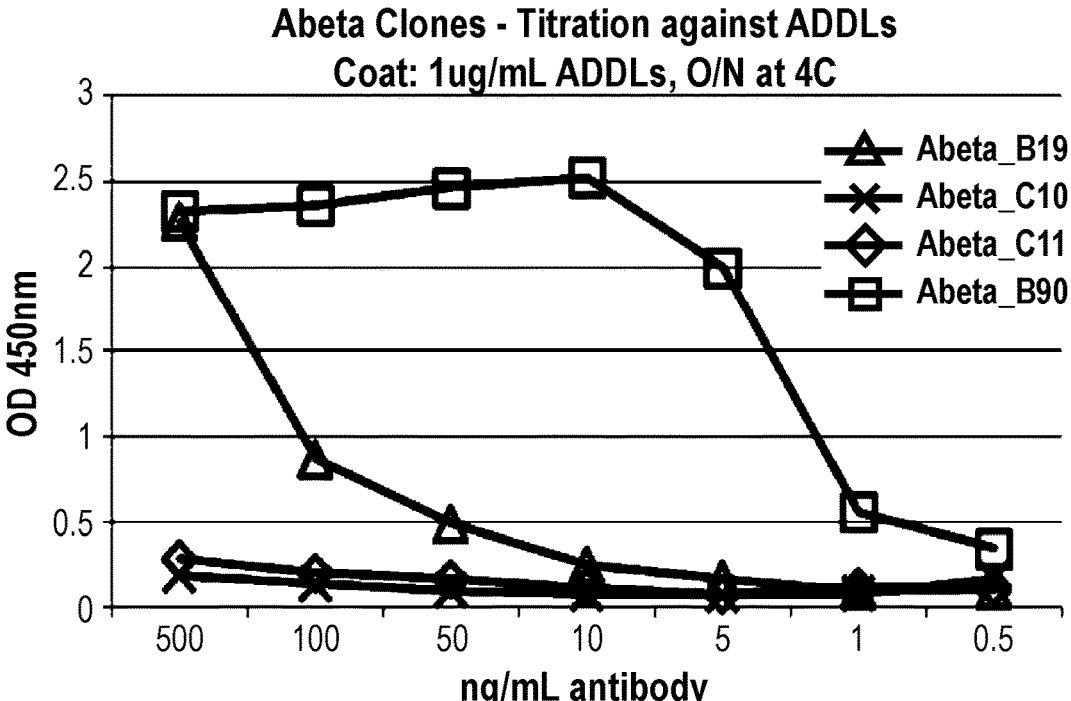
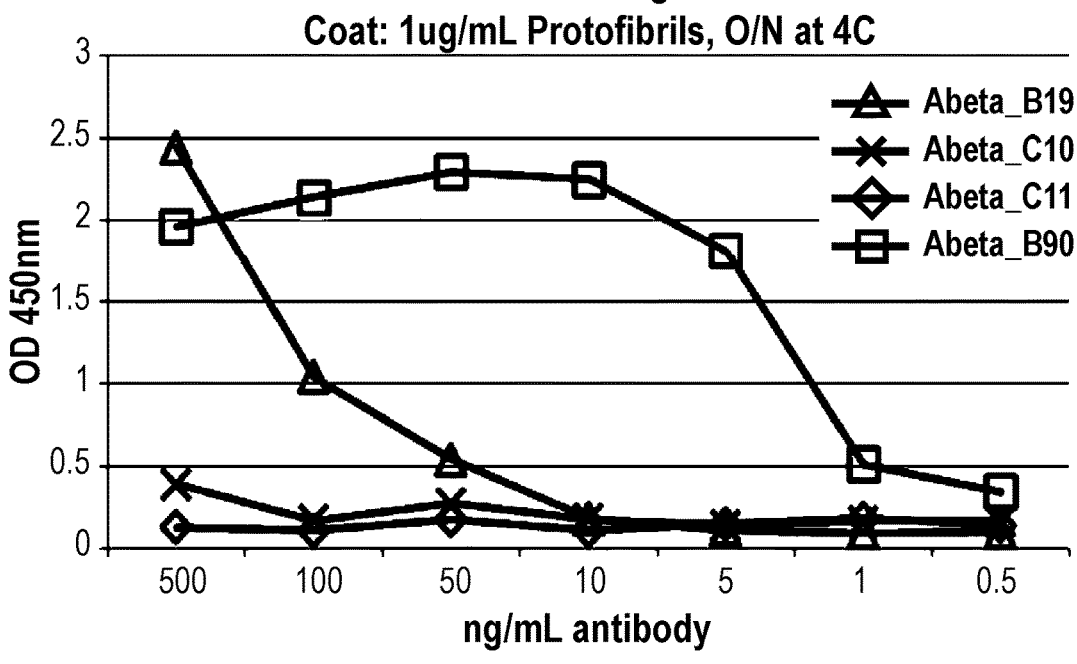
*Fig. 24*

| Ligand | Sample | Curve | Temp (°C) | Fit | ka | kd |
|---|---|---|---|---|---|---|
| BAPI | Ab1-42 | Fc=2-1 | 25 | 1:1 Binding | 1.16E+05 | 5.05E-04 |
| C13 | Ab1-42 | Fc=2-1 | 25 | 1:1 Binding | LB | LB |
| C5 | Ab1-42 | Fc=2-1 | 25 | 1:1 Binding | NB | NB |
| 1C22 hIgG1 | Ab1-42 | Fc=3-1 | 25 | 1:1 Binding | 4.09E+08 | 88.3 |
| C10 | Ab1-42 | Fc=3-1 | 25 | 1:1 Binding | NB | NB |
| C20 | Ab1-42 | Fc=3-1 | 25 | 1:1 Binding | NB | NB |
| B47-6 | Ab1-42 | Fc=4-1 | 25 | 1:1 Binding | 4.09E+04 | 0.0223 |
| C1 | Ab1-42 | Fc=4-1 | 25 | 1:1 Binding | NB | NB |
| C11 | Ab1-42 | Fc=4-1 | 25 | 1:1 Binding | NB | NB |

*Fig. 25 (continued)*

Indirect ELISA:
Abeta Clones - Titration against Fibrils
Coat: 500ng/mL Fibrils, O/N at 4C

Indirect ELISA:
Abeta Purified Fusion C, D, and E Clones
Titration against Fibrils
Coat: 1ug/mL BWH Fibrils, O/N at 4C

ELISA: Positive and Negative Controls
5G4, 2F12, 3D6, 1C22, and TNP
Coat: Alpha Synuclein @ 1ug/mL, O/N at 4C

Indirect ELISA:
Abeta Clones - Titration against Alpha synuclein
Coat: 1ug/mL alpha synuclein, O/N at 4C

0.9 ml AD-TBS extract

**10 µg Antibodies
1hr**

**100 µl Protein A mag
48 hrs**

PBS wash 3x 30 min

**80 µl 1% SDS+PBS elution
10 min RT**

**80 µl 6M GnCL
15 min 98 °C**

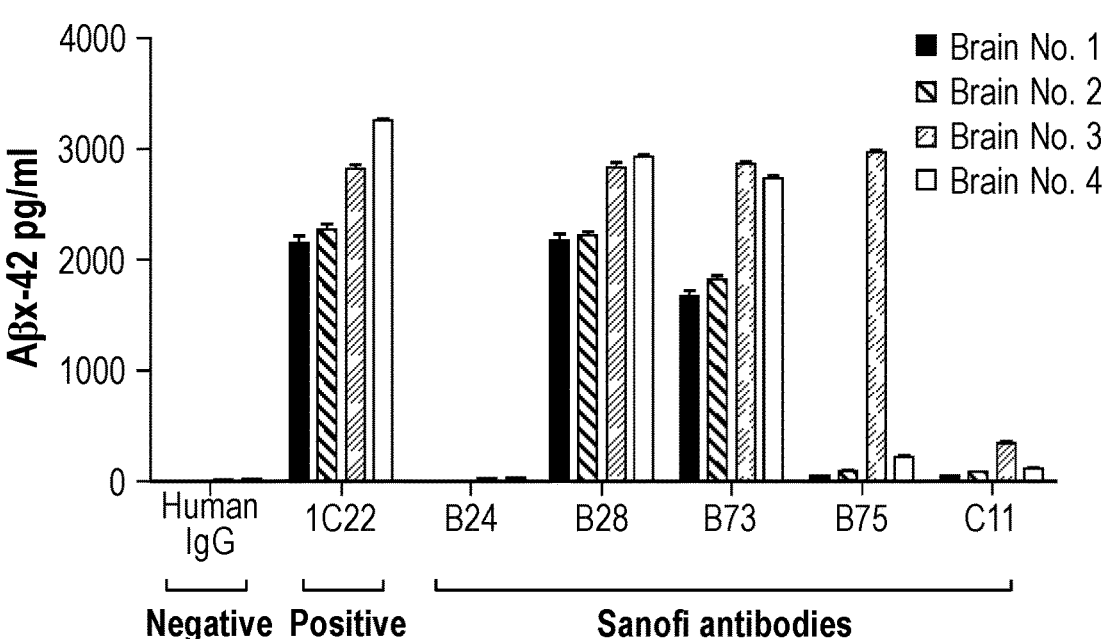
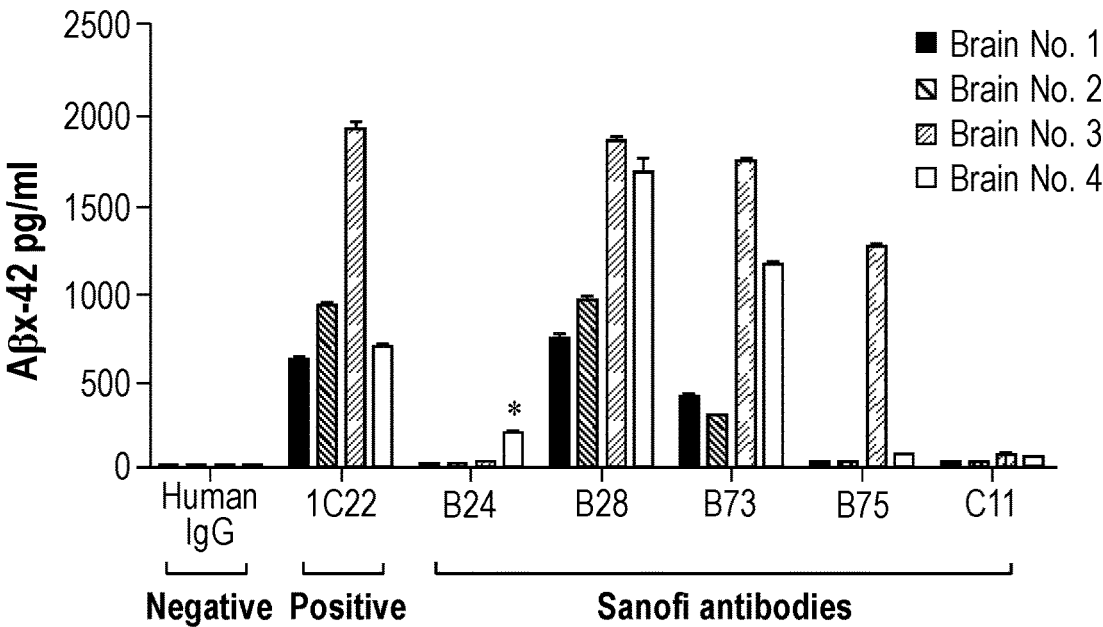
\* Cross-contamination from another sample
*Fig. 39B*

SEQUENCE LISTING

```
<160> NUMBER OF SEQ ID NOS: 146

<210> SEQ ID NO 1
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Ser Asn Leu Pro
                85                  90                  95

Leu Thr Phe Gly Gly Gly Thr Lys Val Glu Ile Lys
            100                 105

<210> SEQ ID NO 2
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Ala Met Thr Trp Val Arg Gln Ala Pro Gly Glu Gly Leu Glu Trp Val
        35                  40                  45

Ser Thr Ile Ser Gly Ser Gly Ile Arg Thr Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Lys Asp Gly Leu Thr Gly Asp Arg Arg Trp Tyr Phe Asp Leu Trp
                100                 105                 110

Gly Arg Gly Thr Leu Val Thr Val Ser Ser
            115                 120
```

<210> SEQ ID NO 3
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Leu Leu Ile
            35                  40                  45

Tyr Pro Ala Ser Ser Leu Gln Ser Gly Val Pro Ser Arg Phe Ser Gly
    50                  55                  60

Ser Gly Ser Asp Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Phe
                85                  90                  95

Thr Phe Gly Pro Gly Thr Lys Val Asp Ile Lys
            100                 105
```

<210> SEQ ID NO 4
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Gln Val Gln Leu Val Glu Ser Gly Gly Gly Val Val Gln Pro Gly Arg
1               5                   10                  15

Ser Val Arg Leu Ser Cys Ala Ala Thr Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Glu Tyr Tyr Ala Asp Ser Val
    50                  55                  60

Arg Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Arg Gly Arg Val Gly Val Thr Arg Asn Tyr Tyr Tyr Tyr Asn
            100                 105                 110

Met Asp Val Trp Gly Gln Gly Thr Thr Val Thr Val Ser Ser
        115                 120                 125

<210> SEQ ID NO 5
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Val Lys Ala Pro Lys Leu Leu Ile
        35                  40                  45

Tyr Pro Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 6
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Arg Val Gly Val Thr Arg Asn Tyr Tyr Tyr Tyr Gly
            100                 105                 110

Met Asp Val Trp Gly Gln Gly Thr Thr Val Thr Val Ser Ser
        115                 120                 125
```

```
<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Arg Asn Asp
                20                  25                  30

Leu Gly Trp Phe Gln Gln Lys Pro Gly Lys Ala Pro Lys Phe Leu Ile
            35                  40                  45

Tyr Pro Ala Ser Ser Leu Gln Gly Gly Val Pro Ser Arg Phe Ser Gly
        50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Leu Gln Asp Tyr Asn Phe Pro Trp
                85                  90                  95

Thr Phe Gly Glu Gly Thr Lys Val Glu Ile Lys
            100                 105

<210> SEQ ID NO 8
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Leu Ile Trp Tyr Asp Gly Ser Lys Lys Tyr Tyr Ala Asp Ser Val
        50                  55                  60

Gln Gly Arg Phe Thr Ile Ser Arg Asp Ser Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Arg Gly Arg Val Gly Val Thr Arg Asn Tyr Tyr Tyr Tyr Gly
            100                 105                 110

Met Asp Val Trp Gly Gln Gly Thr Thr Val Thr Val Ser Ser
            115                 120                 125

<210> SEQ ID NO 9
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 9

```
Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Glu Thr Asn Asn Arg Ala Pro Gly Val Pro Val Arg Phe
        50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Trp Val Phe Gly Gly Gly Thr Lys Leu Thr Val Leu
                100                 105
```

```
<210> SEQ ID NO 10
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 10

```
Gln Leu Gln Leu Gln Met Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Ser Pro Gly Lys Gly Leu Glu
            35                  40                  45

Trp Ile Gly Ser Ile Tyr Tyr Ser Gly Arg Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg Arg Ser Ser Gly Arg Pro Tyr Tyr Trp Gly Gln Gly Thr
                100                 105                 110

Leu Val Thr Val Ser Ser
        115
```

```
<210> SEQ ID NO 11
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 11

```
Glu Ile Val Met Thr Gln Ser Pro Ala Thr Leu Ser Val Ser Pro Gly
1               5                   10                  15

Glu Lys Ala Thr Leu Ser Cys Arg Ala Ser Gln Ser Phe Ser Ser Asn
                20                  25                  30
```

-continued

```
Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105

<210> SEQ ID NO 12
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Glu Gly Arg Thr Tyr Tyr Asp Phe Leu Thr Gly Tyr Phe Asp
            100                 105                 110

Phe Trp Gly Gln Gly Thr Leu Val Thr Val Ser Ser
        115                 120

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe His Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Tyr Val Tyr Pro Trp
                85                  90                  95

Thr Phe Gly Gln Gly Thr Lys Val Glu Ile Lys
            100                 105

<210> SEQ ID NO 14
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Arg Gly Arg Val Gly Ala Thr Arg Asp Tyr Tyr Tyr Tyr Ser
            100                 105                 110

Met Asp Val Trp Gly Gln Gly Thr Thr Val Thr Val Ser Ser
        115                 120                 125

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Tyr
                85                  90                  95

Thr Phe Gly Gln Gly Thr Lys Leu Glu Ile Lys
            100                 105

<210> SEQ ID NO 16
<211> LENGTH: 117
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Thr Thr Lys Tyr Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Asn Ser Val Thr Ala Ala Asp Thr Ala Val Tyr Tyr Cys Ala
            85                  90                  95

Arg Asp Asn Trp Gly Ser Arg Phe Asp Tyr Trp Gly Gln Gly Thr Leu
            100                 105                 110

Val Thr Val Ser Ser
        115

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Ser Val Ser Ser Ser Tyr
1               5

<210> SEQ ID NO 18
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Ala Ser
1

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gln Gln Asp Ser Asn Leu Pro Leu Thr
1               5

<210> SEQ ID NO 20
```

-continued

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Phe Thr Phe Ser Ser Tyr Ala
1               5

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Ser Gly Ser Gly Ile Arg Thr
1               5

<210> SEQ ID NO 22
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ala Lys Asp Gly Leu Thr Gly Asp Arg Arg Trp Tyr Phe Asp Leu
1               5                   10                  15

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gln Gly Ile Arg Asn Asp
1               5

<210> SEQ ID NO 24
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Pro Ala Ser
1

<210> SEQ ID NO 25
<211> LENGTH: 9
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 25

Leu Gln Asp Tyr Asn Phe Pro Phe Thr
1               5

<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Phe Thr Phe Ser Ser Tyr Gly
1               5

<210> SEQ ID NO 27
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ile Trp Phe Asp Gly Ser Asn Glu
1               5

<210> SEQ ID NO 28
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Arg Arg Gly Arg Val Gly Val Thr Arg Asn Tyr Tyr Tyr Tyr Asn
1               5                   10                  15

Met Asp Val

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gln Gly Ile Arg Asn Asp
1               5

<210> SEQ ID NO 30
<211> LENGTH: 3
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 30

Pro Ala Ser
1

<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Leu Gln Asp Tyr Asn Tyr Pro Trp Thr
1               5

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Phe Thr Phe Ser Ser His Gly
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ile Trp Tyr Asp Gly Ser Asn Lys
1               5

<210> SEQ ID NO 34
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Arg Arg Gly Arg Val Gly Val Thr Arg Asn Tyr Tyr Tyr Tyr Gly
1               5                   10                  15

Met Asp Val

<210> SEQ ID NO 35
<211> LENGTH: 6
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"

<400> SEQUENCE: 35

Gln Asp Ile Arg Asn Asp
1               5

<210> SEQ ID NO 36
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Pro Ala Ser
1

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Leu Gln Asp Tyr Asn Phe Pro Trp Thr
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Phe Thr Phe Ser Thr Tyr Gly
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ile Trp Tyr Asp Gly Ser Lys Lys
1               5

<210> SEQ ID NO 40
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 40

Ala Arg Arg Gly Arg Val Gly Val Thr Arg Asn Tyr Tyr Tyr Gly
1               5                   10                  15

Met Asp Val

<210> SEQ ID NO 41
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Thr Gly Ala Val Thr Thr Ser Asn Tyr
1               5

<210> SEQ ID NO 42
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Glu Thr Asn
1

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Leu Trp Tyr Ser Thr His Trp Val
1               5

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Ser Ile Ser Ser Ser Ser Tyr Tyr
1               5                   10

<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 45

Ile Tyr Tyr Ser Gly Arg Thr
1               5

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Arg Arg Ser Ser Gly Arg Pro Tyr Tyr
1               5                   10

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gln Ser Phe Ser Ser Asn
1               5

<210> SEQ ID NO 48
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Ala Ser
1

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gln Gln Tyr Asn Asn Trp Pro Tyr Thr
1               5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 50

Gly Phe Thr Phe Ser Ser Tyr Gly
1               5

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ile Trp Tyr Asp Gly Ser Tyr Lys
1               5

<210> SEQ ID NO 52
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Arg Glu Gly Arg Thr Tyr Tyr Asp Phe Leu Thr Gly Tyr Phe Asp
1               5                   10                  15

Phe

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gln Gly Ile Arg Asn Asp
1               5

<210> SEQ ID NO 54
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ala Ala Ser
1

<210> SEQ ID NO 55
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 55

Leu Gln Asp Tyr Val Tyr Pro Trp Thr
1               5

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Phe Thr Phe Ser Ser Tyr Gly
1               5

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ile Trp Tyr Asp Gly Ser Lys Lys
1               5

<210> SEQ ID NO 58
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ala Arg Arg Gly Arg Val Gly Ala Thr Arg Asp Tyr Tyr Tyr Tyr Ser
1               5                   10                  15

Met Asp Val

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Gly Ile Arg Asn Asp
1               5

<210> SEQ ID NO 60
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 60

Ala Ala Ser
1

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Leu Gln Asp Phe Asn Tyr Pro Tyr Thr
1               5

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Gly Ser Ile Ser Ser Tyr Tyr
1               5

<210> SEQ ID NO 63
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ile Tyr Tyr Ser Gly Thr Thr
1               5

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Arg Asp Asn Trp Gly Ser Arg Phe Asp Tyr
1               5                   10

<210> SEQ ID NO 65
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 65

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Ser Asn Leu Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 66
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Glu Gly Leu Glu Trp Val
        35                  40                  45

Ser Thr Ile Ser Gly Ser Gly Ile Arg Thr Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Lys Asp Gly Leu Thr Gly Asp Arg Arg Trp Tyr Phe Asp Leu Trp
            100                 105                 110
```

-continued

```
Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450
```

<210> SEQ ID NO 67
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

<400> SEQUENCE: 67

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Leu Leu Ile
            35                  40                  45

Tyr Pro Ala Ser Ser Leu Gln Ser Gly Val Pro Ser Arg Phe Ser Gly
        50                  55                  60

Ser Gly Ser Asp Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 68
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 68

```
Gln Val Gln Leu Val Glu Ser Gly Gly Gly Val Val Gln Pro Gly Arg
1               5                   10                  15

Ser Val Arg Leu Ser Cys Ala Ala Thr Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Glu Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Arg Val Gly Val Thr Arg Asn Tyr Tyr Tyr Tyr Asn
            100                 105                 110
```

-continued

Met Asp Val Trp Gly Gln Gly Thr Thr Val Thr Val Ser Ser Ala Ser
         115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
    450                 455

<210> SEQ ID NO 69
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

```
<400> SEQUENCE: 69

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Val Lys Ala Pro Lys Leu Leu Ile
        35                  40                  45

Tyr Pro Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Arg Val Gly Val Thr Arg Asn Tyr Tyr Tyr Tyr Gly
            100                 105                 110
```

```
Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly
    450                 455
```

<210> SEQ ID NO 71
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

<400> SEQUENCE: 71

```
Ala Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Arg Asn Asp
            20                  25                  30

Leu Gly Trp Phe Gln Gln Lys Pro Gly Lys Ala Pro Lys Phe Leu Ile
        35                  40                  45

Tyr Pro Ala Ser Ser Leu Gln Gly Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Leu Gln Asp Tyr Asn Phe Pro Trp
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 72
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Lys Lys Tyr Tyr Ala Asp Ser Val
    50                  55                  60

Gln Gly Arg Phe Thr Ile Ser Arg Asp Ser Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Arg Gly Arg Val Gly Val Thr Arg Asn Tyr Tyr Tyr Tyr Gly
            100                 105                 110
```

-continued

```
Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly
    450                 455
```

<210> SEQ ID NO 73
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 73

```
Gln Ala Val Val Thr Gln Glu Ser Ala Leu Thr Thr Ser Pro Gly Gly
1               5                   10                  15

Thr Val Ile Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Glu Thr Asn Asn Arg Ala Pro Gly Val Pro Val Arg Phe
        50                  55                  60

Ser Gly Ser Leu Ile Gly Asp Lys Ala Ala Leu Thr Ile Thr Gly Ala
65                  70                  75                  80

Gln Thr Glu Asp Asp Ala Met Tyr Phe Cys Ala Leu Trp Tyr Ser Thr
                85                  90                  95

His Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
    210                 215
```

```
<210> SEQ ID NO 74
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 74

```
Gln Leu Gln Leu Gln Met Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Ser Pro Gly Lys Gly Leu Glu
        35                  40                  45

Trp Ile Gly Ser Ile Tyr Tyr Ser Gly Arg Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg Arg Ser Ser Gly Arg Pro Tyr Tyr Trp Gly Gln Gly Thr
                100                 105                 110
```

-continued

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445
```

```
<210> SEQ ID NO 75
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Glu Ile Val Met Thr Gln Ser Pro Ala Thr Leu Ser Val Ser Pro Gly
1               5                   10                  15
```

-continued

```
Glu Lys Ala Thr Leu Ser Cys Arg Ala Ser Gln Ser Phe Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 76
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Tyr Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Glu Gly Arg Thr Tyr Tyr Asp Phe Leu Thr Gly Tyr Phe Asp
            100                 105                 110

Phe Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140
```

-continued

```
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
        435                 440                 445

Ser Leu Ser Pro Gly
    450
```

```
<210> SEQ ID NO 77
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30
```

-continued

```
Leu Gly Trp Phe His Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Val Tyr Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210
```

```
<210> SEQ ID NO 78
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

Ala Ile Ile Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Arg Gly Arg Val Gly Ala Thr Arg Asp Tyr Tyr Tyr Tyr Ser
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160
```

```
Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
    450                 455
```

<210> SEQ ID NO 79
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Thr Leu Leu Ile
            35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 80
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Thr Thr Lys Tyr Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Asn Trp Gly Ser Arg Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

-continued

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 81
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Glu Ile Val Met Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 82

Phe Ser Trp Tyr Gln Gln Lys Pro Gly Gln Ala Pro Arg Leu Leu Ile
1               5                   10                  15

Tyr

<210> SEQ ID NO 83
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Thr Arg Ala Thr Gly Ile Pro Ala Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Val Tyr Tyr Cys
        35

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Phe Gly Gly Gly Thr Lys Val Glu Ile Lys
1               5                   10

<210> SEQ ID NO 85
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 86
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Met Thr Trp Val Arg Gln Ala Pro Gly Glu Gly Leu Glu Trp Val Ser
1               5                   10                  15

Thr
```

```
<210> SEQ ID NO 87
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Tyr Tyr Ala Asp Ser Val Lys Gly Arg Phe Thr Ile Ser Arg Asp Asn
1               5                   10                  15

Ser Lys Asn Thr Met Tyr Leu Gln Met Asn Ser Leu Arg Ala Glu Asp
            20                  25                  30

Thr Ala Val Tyr Tyr Cys
        35

<210> SEQ ID NO 88
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Trp Gly Arg Gly Thr Leu Val Thr Val Ser Ser
1               5                   10

<210> SEQ ID NO 89
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 90
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Leu Gly Trp Phe Gln Gln Lys Pro Gly Lys Ala Pro Lys Leu Leu Ile
1               5                   10                  15

Tyr

<210> SEQ ID NO 91
<211> LENGTH: 36
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 91

Ser Leu Gln Ser Gly Val Pro Ser Arg Phe Ser Gly Ser Gly Ser Asp
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 92
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Phe Gly Pro Gly Thr Lys Val Asp Ile Lys
1               5                   10

<210> SEQ ID NO 93
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gln Val Gln Leu Val Glu Ser Gly Gly Gly Val Val Gln Pro Gly Arg
1               5                   10                  15

Ser Val Arg Leu Ser Cys Ala Ala Thr
            20                  25

<210> SEQ ID NO 94
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Met His Trp Val Arg Gln Ala Pro Gly Lys Gly Leu Glu Trp Val Ala
1               5                   10                  15

Val

<210> SEQ ID NO 95
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Tyr Tyr Ala Asp Ser Val Arg Gly Arg Phe Thr Ile Ser Arg Asp Asn
1               5                   10                  15

```
Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Trp Gly Gln Gly Thr Thr Val Thr Val Ser Ser
1               5                   10

<210> SEQ ID NO 97
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 98
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Leu Gly Trp Phe Gln Gln Lys Pro Val Lys Ala Pro Lys Leu Leu Ile
1               5                   10                  15

Tyr

<210> SEQ ID NO 99
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 100
```

-continued

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Phe Gly Gln Gly Thr Lys Val Glu Ile Lys
1               5                   10

<210> SEQ ID NO 101
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Met His Trp Val Arg Gln Ala Pro Gly Lys Gly Leu Glu Trp Val Ala
1               5                   10                  15

Val

<210> SEQ ID NO 103
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asn Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 104
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 104

Trp Gly Gln Gly Thr Thr Val Thr Val Ser Ser
1               5                   10

<210> SEQ ID NO 105
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ala Ile Gln Met Thr Gln Ser Pro Ser Ser Leu Ser Ala Ser Val Gly
1               5                   10                  15

Asp Arg Val Thr Ile Thr Cys Arg Thr Ser
            20                  25

<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Leu Gly Trp Phe Gln Gln Lys Pro Gly Lys Ala Pro Lys Phe Leu Ile
1               5                   10                  15

Tyr

<210> SEQ ID NO 107
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Ser Leu Gln Gly Gly Val Pro Ser Arg Phe Ser Gly Ser Gly Ser Gly
1               5                   10                  15

Thr Asp Phe Ile Leu Thr Ile Ser Ser Leu Gln Pro Glu Asp Phe Ala
            20                  25                  30

Thr Tyr Tyr Cys
        35

<210> SEQ ID NO 108
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Phe Gly Glu Gly Thr Lys Val Glu Ile Lys
1               5                   10

<210> SEQ ID NO 109
<211> LENGTH: 25
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 110
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Met His Trp Val Arg Gln Ala Pro Gly Lys Gly Leu Glu Trp Val Ala
1               5                   10                  15

Leu

<210> SEQ ID NO 111
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Tyr Tyr Ala Asp Ser Val Gln Gly Arg Phe Thr Ile Ser Arg Asp Ser
1               5                   10                  15

Ser Lys Asn Thr Leu Tyr Leu Gln Met Asn Ser Leu Arg Val Glu Asp
            20                  25                  30

Thr Ala Val Tyr Tyr Cys
        35

<210> SEQ ID NO 112
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Trp Gly Gln Gly Thr Thr Val Thr Val Ser Ser
1               5                   10

<210> SEQ ID NO 113
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

<400> SEQUENCE: 113

Gln Ala Val Val Thr Gln Glu Ser Ala Leu Thr Thr Ser Pro Gly Gly
1               5                   10                  15

Thr Val Ile Leu Thr Cys Arg Ser Ser
            20                  25

<210> SEQ ID NO 114
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ala Asn Trp Val Gln Glu Lys Pro Asp His Leu Phe Thr Gly Leu Ile
1               5                   10                  15

Gly

<210> SEQ ID NO 115
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Asn Arg Ala Pro Gly Val Pro Val Arg Phe Ser Gly Ser Leu Ile Gly
1               5                   10                  15

Asp Lys Ala Ala Leu Thr Ile Thr Gly Ala Gln Thr Glu Asp Asp Ala
            20                  25                  30

Met Tyr Phe Cys
        35

<210> SEQ ID NO 116
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Phe Gly Gly Gly Thr Lys Leu Thr Val Leu
1               5                   10

<210> SEQ ID NO 117
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gln Leu Gln Leu Gln Met Ser Gly Pro Gly Leu Val Lys Pro Ser Glu
1               5                   10                  15

Thr Leu Ser Leu Thr Cys Thr Val Ser
            20                  25

-continued

```
<210> SEQ ID NO 118
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Trp Gly Trp Ile Arg Gln Ser Pro Gly Lys Gly Leu Glu Trp Ile Gly
1               5                   10                  15

Ser

<210> SEQ ID NO 119
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Tyr Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Met Tyr Tyr Cys
        35

<210> SEQ ID NO 120
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Trp Gly Gln Gly Thr Leu Val Thr Val Ser Ser
1               5                   10

<210> SEQ ID NO 121
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Glu Ile Val Met Thr Gln Ser Pro Ala Thr Leu Ser Val Ser Pro Gly
1               5                   10                  15

Glu Lys Ala Thr Leu Ser Cys Arg Ala Ser
            20                  25

<210> SEQ ID NO 122
<211> LENGTH: 17
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic peptide"

<400> SEQUENCE: 122

Leu Ala Trp Tyr Gln Gln Lys Pro Gly Gln Ala Pro Arg Leu Leu Ile
1               5                   10                  15

Tyr

<210> SEQ ID NO 123
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Thr Arg Ala Thr Gly Ile Pro Ala Arg Phe Ser Gly Ser Gly Ser Gly
1               5                   10                  15

Thr Glu Phe Thr Leu Thr Ile Ser Ser Leu Gln Ser Glu Asp Phe Ala
            20                  25                  30

Val Tyr Tyr Cys
        35

<210> SEQ ID NO 124
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Phe Gly Gln Gly Thr Lys Leu Glu Ile Lys
1               5                   10

<210> SEQ ID NO 125
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 126
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 126

Met His Trp Val Arg Gln Ala Pro Gly Lys Gly Leu Glu Trp Val Ala
1               5                   10                  15

Val

<210> SEQ ID NO 127
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Val Glu Asp
            20                  25                  30

Thr Ala Val Tyr Tyr Cys
        35

<210> SEQ ID NO 128
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Trp Gly Gln Gly Thr Leu Val Thr Val Ser Ser
1               5                   10

<210> SEQ ID NO 129
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 130
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Leu Gly Trp Phe His Gln Lys Pro Gly Lys Ala Pro Lys Leu Leu Ile
1               5                   10                  15

Tyr

-continued

```
<210> SEQ ID NO 131
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 132
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Phe Gly Gln Gly Thr Lys Val Glu Ile Lys
1               5                   10

<210> SEQ ID NO 133
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 134
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Met His Trp Val Arg Gln Ala Pro Gly Lys Gly Leu Glu Trp Val Ala
1               5                   10                  15

Ile

<210> SEQ ID NO 135
<211> LENGTH: 38
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 135

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Val Glu Asp
            20                  25                  30

Thr Ala Val Tyr Tyr Cys
        35

<210> SEQ ID NO 136
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Trp Gly Gln Gly Thr Thr Val Thr Val Ser Ser
1               5                   10

<210> SEQ ID NO 137
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Leu Gly Trp Tyr Gln Gln Lys Pro Gly Lys Ala Pro Thr Leu Leu Ile
1               5                   10                  15

Tyr

<210> SEQ ID NO 139
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 139

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 140
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Phe Gly Gln Gly Thr Lys Leu Glu Ile Lys
1               5                   10

<210> SEQ ID NO 141
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 142
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Trp Ser Trp Ile Arg Gln Pro Pro Gly Lys Gly Leu Glu Trp Ile Gly
1               5                   10                  15

Ser

<210> SEQ ID NO 143
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Lys Tyr Asn Pro Ser Leu Lys Ser Arg Val Thr Ile Ser Val Gly Thr
1               5                   10                  15

Ser Lys Asn Gln Phe Ser Leu Lys Leu Asn Ser Val Thr Ala Ala Asp
            20                  25                  30
```

```
Thr Ala Val Tyr Tyr Cys
        35

<210> SEQ ID NO 144
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Trp Gly Gln Gly Thr Leu Val Thr Val Ser Ser
1               5                   10

<210> SEQ ID NO 145
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ile Trp Tyr Asp Gly Lys Asn Lys
1               5

<210> SEQ ID NO 146
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ala Arg Glu Asp Asp Val Leu Ile Gly Tyr Tyr Glu Asp Tyr Tyr Gly
1               5                   10                  15

Met Asp Val
```

NEUTRALIZING ANTI-AMYLOID BETA ANTIBODIES FOR THE TREATMENT OF ALZHEIMER'S DISEASE

RELATED APPLICATION

This application is a 35 U.S.C. § 371 filing of International Patent Application No. PCT/US2020/042161, filed Jul. 15, 2020, which claims the benefit of priority of U.S. Provisional Application No. 62/874,724, filed Jul. 16, 2019, the contents of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Oct. 29, 2022, is named 724878_SA9-259US_ST25.txt and is 102,880 bytes in size.

FIELD OF INVENTION

This invention relates to novel binding polypeptides that specifically bind soluble amyloid beta. This invention also relates to methods of treating Alzheimer's disease using the novel binding polypeptides provided herein.

BACKGROUND

Alzheimer's disease is the most common type of dementia. It affects tens of millions of people worldwide, and this number is rising dramatically. The amyloid hypothesis (Haass and Selkoe (1993) Cell 75:1039; Glenner and Wong (2012) Biochem Biophys Res Commun 425:534; and Selkoe and Hardy (2016) EMBO Mol Med 8:595) proposes amyloid beta (Aβ) as the main cause of the disease, and suggests that misfolding of the extracellular Aβ protein accumulated in senile plaques (Bloom (2014) JAMA Neurol. 71:505) and the intracellular deposition of misfolded tau protein in neurofibrillary tangles cause memory loss and abnormal executive function and result in cognitive and behavioral decline over time. Accumulated Aβ peptide is the main component of senile (amyloid) plaques and derives from the proteolytic cleavage of a larger glycoprotein named amyloid precursor protein (APP) (Chen et al. (2017) Acta Pharmacologica Sinica 38:1205; Liu et al. (2019) J. Cell Biol. 218:644).

Aβ monomers aggregate into various types of assemblies, including oligomers, protofibrils and amyloid fibrils. Amyloid fibrils are large and insoluble, and they can further assemble into amyloid plaques, while amyloid oligomers are aqueously soluble and may spread throughout the brain. Aβ encompasses a group of peptides ranging in size from 37 to 49 residues. Amyloid plaques with Aβ as the main component are most commonly found in the limbic and neocortex in the brain of Alzheimer's disease patients. Aβ (1-42) is the major proteinaceous component of amyloid deposits in Alzheimer's disease.

While amyloid fibrils are larger, insoluble, and aggregate into fibrous amyloid plaques forming histological lesions that are characteristic of Alzheimer's disease, Aβ oligomers are soluble and may diffuse throughout the brain. The size distribution of Aβ oligomers is heterogeneous. There is a broad consensus for the preferential accumulation of a soluble high-molecular-weight species of approximately 100-200 kDa under relatively physiological conditions in vitro (Goldsbury et al. (2000) J. Struct. Biol. 130:217; Nichols et al. (2002) Biochemistry 41:6115; Lashuel et al. (2003) J. Mol. Biol. 332:795; Walsh et al. (1997) J. Biol. Chem. 272:22364; Soreghan et al. (1994) J. Biol. Chem. 269:28551). Aβ monomers can form higher-order assemblies ranging from low-molecular-weight oligomers, including dimers, trimers and tetramers, to midrange molecular weight oligomers, including hexamers and dodecamers, to soluble protofibrils and insoluble fibrils (Chen et al., Supra).

Approaches using monoclonal antibodies to target amyloid β-protein (Aβ) constitute the largest and most advanced therapeutic effort to treat Alzheimer's disease (AD) (Liu et al. (2016) Drugs Aging 33:685; Golde (2014) Alzheimer's Res. Ther. 6:3; van Dyck (2017) Biol. Psychiatry 83:311). Despite generally good outcomes in preclinical mouse models, anti-Aβ immunotherapy has yielded limited success in humans (Golde, van Dyck, Supra). Explanations offered to account for the poor translation of pre-clinical lead antibodies into human therapies include imperfect trial design, intervention at a disease stage when there is already significant neural loss, and inappropriate target selectivity of the antibodies used (Golde, Supra; Kohyama and Matsumoto (2015) Immunotargets Ther. 4:27; Selkoe and Hardy, Supra).

Accordingly, there remains a need for alternative therapeutic monoclonal antibodies for the treatment of Alzheimer's disease.

SUMMARY

The present invention is based on the discovery of novel anti-amyloid beta (Aβ) binding proteins (e.g., antibodies) that specifically bind to an epitope of one or more species of aqueously soluble, AD brain-derived synaptotoxic Aβ.

Accordingly, in certain aspects, an isolated binding polypeptide that specifically binds soluble Aβ, wherein the binding polypeptide comprises three heavy chain complementary determining region (HCDR) sequences and three light chain complementary determining region (LCDR) sequences, is provided. In certain embodiments, the three HCDR sequences are selected from the group consisting of SEQ ID NOs: 20, 21, 22, 26, 27, 28, 32, 33, 34, 38, 39, 40, 44, 45, 46, 50, 51, 52, 56, 57, 58, 62, 63, and 64, and the three LCDR sequences are selected from the group consisting of SEQ ID NOs: 17, 18, 19, 23, 24, 25, 29, 30, 31, 35, 36, 37, 41, 42, 43, 47, 48, 49, 53, 54, 55, 59, 60 and 61.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ, wherein the binding polypeptide comprises a heavy chain variable region (HCVR) sequence and a light chain variable region (LCVR) sequence, is provided. In certain embodiments, the HCVR sequence is selected from the group consisting of SEQ ID NOs: 2, 4, 6, 8, 10, 12, 14 and 16, and the LCVR sequence is selected from the group consisting of SEQ ID NOs: 1, 3, 5, 7, 9, 11, 13 and 15.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ, wherein the binding polypeptide comprises an HCVR/LCVR sequence pair, is provided. In certain embodiments, the HCVR/LCVR pair is selected from the group consisting of SEQ ID NOs: 2/1, 4/3, 6/5, 8/7, 10/9, 12/11, 14/13 and 16/15.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 20, 21 and 22, and LCDR sequences of SEQ ID NOs: 17, 18 and 19 is provided. In certain aspects, an isolated binding polypeptide that specifically binds soluble Aβ that comprises the HCVR/LCVR pair of SEQ ID NOs: 2 and 1 is provided. In certain aspects, an isolated binding polypeptide that specifically binds soluble Aβ that comprises the full heavy chain/light chain sequence pair of SEQ ID NOs: 66 and 65 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 26, 27 and 28 and LCDR sequences of SEQ ID NOs: 23, 24 and 25 is provided. In certain aspects, an isolated binding polypeptide that specifically binds soluble Aβ that comprises the HCVR/LCVR pair of SEQ ID NOs: 4 and 3 is provided. In certain aspects, an isolated binding polypeptide that specifically binds soluble Aβ that comprises the full heavy chain/light chain sequence pair of SEQ ID NOs: 68 and 67 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 32, 33 and 34, and LCDR sequences of SEQ ID NOs: 29, 30 and 31 is provided. In certain aspects, an isolated binding polypeptide that specifically binds soluble Aβ that comprises the HCVR/LCVR pair of SEQ ID NOs: 6 and 5 is provided. In certain aspects, an isolated binding polypeptide that specifically binds soluble Aβ that comprises the full heavy chain/light chain sequence pair of SEQ ID NOs: 70 and 69 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 38, 39 and 40 and LCDR sequences of SEQ ID NOs: 35, 36 and 37 is provided. In certain aspects, an isolated binding polypeptide that specifically binds soluble Aβ that comprises the HCVR/LCVR pair of SEQ ID NOs: 8 and 7 is provided. In certain aspects, an isolated binding polypeptide that specifically binds soluble Aβ that comprises the full heavy chain/light chain sequence pair of SEQ ID NOs: 72 and 71 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 44, 45 and 46 and LCDR sequences of SEQ ID NOs: 41, 42 and 43 is provided. In certain aspects, an isolated binding polypeptide that specifically binds soluble Aβ that comprises the HCVR/LCVR pair of SEQ ID NOs: 10 and 9 is provided. In certain aspects, an isolated binding polypeptide that specifically binds soluble Aβ that comprises the full heavy chain/light chain sequence pair of SEQ ID NOs: 74 and 73 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 50, 51 and 52, and LCDR sequences of SEQ ID NOs: 47, 48 and 49 is provided. In certain aspects, an isolated binding polypeptide that specifically binds soluble Aβ that comprises the HCVR/LCVR pair of SEQ ID NOs: 12 and 11 is provided. In certain aspects, an isolated binding polypeptide that specifically binds soluble Aβ that comprises the full heavy chain/light chain sequence pair of SEQ ID NOs: 76 and 75 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 56, 57 and 58, and LCDR sequences of SEQ ID NOs: 53, 54 and 55 is provided. In certain aspects, an isolated binding polypeptide that specifically binds soluble Aβ that comprises the HCVR/LCVR pair of SEQ ID NOs: 14 and 13 is provided. In certain aspects, an isolated binding polypeptide that specifically binds soluble Aβ that comprises the full heavy chain/light chain sequence pair of SEQ ID NOs: 78 and 77 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble Aβ comprises HCDR sequences of SEQ ID NOs: 62, 63 and 64, and LCDR sequences of SEQ ID NOs: 59, 60 and 61 is provided. In certain aspects, an isolated binding polypeptide that specifically binds soluble Aβ that comprises the HCVR/LCVR pair of SEQ ID NOs: 16 and 15 is provided. In certain aspects, an isolated binding polypeptide that specifically binds soluble Aβ that comprises the full heavy chain/light chain sequence pair of SEQ ID NOs: 80 and 79 is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, an isolated binding polypeptide that specifically binds soluble amyloid beta (Aβ), wherein the binding polypeptide comprises three heavy chain complementary determining region (HCDR) sequences and three light chain complementary determining region (LCDR) sequences, wherein the three HCDR sequences are selected from the group consisting of SEQ ID NOs: 20, 21, 22, 50, 51, 52, 44, 45, 46, 26, 27, 28, 62, 63, and 64, and wherein the three LCDR sequences are selected from the group consisting of SEQ ID NOs: 17, 18, 19, 47, 48, 49, 41, 42, 43, 23, 24, 25, 59, 60 and 61, is provided.

In certain exemplary embodiments, the binding polypeptide comprises an antibody or an antigen-binding fragment thereof, which is optionally human and/or is optionally IgG1.

In certain exemplary embodiments, the binding polypeptide comprises a heavy chain variable region (HCVR)/light chain variable region (LCVR) sequence pair selected from the group consisting of: SEQ ID NOs: 2 and 1; SEQ ID NOs: 10 and 9; SEQ ID NOs: 4 and 3; SEQ ID NOs: 12 and 11; and SEQ ID NOs: 16 and 15.

In certain exemplary embodiments, the three HCDR sequences comprise SEQ ID NOs: 20, 21 and 22, and the three LCDR sequences comprise SEQ ID NOs: 17, 18 and 19. In certain exemplary embodiments, the three HCDR sequences comprise SEQ ID NOs: 44, 45 and 46, and the three LCDR sequences comprise SEQ ID NOs: 41, 42 and 43. In certain exemplary embodiments, the three HCDR sequences comprise SEQ ID NOs: 26, 27 and 28, and the three LCDR sequences comprise SEQ ID NOs: 23, 24 and 25. In certain exemplary embodiments, the three HCDR sequences comprise SEQ ID NOs: 50, 51 and 52, and the three LCDR sequences comprise SEQ ID NOs: 47, 48 and 49. In certain exemplary embodiments, the three HCDR sequences comprise SEQ ID NOs: 62, 63 and 64, and the three LCDR sequences comprise SEQ ID NOs: 59, 60 and 61.

In certain exemplary embodiments, the HCVR/LCVR sequence pair is SEQ ID NOs: 2 and 1. In certain exemplary embodiments, the HCVR/LCVR sequence pair is SEQ ID NOs: 10 and 9. In certain exemplary embodiments, the HCVR/LCVR sequence pair is SEQ ID NOs: 4 and 3. In certain exemplary embodiments, the HCVR/LCVR sequence pair is SEQ ID NOs: 12 and 11. In certain exemplary embodiments, the HCVR/LCVR sequence pair is SEQ ID NOs: 16 and 15.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain aspects, a pharmaceutical composition comprising an isolated binding polypeptide that specifically binds soluble amyloid beta (Aβ), wherein the binding polypeptide comprises three heavy chain complementary determining region (HCDR) sequences and three light chain complementary determining region (LCDR) sequences, wherein the three HCDR sequences are selected from the group consisting of SEQ ID NOs: 20, 21, 22, 50, 51, 52, 44, 45, 46, 26, 27, 28, 62, 63, and 64, and wherein the three LCDR sequences are selected from the group consisting of SEQ ID NOs: 17, 18, 19, 47, 48, 49, 41, 42, 43, 23, 24, 25, 59, 60 and 61, and a pharmaceutically acceptable carrier, is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain exemplary embodiments, a method of treating Alzheimer's disease in a subject comprising administering to the subject an effective amount of the pharmaceutical composition is provided.

In certain aspects, a pharmaceutical composition comprising an isolated binding polypeptide that specifically binds soluble amyloid beta (Aβ), wherein the binding polypeptide comprises a heavy chain variable region (HCVR)/light chain variable region (LCVR) sequence pair selected from the group consisting of: SEQ ID NOs: 2 and 1; SEQ ID NOs: 10 and 9; SEQ ID NOs: 4 and 3; SEQ ID NOs: 12 and 11; and SEQ ID NOs: 16 and 15, and a pharmaceutically acceptable carrier, is provided.

In certain exemplary embodiments, the soluble Aβ is synaptotoxic. In certain exemplary embodiments, the binding polypeptide neutralizes Aβ synaptotoxicity. In certain exemplary embodiments, the soluble Aβ has a molecular weight of between about 20 kD and about 100 kD.

In certain exemplary embodiments, the binding polypeptide does not specifically bind monomeric Aβ, protofibrillar Aβ or fibrillar Aβ. In certain exemplary embodiments, the binding polypeptide does not specifically bind a protein aggregate. In certain exemplary embodiments, the binding polypeptide does not specifically bind to an amyloid plaque present in brain derived from a subject having Alzheimer's disease. In certain exemplary embodiments, the binding polypeptide specifically binds soluble Aβ of brain derived from a subject having Alzheimer's disease. In certain exemplary embodiments, the binding is immunoabsorption. In certain exemplary embodiments, the soluble Aβ is present in one or more soluble fractions obtained from brain derived from a subject having Alzheimer's disease. In certain exemplary embodiments, the binding polypeptide neutralizes synaptotoxicity of the soluble Aβ.

In certain exemplary embodiments, a method of treating Alzheimer's disease in a subject comprising administering to the subject an effective amount of the pharmaceutical composition is provided.

In certain aspects, an isolated polynucleotide encoding a binding polypeptide that specifically binds soluble amyloid beta (Aβ), wherein the binding polypeptide comprises three heavy chain complementary determining region (HCDR) sequences and three light chain complementary determining region (LCDR) sequences, wherein the three HCDR sequences are selected from the group consisting of SEQ ID NOs: 20, 21, 22, 50, 51, 52, 44, 45, 46, 26, 27, 28, 62, 63, and 64, and wherein the three LCDR sequences are selected from the group consisting of SEQ ID NOs: 17, 18, 19, 47, 48, 49, 41, 42, 43, 23, 24, 25, 59, 60 and 61, and a pharmaceutically acceptable carrier, is provided.

In certain exemplary embodiments, a vector encoding the polynucleotide is provided.

In certain exemplary embodiments, a host cell comprising the polynucleotide or the vector is provided.

BRIEF DESCRIPTION OF THE DRAWINGS

The foregoing and other features and advantages of the present invention will be more fully understood from the following detailed description of illustrative embodiments taken in conjunction with the accompanying drawings.

Figure 1:
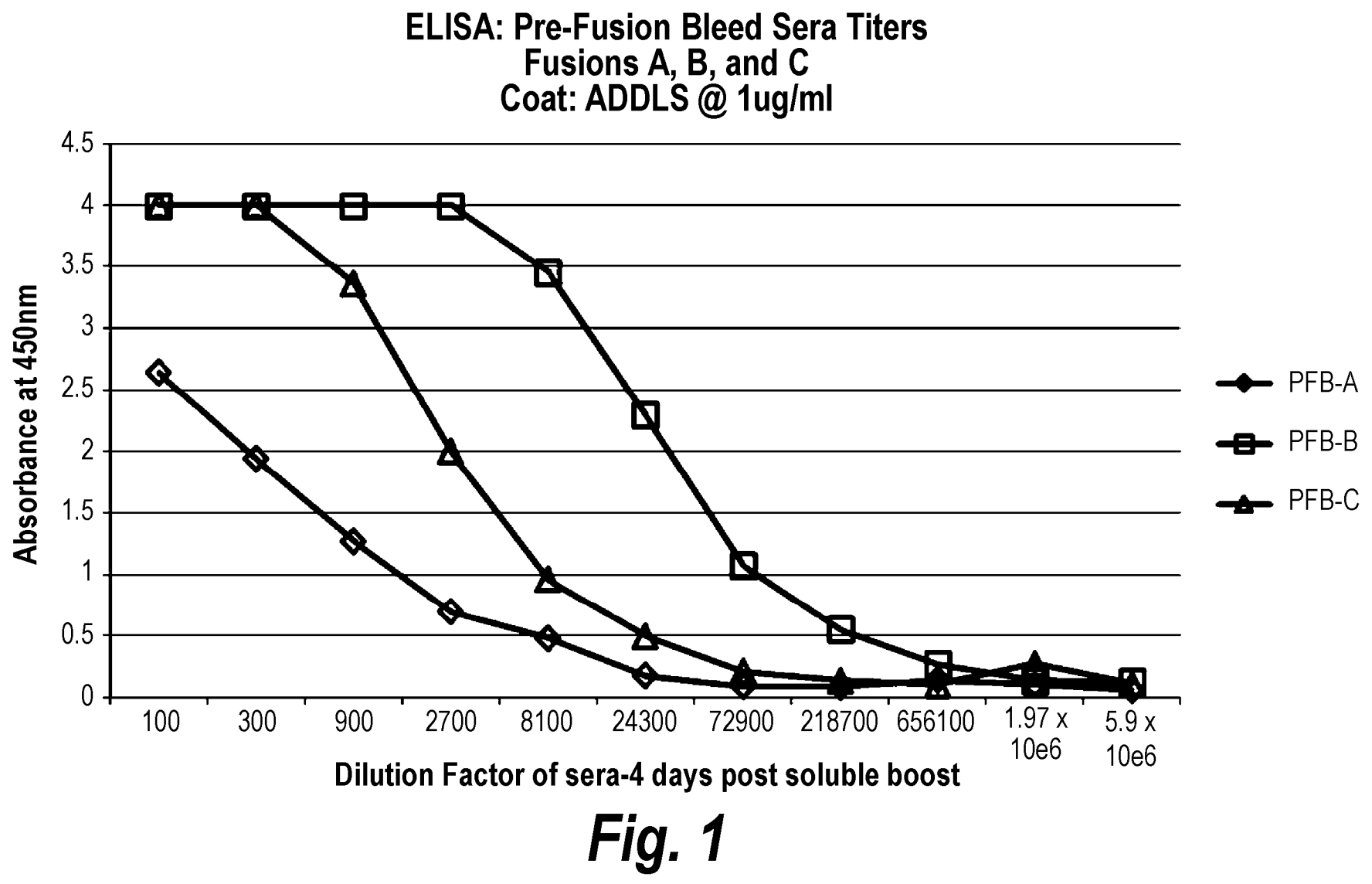

FIG. 1 graphically depicts pre-fusion titers of mice selected for fusions A (FusA), B (FusB) and C (FusC). FusA, sonicated amyloid plaques from human Alzheimer's disease (AD) brains; FusB, aggregated synthetic amyloid beta (Aβ); FusC, AD-amyloid-plaque seeded synthetic Aβ.

FIG. 3 graphically depicts post-fifth immunization titers for aggregated synthetic Aβ cohort 2 showing results obtained by ELISA based on synthetic Aβ-derived diffusible ligands (ADDLs) (1 μg/ml, overnight at 4° C.). Mouse M13 was to be used to produce hybridoma cells (titer, 3× pre-immunized background).

FIG. 4 depicts a table showing a summary of FusB results.

FIG. 5 graphically depicts select absolute size exclusion chromatography (aSEC) profiles of purified FusB clones.

FIG. 8 depicts Octet analyses of Aβ 1-40 monomer vs. PFs kinetics with selected clones.

FIG. 9 depicts a table showing Octet kinetics of Aβ 1-40 monomer vs. PFs kinetics with controls.

FIG. 10 depicts a counter-screen using fibrils with clones B24, B28, B51, B54, B90, C11 and B73.

FIG. 11 graphically depicts a counter-screen using fibrils with FusB clones.

FIG. 12 graphically depicts counter-screening using aggregated alpha-synuclein with FusB clones.

FIG. 17 is a table showing sequence alignments of the VH regions for exemplary FusB clones. Figure discloses SEQ ID NOS 20-22, 26, 145-146, 26, 39, 58, 38-39, 34, 32-34, and 26-28, respectively, in order of appearance.

FIG. 19 is a table showing characteristics of an exemplary FusC clone.

FIG. 20 is a table showing ELISA screening data for FusC clones.

FIG. 24 graphically depicts repeat titration ELISA results of purified C10 and purified C11 clones on synthetic ADDLs vs. synthetic PFs. No binding to ADDLs or PFs was observed for purified clone C10 or purified clone C11.

FIG. 39A-FIG. 39B depict immunoprecipitation of four human brain extracts using mAbs B24, B28, B73, B75 and C11 and protein-A beads. A) Schematically depicts the immunoprecipitation work-flow of human brain extracts. B) Shows an Aβ x-42 ELISA analysis of sequential elution of immunoprecipitants of four brain extracts by 1% SDS (top graph) and 6 M guanidine hydrochloride (bottom graph) (n=3, mean±SD). 1C22 was used as positive control and human IgG was used as negative control for immunoprecipitation.

DETAILED DESCRIPTION

Figure 2B:
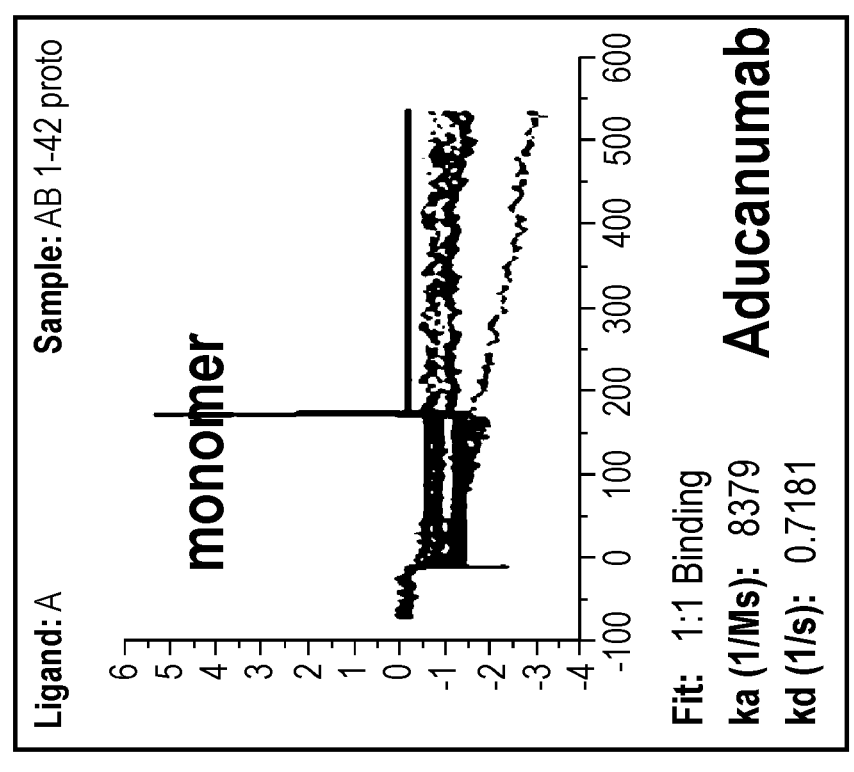
FIG. 2A-FIG. 2B graphically depict counter-screens showing selectivity for oligomeric vs. monomeric Aβ.
Figure 2A:
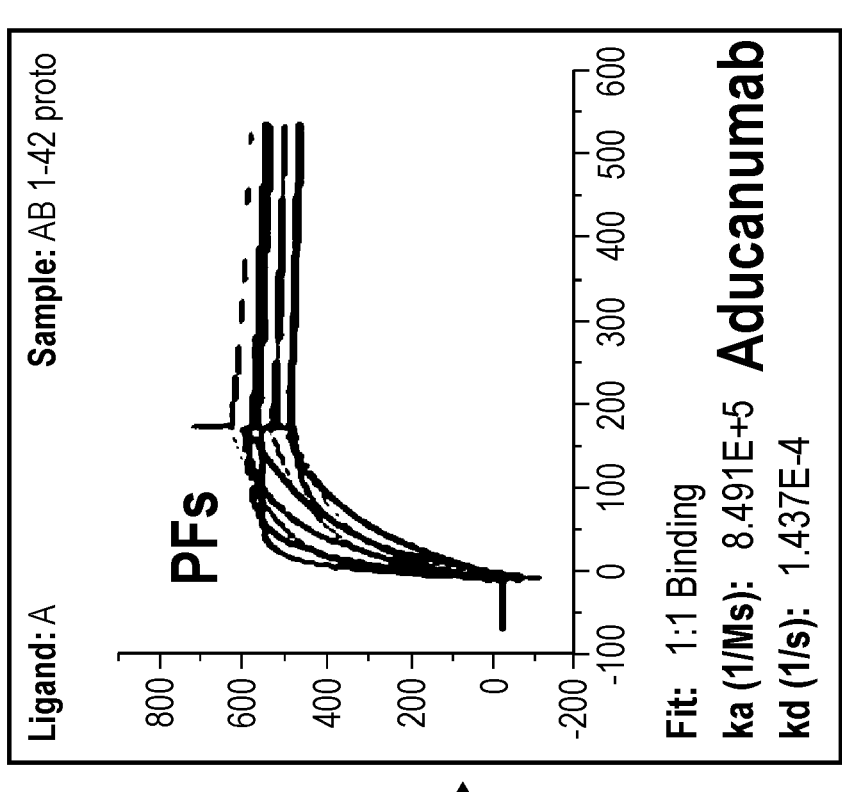
Figure 6:
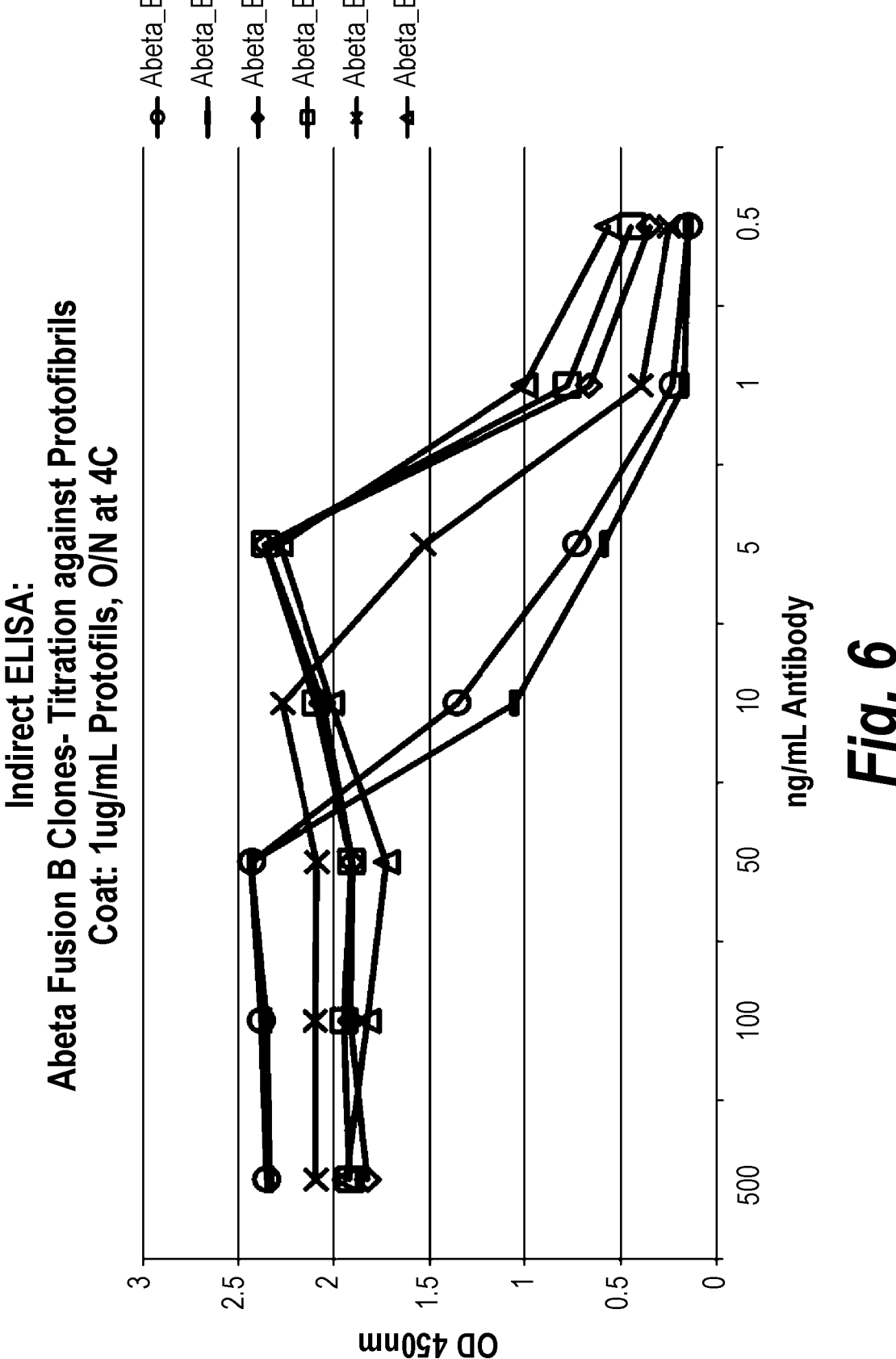
FIG. 6 graphically depicts indirect ELISA results for FusB clones titrated against protofibrils (PFs). Coat: 1 μg/ml PFs, overnight at 4° C.
Figure 7:
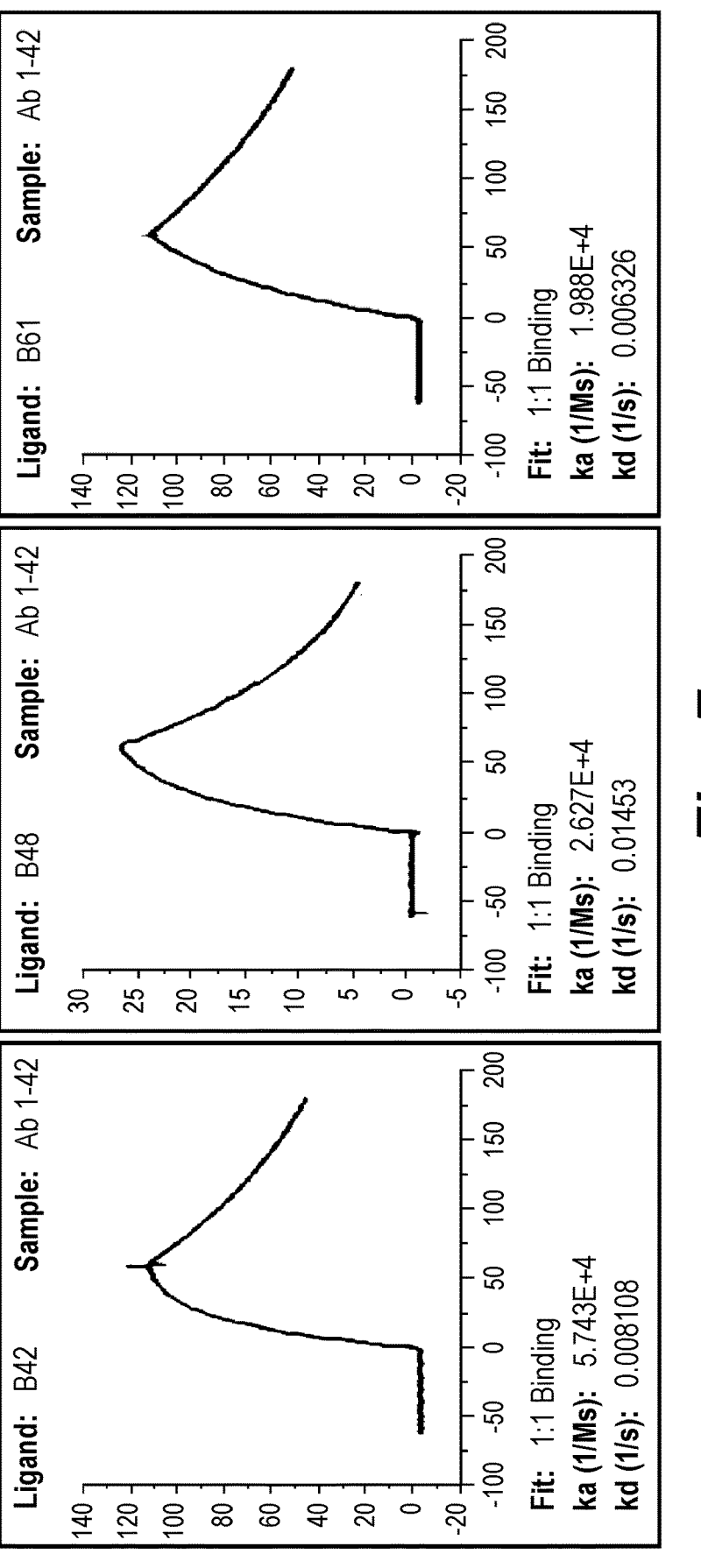
FIG. 7 depicts BIAcore analysis of counter screen for monomer showing off-rate assessment of purified FusB clones for Aβ 1-42 monomer.
Figure 7:
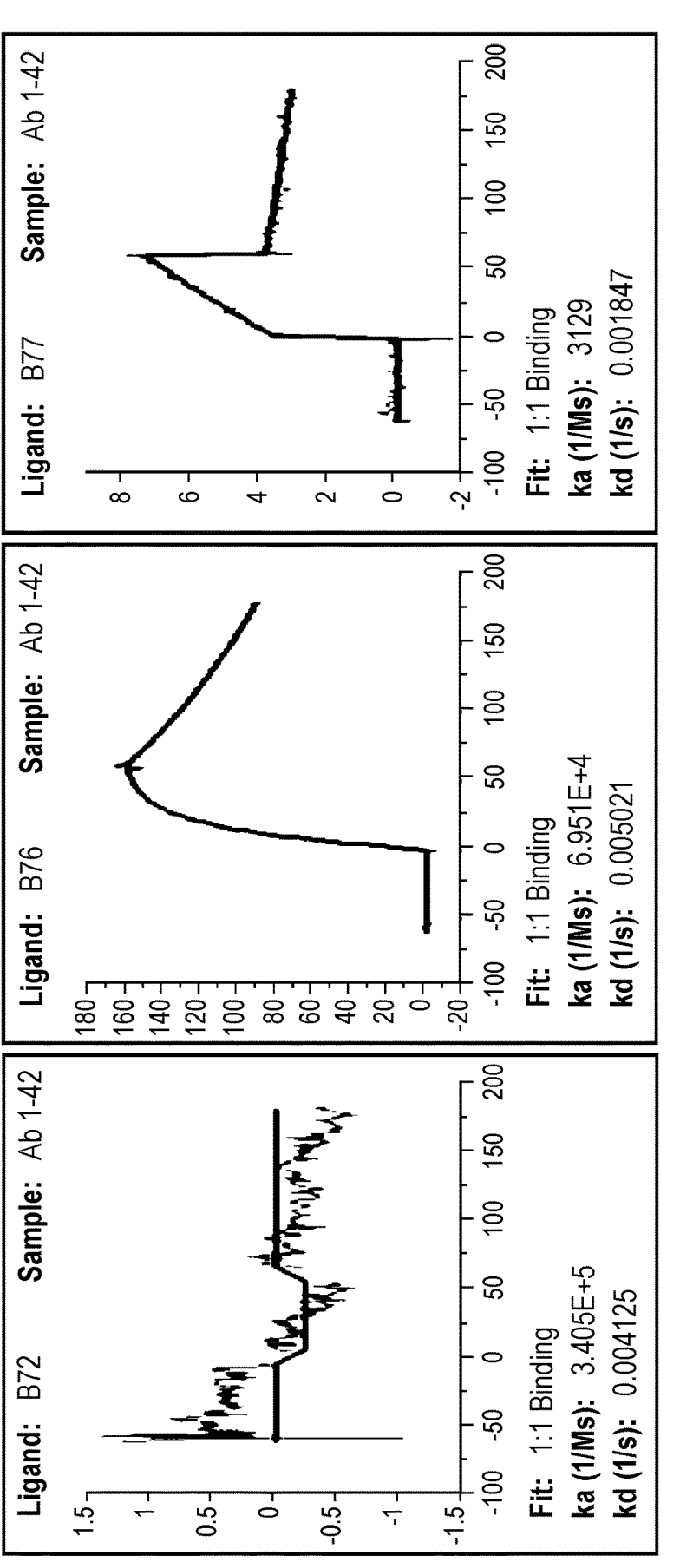
Figure 7:
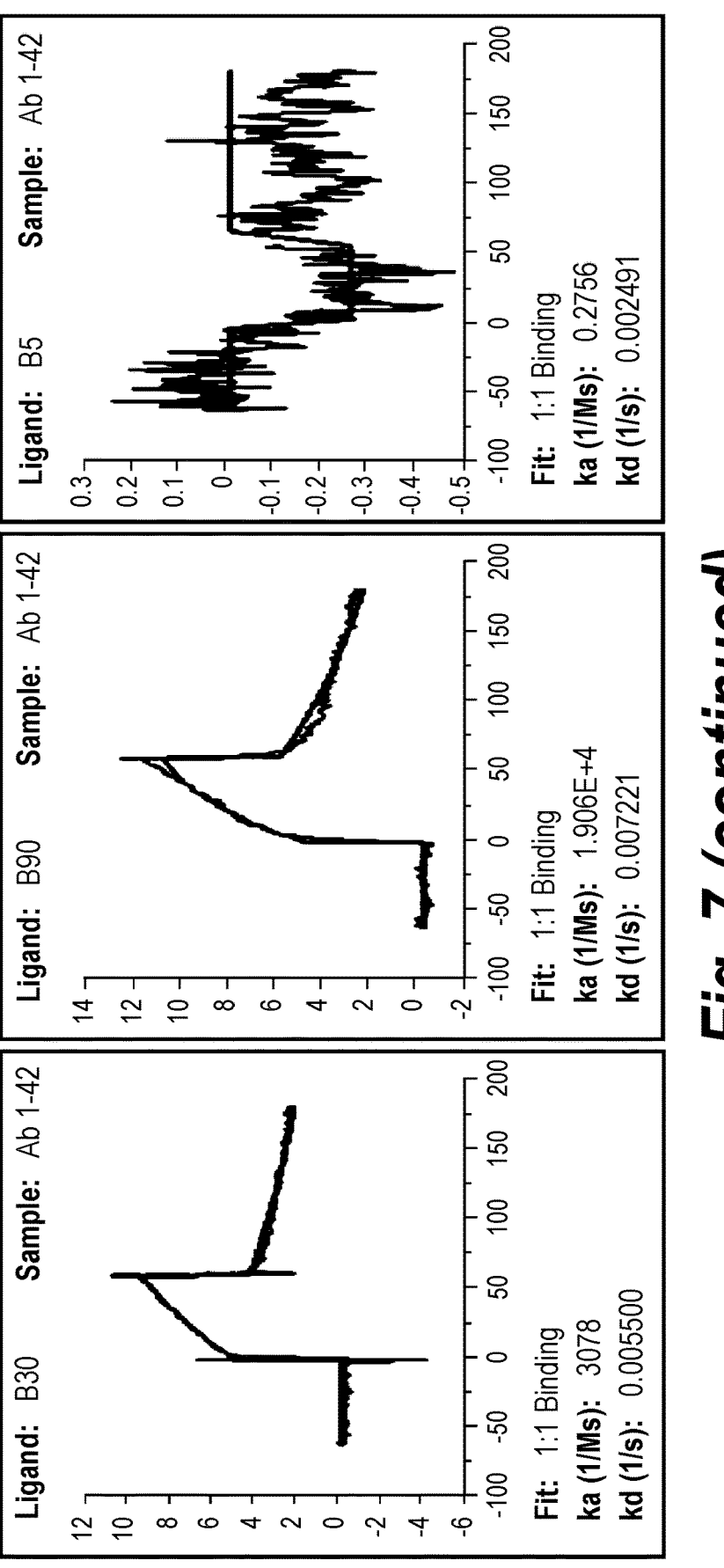
Figure 7:
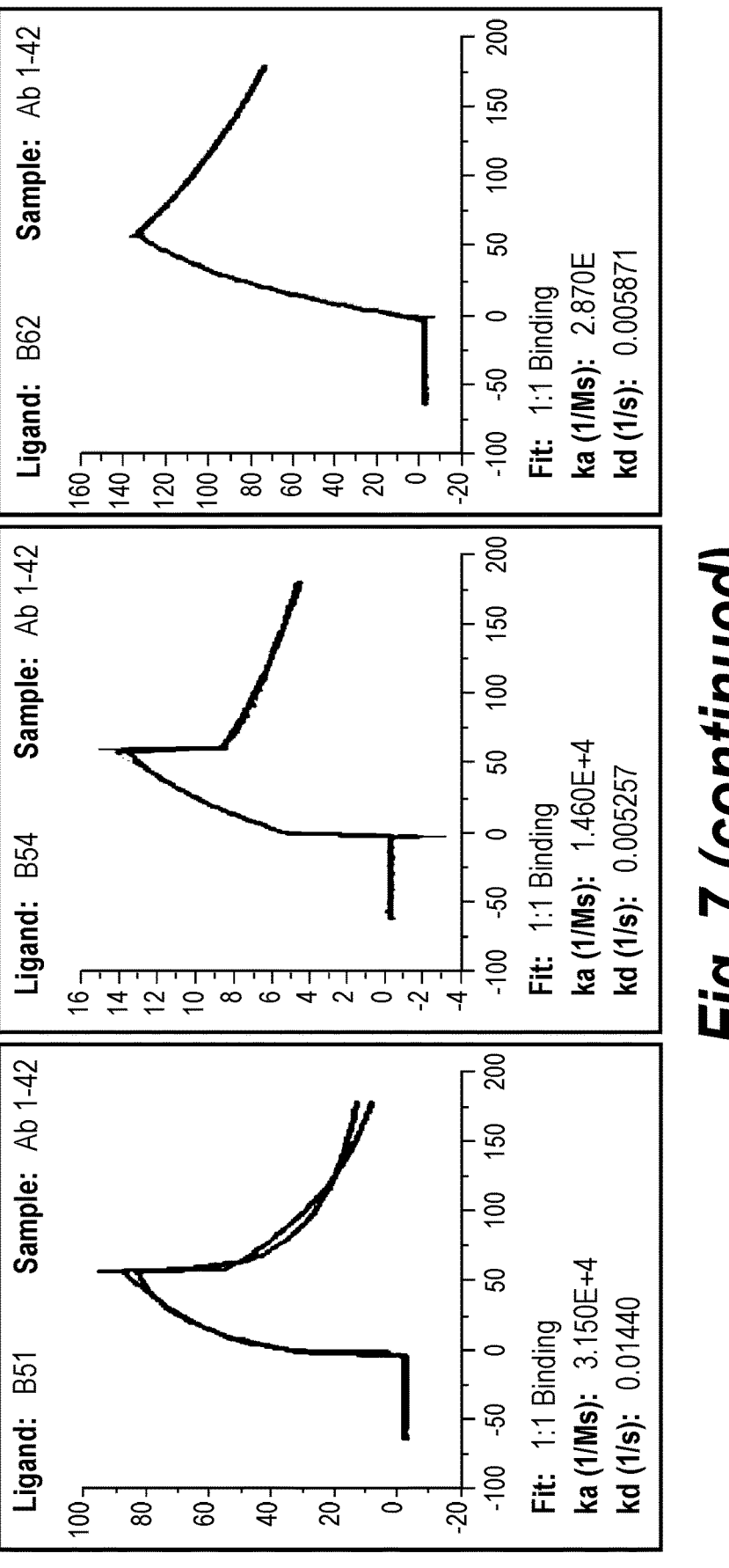
Figure 7:
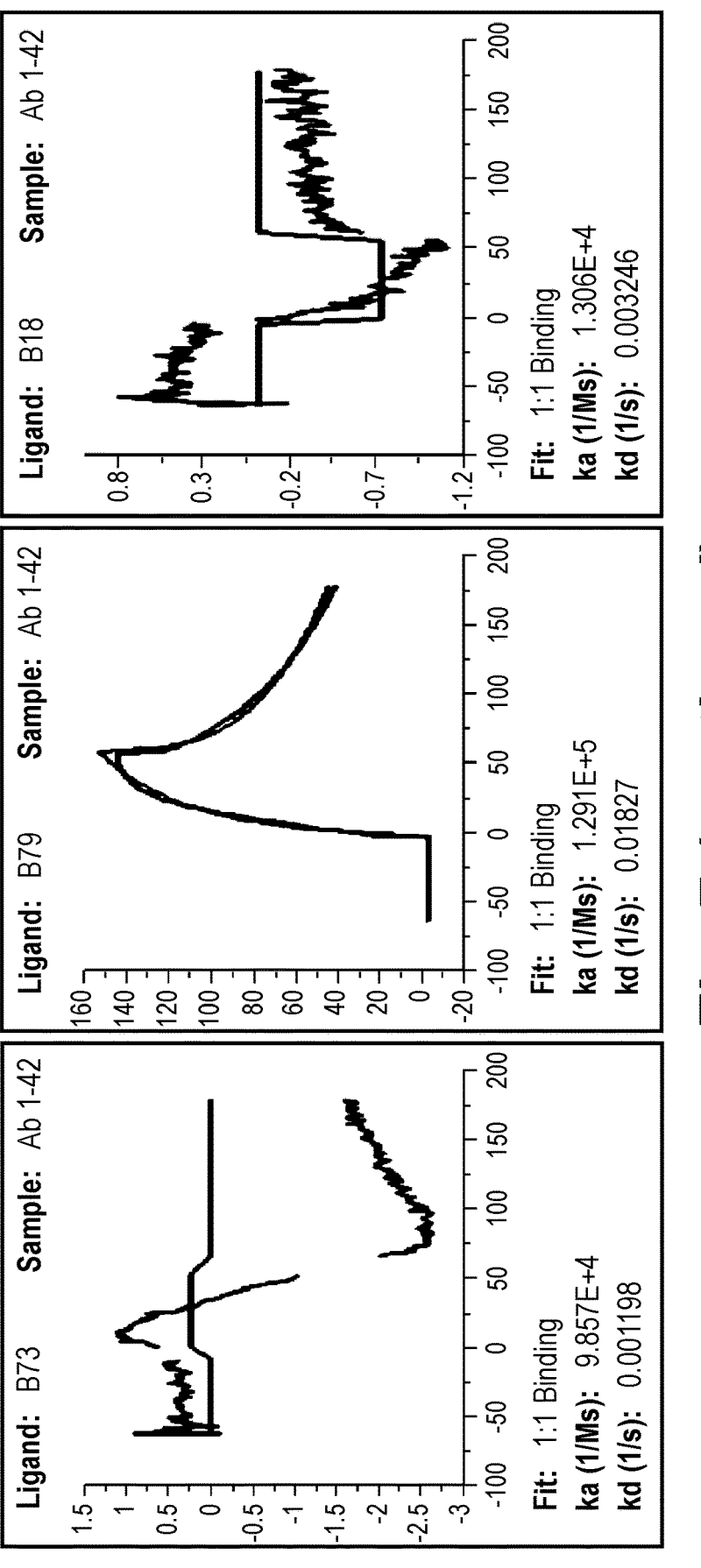
Figure 7:
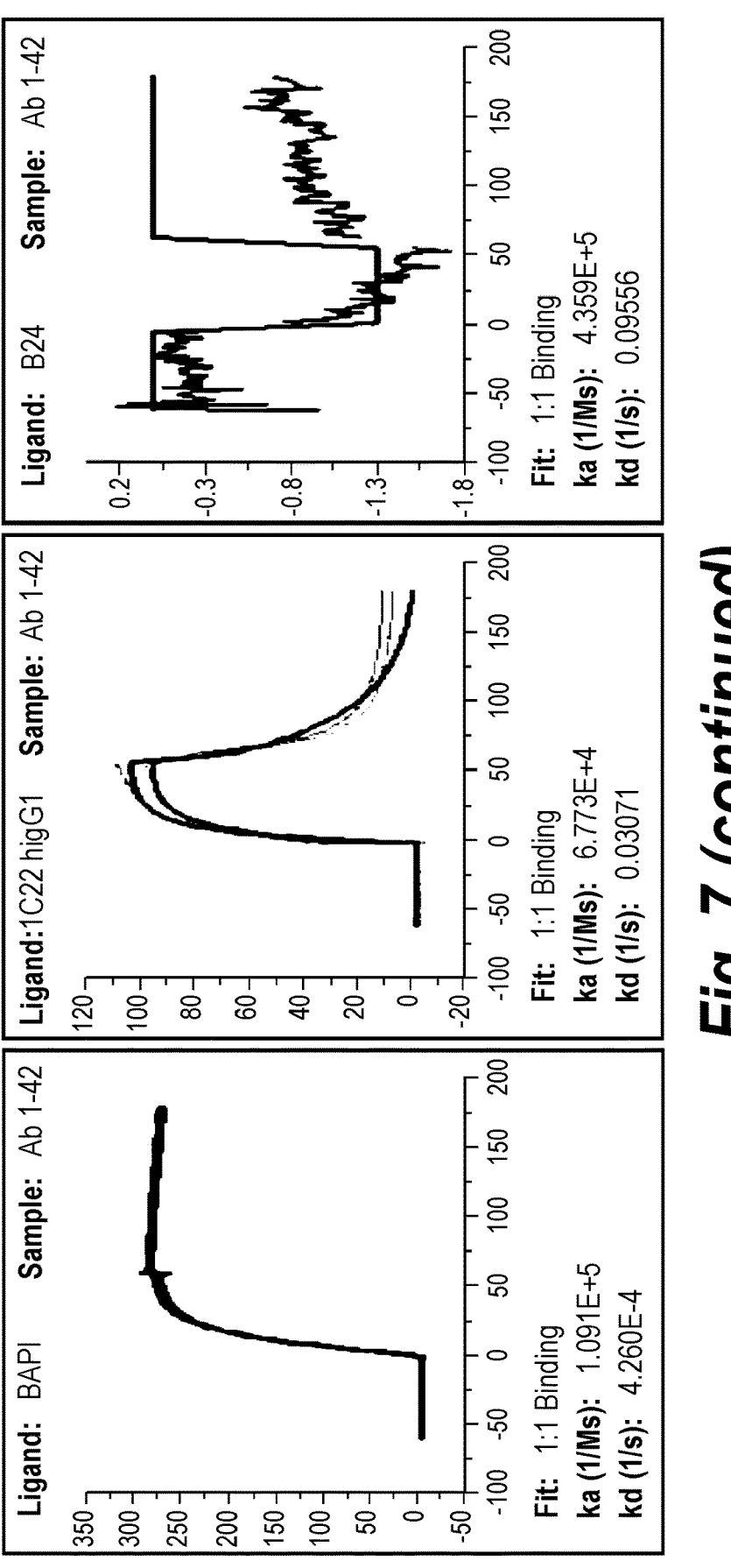
Figure 7:
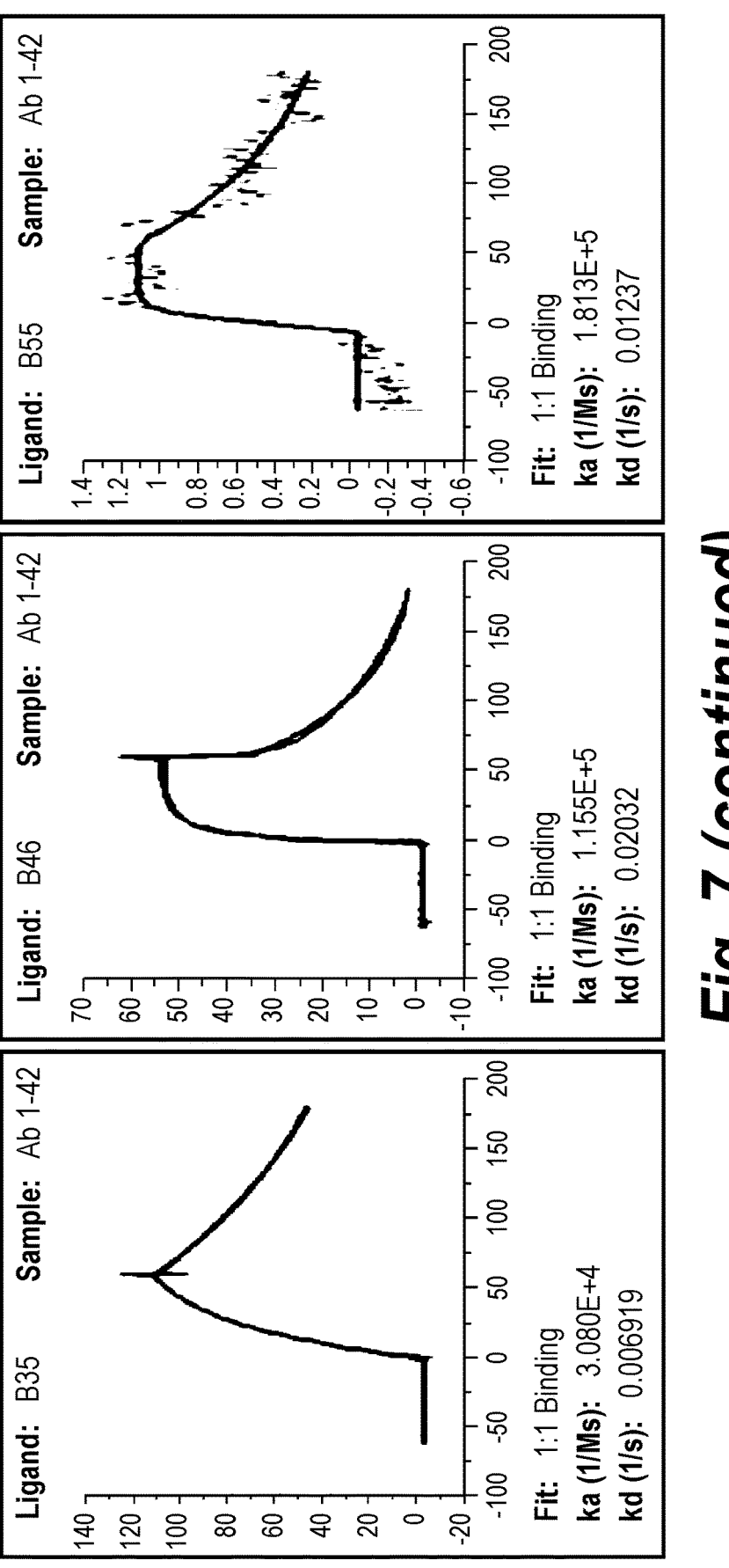
Figure 7:
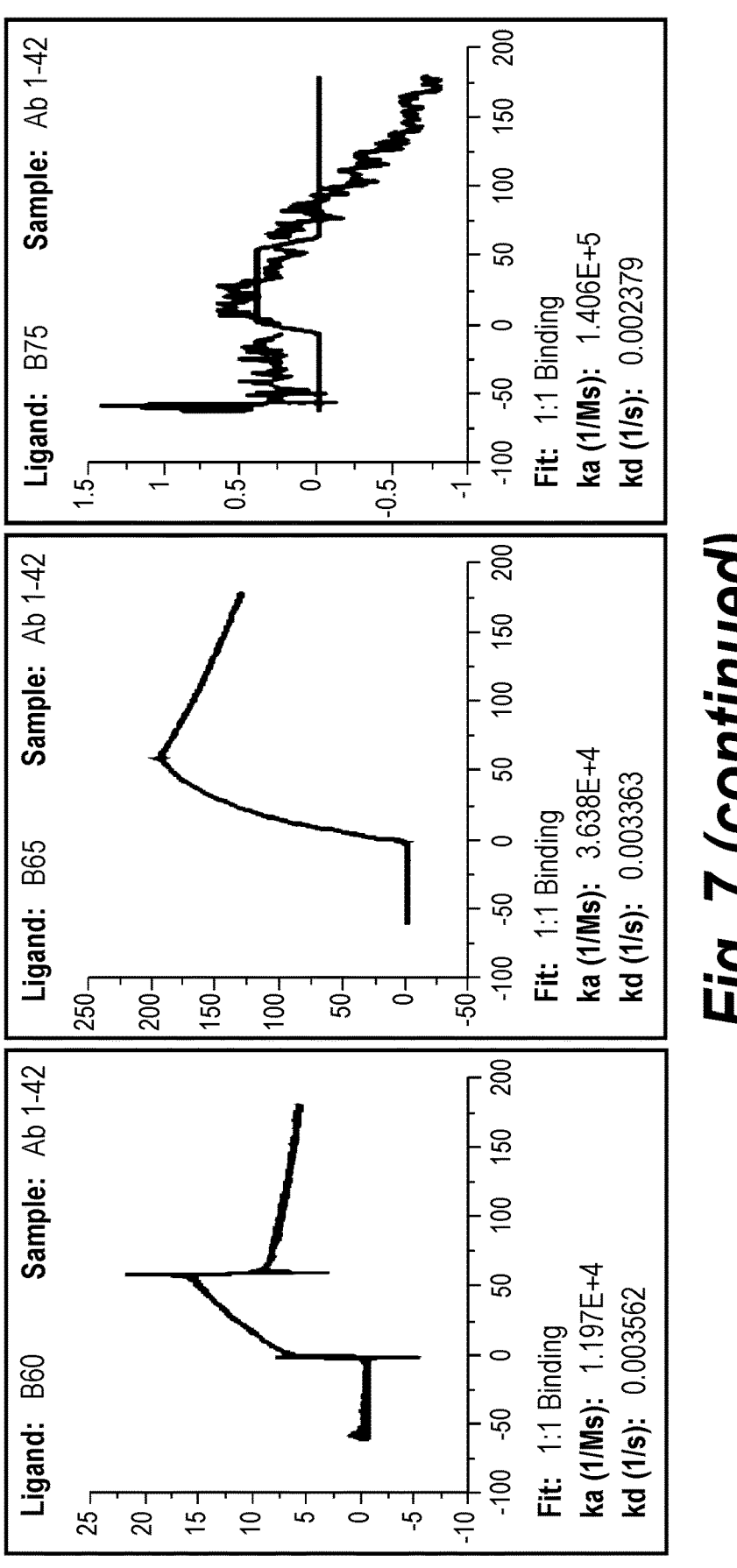
Figure 7:
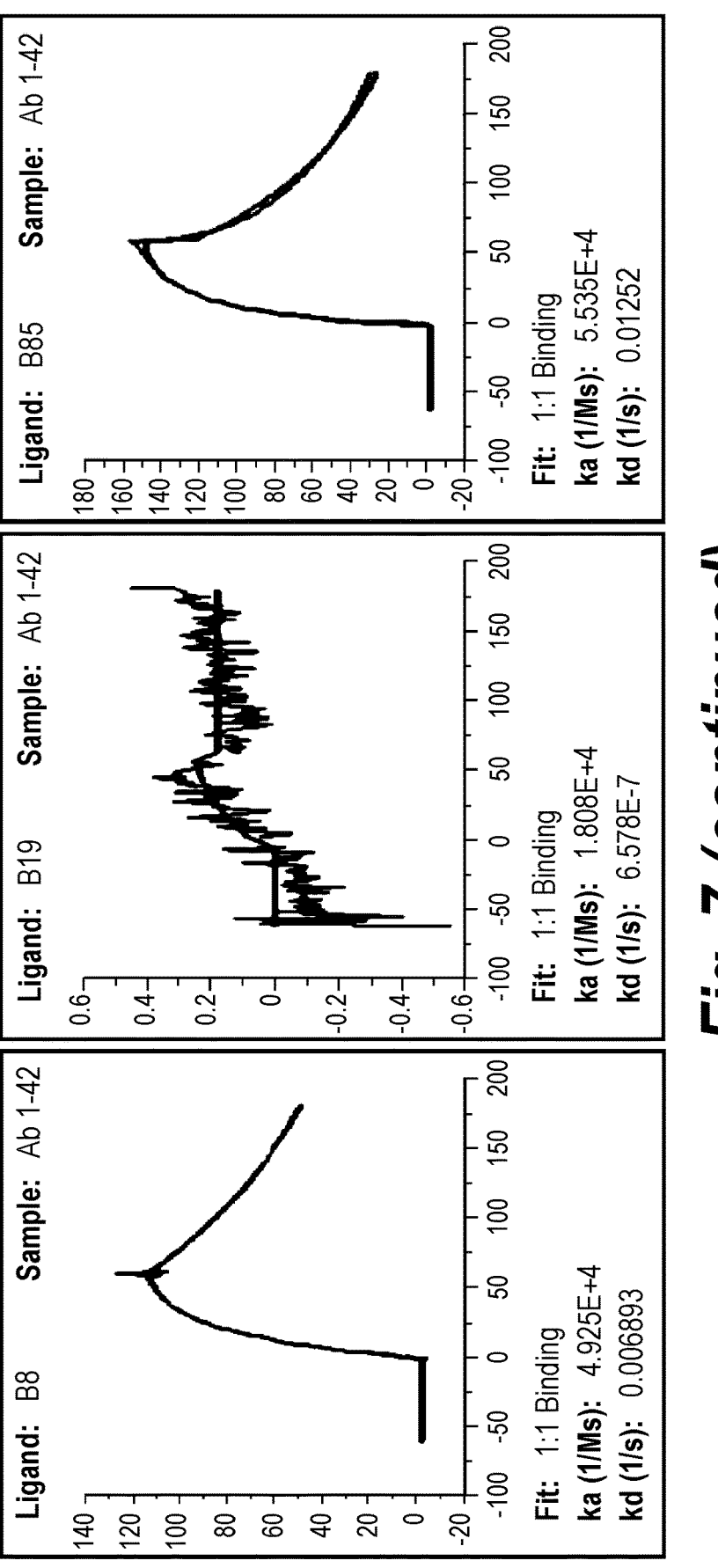
Figure 7:
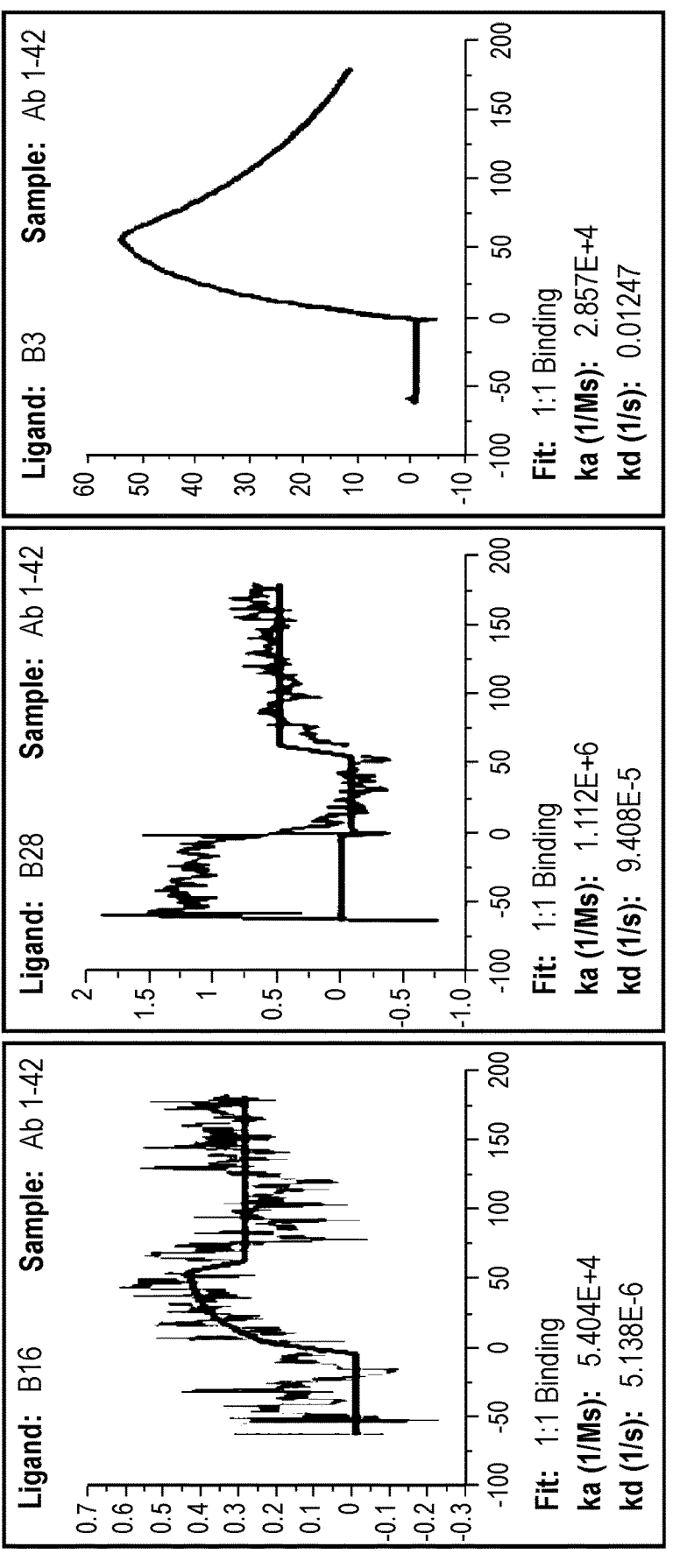
Figure 13:
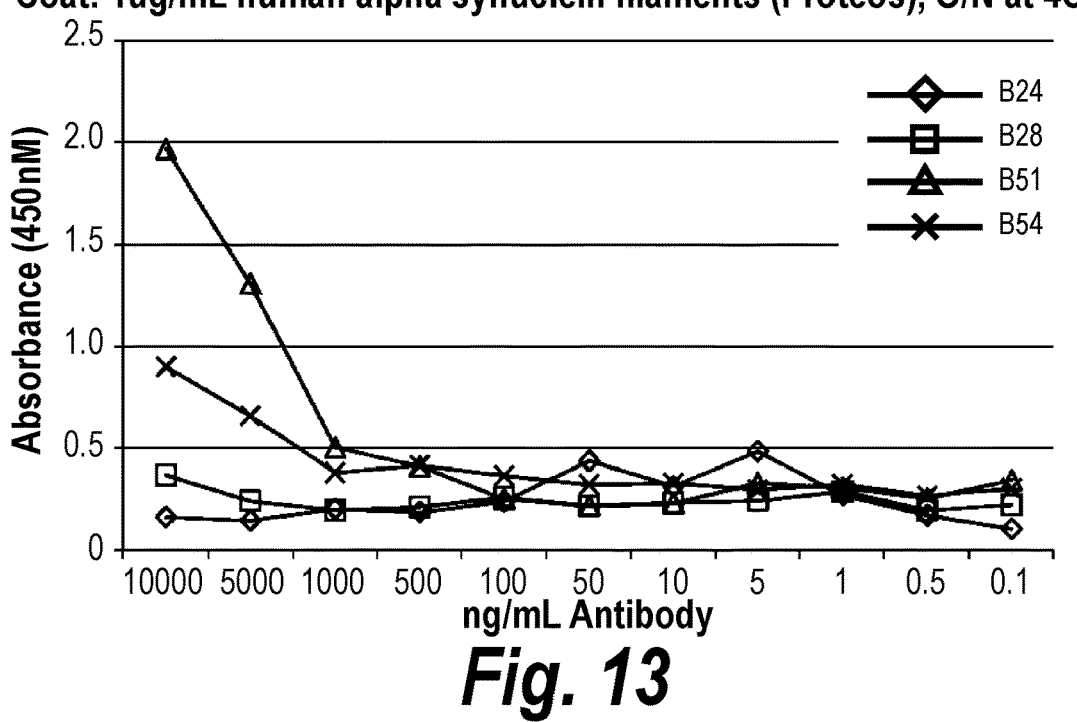
FIG. 13 graphically depicts counter-screening using aggregated alpha-synuclein with FusB clones.
Figure 14:
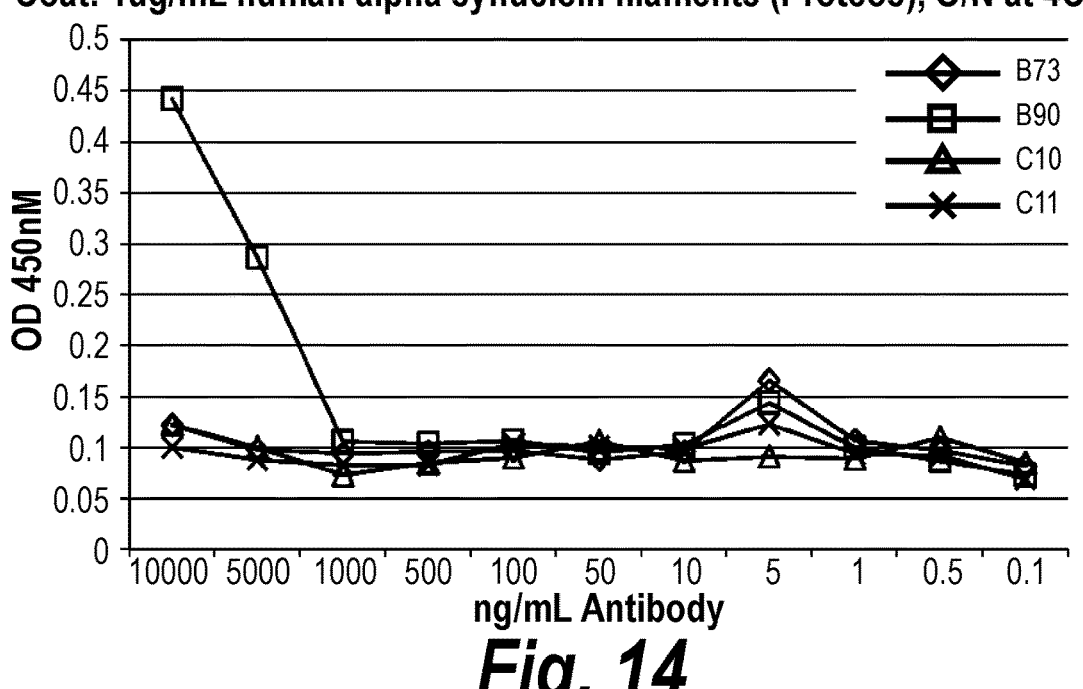
FIG. 14 graphically depicts counter-screening using aggregated alpha-synuclein with FusB clones.
Figure 15:
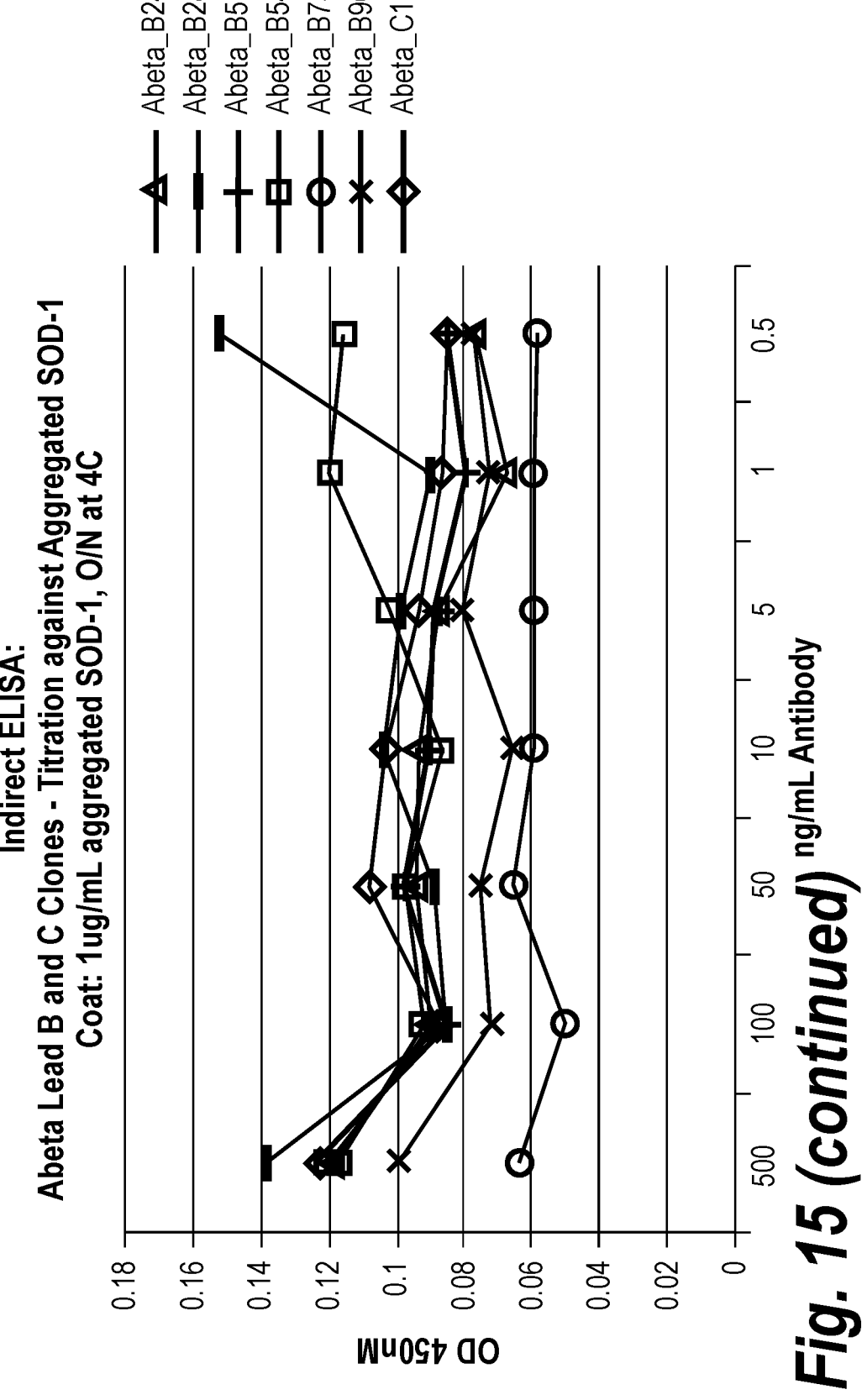
FIG. 15 graphically depicts a SOD-1 counter-screen of FusB clones at 500 ng/ml to 0.5 ng-ml.
Figure 16:
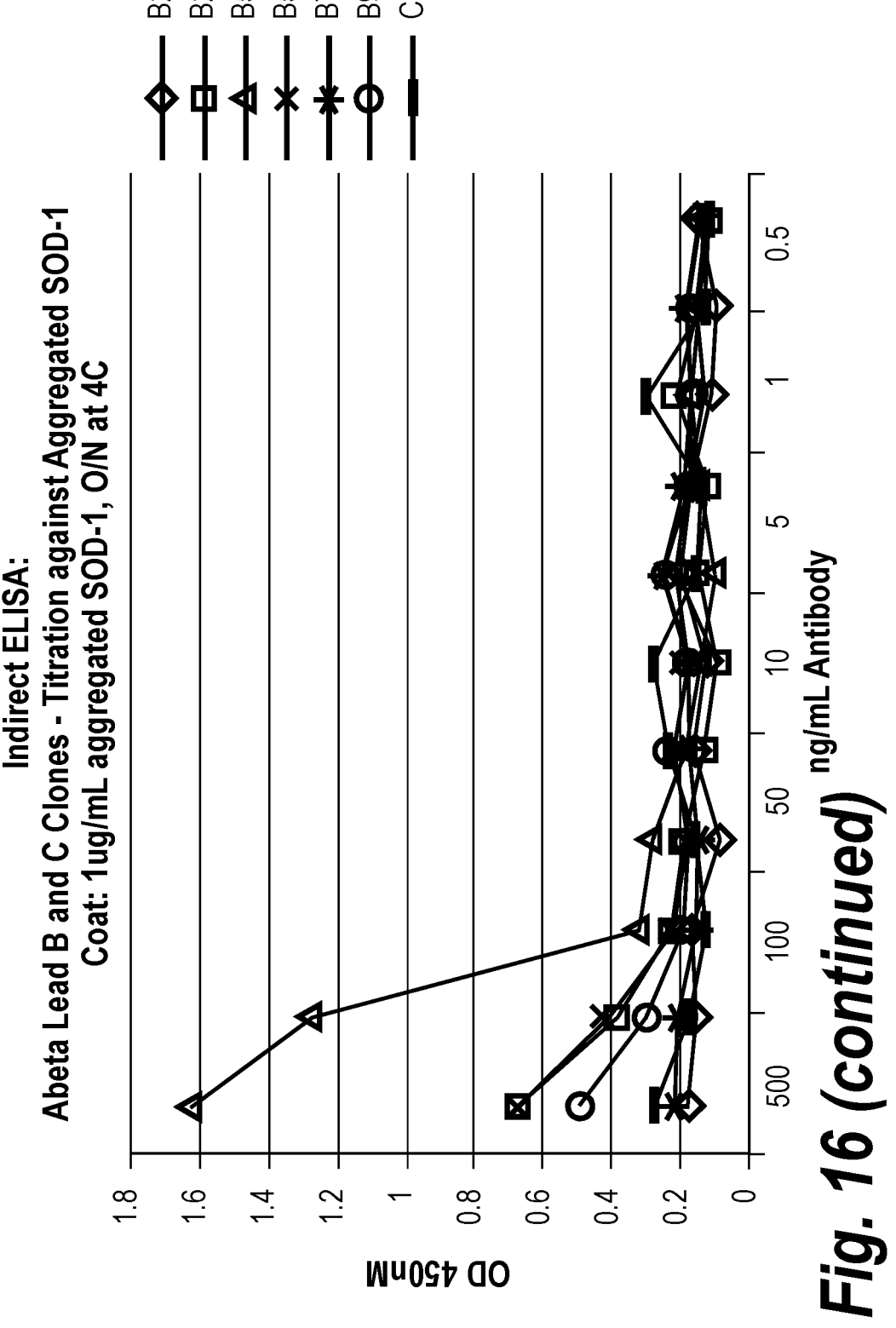
FIG. 16 graphically depicts a SOD-1 counter-screen of FusB clones at 10,000 ng/ml to 100 ng-ml.

The present disclosure provides novel binding polypeptides (e.g., antibodies) that bind to an epitope present in one or more species of soluble, synaptotoxic Aβ. Importantly, the novel binding polypeptides described herein have reduced binding to Aβ, protofibrillar Aβ and/or fibrillar Aβ compared to antibodies known in the art or do not bind monomeric Aβ, protofibrillar Aβ and/or fibrillar Aβ.

In certain embodiments, the novel binding polypeptides described herein prevent or reduce the formation of higher-order, synaptotoxic forms of Aβ, such as monomeric Aβ, protofibrillar Aβ and fibrillar Aβ. In certain embodiments, the novel binding polypeptides described herein prevent or reduce soluble, synaptotoxic Aβ from forming higher-order, synaptotoxic forms of Aβ, such as monomeric Aβ, protofibrillar Aβ and/or fibrillar Aβ.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2$^{nd}$ edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "polypeptide" refers to any polymeric chain of amino acids and encompasses native or artificial proteins, polypeptide analogs or variants of a protein sequence, or fragments thereof, unless otherwise contradicted by context. A polypeptide may be monomeric or polymeric. A polypeptide fragment comprises at least about 5 contiguous amino acids, at least about 10 contiguous amino acids, at least about 15 contiguous amino acids, or at least about 20 contiguous amino acids, for example.

The term "isolated protein" or "isolated polypeptide" refers to a protein or polypeptide that by virtue of its origin or source of derivation is not associated with naturally associated components that accompany it in its native state; is substantially free of other proteins from the same species; is expressed by a cell from a different species; or does not occur in nature. Thus, a protein or polypeptide that is chemically synthesized or synthesized in a cellular system different from the cell from which it naturally originates will be "isolated" from its naturally associated components. A protein or polypeptide may also be rendered substantially free of naturally associated components by isolation using protein purification techniques well known in the art.

As used herein, the term "binding protein" or "binding polypeptide" shall refer to a protein or polypeptide (e.g., an antibody or immunoadhesin) that contains at least one binding site which is responsible for selectively binding to a target antigen of interest (e.g., a human target antigen). Exemplary binding sites include an antibody variable domain, a ligand binding site of a receptor, or a receptor binding site of a ligand. In certain aspects, the binding proteins or binding polypeptides comprise multiple (e.g., two, three, four, or more) binding sites. In certain aspects, the binding protein or binding polypeptide is not a therapeutic enzyme.

The term "ligand" refers to any substance capable of binding, or of being bound, to another substance. Similarly, the term "antigen" refers to any substance to which an antibody may be generated. Although "antigen" is commonly used in reference to an antibody binding substrate, and "ligand" is often used when referring to receptor binding substrates, these terms are not distinguishing, one from the other, and encompass a wide range of overlapping chemical entities. For the avoidance of doubt, antigen and ligand are used interchangeably throughout herein. Antigens/ligands may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and any combination thereof.

The term "specifically binds" as used herein, refers to the ability of an antibody or an immunoadhesin to bind to an antigen with a dissociation constant (Kd) of at most about $1\times10^{-6}$ M, about $1\times10^{-7}$ M, about $1\times10^{-8}$ M, about $1\times10^{-9}$ M, about $1\times10^{-10}$ M, about $1\times10^{-11}$ M, about $1\times10^{-12}$ M or less, and/or to bind to an antigen with an affinity that is at least about two-fold greater than its affinity for a nonspecific antigen.

As used herein, the term "antibody" refers to such assemblies (e.g., intact antibody molecules, immunoadhesins, or variants thereof) which have significant known specific immunoreactive activity to an antigen of interest (e.g. a tumor associated antigen). Antibodies and immunoglobulins comprise light and heavy chains, with or without an inter-chain covalent linkage between them. Basic immunoglobulin structures in vertebrate systems are relatively well-understood.

As used herein, the term "multispecific antibody" denotes an antibody comprising at least two different binding specificities. In one embodiment, a multispecific antibody described herein is specific for two different antigens, e.g., specific for a blood brain barrier (BBB) receptor and soluble amyloid beta (Aβ).

As used herein, the term "monospecific antibody" refers to an antibody that has one or more binding sites each of which has the same binding specificity, i.e., the monospecific antibody binds to a single antigen, e.g., soluble amyloid beta (Aβ).

As will be discussed in more detail below, the generic term "antibody" comprises five distinct classes of antibody that can be distinguished biochemically. While all five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Light chains of immunoglobulin are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ), or epsilon (ε), with some subclasses among them (e.g., γ1-γ4). It is the nature of this chain that determines the "class" of the antibody as IgG, IgM, IgA IgG, or IgE, respectively. The immunoglobulin isotype subclasses (e.g., IgG1, IgG2, IgG3, IgG4, IgA1, etc.) are well-characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarity determining regions" or "CDRs" interspersed among "framework regions" or "FRs," as defined herein.

The regions of an immunoglobulin heavy or light chain may be defined as "constant" (C) region or "variable" (V) regions, based on a relative lack of sequence variation within the regions of various class members in the case of a "constant region," or based on a significant variation within the regions of various class members in the case of a "variable regions." The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, trans-placental mobility, Fc receptor binding, complement binding, and the like. The subunit structures and three-dimensional configurations of the constant regions of the various immunoglobulin classes are well-known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or an intra-chain disulfide bond. Constant region domains on the light chain of an immunoglobulin are referred to interchangeably as "light chain constant region domains," "CL regions" or "CL domains." Constant domains on the heavy chain (e.g., hinge, CH1, CH2 or CH3 domains) are referred to interchangeably as "heavy chain constant region domains," "CH" region domains or "CH domains." Variable domains on the light chain are referred to interchangeably as "light chain variable region domains," "VL region domains" or "VL domains." Variable domains on the heavy chain are referred to interchangeably as "heavy chain variable region domains," "VH region domains" or "VH domains."

By convention, the numbering of the amino acids of the variable constant region domains increases as they become more distal from the antigen-binding site or amino-terminus of the immunoglobulin or antibody. The N-terminus of each heavy and light immunoglobulin chain is a variable region and the C-terminus is a constant region. The CH3 and CL domains comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

The assignment of amino acids to each variable region domain is in accordance with the definitions of Kabat, Sequences of Proteins of Immunological Interest (National Institutes of Health, Bethesda, MD, 1987 and 1991). Kabat also provides a widely used numbering convention (Kabat numbering) in which corresponding residues between different heavy chain variable regions or between different light chain variable regions are assigned the same number. CDRs 1, 2 and 3 of a VL domain are also referred to herein, respectively, as CDR-L1, CDR-L2 and CDR-L3. CDRs 1, 2 and 3 of a VH domain are also referred to herein, respectively, as CDR-H1, CDR-H2 and CDR-H3. If so noted, the assignment of CDRs can be in accordance with IMGT® (Lefranc et al., Developmental & Comparative Immunology 27:55-77; 2003) in lieu of Kabat. Numbering of the heavy chain constant region is via the EU index as set forth in Kabat (Kabat, Sequences of Proteins of Immunological Interest, National Institutes of Health, Bethesda, MD, 1987 and 1991).

As used herein, the term "VH domain" includes the amino terminal variable domain of an immunoglobulin heavy chain, and the term "VL domain" includes the amino terminal variable domain of an immunoglobulin light chain.

As used herein, the term "CH1 domain" includes the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule, and does not form a part of the Fc region of an immunoglobulin heavy chain.

As used herein, the term "hinge region" includes the portion of a heavy chain molecule that joins the CH1 domain to the CH2 domain. The hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about positions 244-360 in the Kabat numbering system (EU positions 231-340). The CH2 domain is unique in that it is not closely paired with another domain. Rather, two N-linked branched carbohydrate chains are interposed between the two CH2 domains of an intact native IgG molecule. In one embodiment, a binding polypeptide of the current disclosure comprises a CH2 domain derived from an IgG1 molecule (e.g. a human IgG1 molecule).

As used herein, the term "CH3 domain" includes the portion of a heavy chain immunoglobulin molecule that extends approximately 110 residues from N-terminus of the CH2 domain, e.g., from about positions 361-476 of the Kabat numbering system (EU positions 341-445). The CH3 domain typically forms the C-terminal portion of the antibody. In some immunoglobulins, however, additional domains may extend from the CH3 domain to form the C-terminal portion of the molecule (e.g., the CH4 domain in the μ chain of IgM and the e chain of IgE). In one embodiment, a binding polypeptide of the current disclosure comprises a CH3 domain derived from an IgG1 molecule (e.g., a human IgG1 molecule).

As used herein, the term "CL domain" includes the constant region domain of an immunoglobulin light chain that extends, e.g., from about Kabat position 107A to about Kabat position 216. The CL domain is adjacent to the VL domain. In one embodiment, a binding polypeptide of the current disclosure comprises a CL domain derived from a kappa light chain (e.g., a human kappa light chain).

As used herein, the term "Fc region" is defined as the portion of a heavy chain constant region beginning in the hinge region just upstream of the papain cleavage site (i.e., residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The term "native Fc" or "wild-type Fc," as used herein, refers to a molecule comprising the sequence of a non-antigen-binding fragment resulting from digestion of an antibody or produced by other means, whether in monomeric or multimeric form, and can contain the hinge region. The original immunoglobulin source of the native Fc is typically of human origin and can be any of the immunoglobulins, such as IgG1 and IgG2. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc," as used herein, is generic to the monomeric, dimeric, and multimeric forms.

The term "Fc variant" or "modified Fc," as used herein, refers to a molecule or sequence that is modified from a native/wild-type Fc but still comprises a binding site for the FcRn. Thus, the term "Fc variant" can comprise a molecule or sequence that is humanized from a non-human native Fc. Furthermore, a native Fc comprises regions that can be removed because they provide structural features or biological activities that are not required for the antibody-like binding polypeptides described herein. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" as used herein encompasses native/wild-type Fc and Fc variants and sequences as defined above. As with Fc variants and native Fc molecules, the term "Fc domain" includes molecules in monomeric or multimeric form, whether digested from whole antibody or produced by other means.

As indicated above, the variable regions of an antibody allow it to selectively recognize and specifically bind epitopes on antigens. That is, the VL domain and VH domain of an antibody combine to form the variable region (Fv) that defines a three-dimensional antigen binding site. This quaternary antibody structure forms the antigen binding site present at the end of each arm of the Y. More specifically, the antigen binding site is defined by three complementary determining regions (CDRs) on each of the heavy and light chain variable regions. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. An antigen binding site is formed by variable regions that vary from one antibody to another. The altered antibodies of the current disclosure comprise at least one antigen binding site.

In certain embodiments, binding polypeptides of the current disclosure comprise at least two antigen binding domains that provide for the association of the binding polypeptide with the selected antigen. The antigen binding domains need not be derived from the same immunoglobulin molecule. In this regard, the variable region may or be derived from any type of animal that can be induced to mount a humoral response and generate immunoglobulins against the desired antigen. As such, the variable region of a binding polypeptide may be, for example, of mammalian origin e.g., may be human, murine, rat, goat, sheep, non-human primate (such as cynomolgus monkeys, macaques, etc.), lupine, or camelid (e.g., from camels, llamas and related species).

In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to the immunoreactive antigen epitope.

Exemplary binding polypeptides include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multispecific antibodies (e.g., bi-specific, tri-specific, etc.) altered to bind to two or more different antigens or to different epitopes on a single antigen); heavy chain molecules joined to scFv molecules and the like. In addition, the term "antibody variant" includes multivalent antibodies (e.g., trivalent, tetravalent, etc., antibodies that bind to three, four or more copies of the same antigen. An "antibody variant" can be multispecific and/or multivalent.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding polypeptides typically has at least one binding site specific for a human antigen molecule.

The term "specificity" refers to the ability to specifically bind (e.g., immunoreact with) a given target antigen (e.g., a human target antigen). A binding polypeptide may be mono-specific and contain one or more binding sites which specifically bind a target or a polypeptide may be multi-specific and contain two or more binding sites which specifically bind the same or different targets. In certain embodiments, a binding polypeptide is specific for two different (e.g., non-overlapping) portions of the same target. In certain embodiments, a binding polypeptide is specific for more than one target.

In certain exemplary embodiments, a binding peptide described herein (e.g., an antibody) specifically binds one or more synaptotoxic forms of Aβ. In certain exemplary embodiments, a binding peptide described herein (e.g., an antibody) that specifically binds one or more synaptotoxic forms of Aβ does not have specificity for one or any combination of monomeric Aβ, fibrillar Aβ, or protofibrillar Aβ. In certain exemplary embodiments, a binding peptide described herein (e.g., an antibody) that specifically binds one or more synaptotoxic forms of Aβ does not have specificity for one or more non-Aβ aggregates, such as, e.g., SOD-1 and/or aggregated synuclein.

In certain exemplary embodiments, a binding peptide described herein (e.g., an antibody) that specifically binds one or more synaptotoxic forms of Aβ prevents and/or reduces one or more symptoms associated with AD. As used herein, "symptoms associated with Alzheimer's disease" or "symptoms associated with AD" refers to signs associated with any of the pre-clinical, mild, moderate or severe stages of AD. Symptoms associated with AD include one or more physical changes, e.g., changes in the brain, including but not limited to: neurotoxicity and/or synaptotoxicity, e.g., in the entorhinal cortex, the hippocampus and the cerebral cortex; accumulation of glial cells; accumulation of Aβ; accumulation of tau; formation of Aβ oligomers; formation of Aβ paranuclei; formation of Aβ protofibrils; formation of mature Aβ fibrils; formation of amyloid plaques; formation of neurofibrillary tangles; chronic inflammation; reduced blood flow to the brain; breakdown of the BBB; brain atrophy, and the like.

Symptoms associated with mild AD include, but are not limited to: memory loss; poor judgment leading to bad decisions; loss of spontaneity and sense of initiative; taking longer to complete normal daily tasks; repeating questions; trouble handling money and paying bills; wandering and getting lost; losing things or misplacing them in odd places; mood and personality changes; increased anxiety and/or aggression, and the like.

Symptoms associated with moderate AD include, but are not limited to: increased memory loss and confusion; inability to learn new things; difficulty with language and problems with reading, writing, and working with numbers; difficulty organizing thoughts and thinking logically; shortened attention span; problems coping with new situations; difficulty carrying out multistep tasks, such as getting dressed; problems recognizing family and friends; hallucinations, delusions, and paranoia; impulsive behavior such as undressing at inappropriate times or places or using vulgar language; inappropriate outbursts of anger; restlessness, agitation, anxiety, tearfulness, wandering-especially in the late afternoon or evening; repetitive statements or movement, occasional muscle twitches, and the like.

Symptoms associated with severe AD include, but are not limited to: memory loss; poor judgment leading to bad decisions; loss of spontaneity and sense of initiative; taking longer to complete normal daily tasks; repeating questions; trouble handling money and paying bills; wandering and getting lost; losing things or misplacing them in odd places; mood and personality changes; increased anxiety and/or aggression, and the like.

As used herein, a "synaptotoxic form of amyloid beta," "synaptotoxic form of Aβ" or "synaptotoxic Aβ" refers to a form of Aβ that is present in soluble brain extract from AD brains and is associated with synapse loss. Synaptotoxic Aβ has a molecular weight of between about 8 kD and about 100 kD and is labile.

According to certain aspects, binding polypeptides are provided herein that specifically bind synaptotoxic Aβ. Full-length heavy chain and light chain sequences of exemplary binding peptides described herein are set forth in Table 1.

TABLE 1

| Full-length heavy chain sequences and light chain sequences of exemplary binding peptides. | | |
|---|---|---|
| clone | Full-length light chain sequence | Full-length heavy chain sequence |
| B24 | EIVMTQSPATLSLSPGERATLSCRASQS VSSSYFSWYQQKPGQAPRLLIYGASTR ATGIPARFSGSGSGTDFTLTISSLQPED FAVYYCQQDSNLPLTFGGGTKVEIKRTV AAPSVFIFPPSDEQLKSGTASVVCLLNN FYPREAKVQWKVDNALQSGNSQESVT EQDSKDSTYSLSSTLTLSKADYEKHKVY ACEVTHQGLSSPVTKSFNRGEC (SEQ ID NO: 65) | EVQLLESGGGLVQPGGSLRLSCAASGF TFSSYAMTWVRQAPGEGLEWVSTISGS GIRTYYADSVKGRFTISRDNSKNTMYLQ MNSLRAEDTAVYYCAKDGLTGDRRWY FDLWGRGTLVTVSSASTKGPSVFPLAP SSKSTSGGTAALGCLVKDYFPEPVTVS WNSGALTSGVHTFPAVLQSSGLYSLSS VVTVPSSSLGTQTYICNVNHKPSNTKVD KKVEPKSCDKTHTCPPCPAPEAAGGPS VFLFPPKPKDTLMISRTPEVTCVVVDVS HEDPEVKFNWYVDGVEVHNAKTKPRE EQYNSTYRVVSVLTVLHQDWLNGKEYK CKVSNKALPAPIEKTISKAKGQPREPQV YTLPPSRDELTKNQVSLTCLVKGFYPSD IAVEWESNGQPENNYKTTPPVLDSDGS FFLYSKLTVDKSRWQQGNVFSCSVMH EALHNHYTQKSLSLSPG (SEQ ID NO: 66) |
| B28 | AIQMTQSPSSLSASVGDRVTITCRASQG IRNDLGWFQQKPGKAPKLLIYPASSLQS GVPSRFSGSGSDTDFTLTISSLQPEDFA TYYCLQDYNFPFTFGPGTKVDIKRTVAA PSVFIFPPSDEQLKSGTASVVCLLNNFY PREAKVQWKVDNALQSGNSQESVTEQ DSKDSTYSLSSTLTLSKADYEKHKVYAC EVTHQGLSSPVTKSFNRGEC (SEQ ID NO: 67) | QVQLVESGGGVVQPGRSVRLSCAATG FTFSSYGMHWVRQAPGKGLEWVAVIW FDGSNEYYADSVRGRFTISRDNSKNTL YLQMNSLRAEDTAVYYCARRGRVGVT RNYYYYNMDVWGQGTTVTVSSASTKG PSVFPLAPSSKSTSGGTAALGCLVKDYF PEPVTVSWNSGALTSGVHTFPAVLQSS GLYSLSSVVTVPSSSLGTQTYICNVNHK PSNTKVDKKVEPKSCDKTHTCPPCPAP EAAGGPSVFLFPPKPKDTLMISRTPEVT CVVVDVSHEDPEVKFNWYVDGVEVHN AKTKPREEQYNSTYRVVSVLTVLHQDW LNGKEYKCKVSNKALPAPIEKTISKAKG QPREPQVYTLPPSRDELTKNQVSLTCL VKGFYPSDIAVEWESNGQPENNYKTTP PVLDSDGSFFLYSKLTVDKSRWQQGNV FSCSVMHEALHNHYTQKSLSLSPG (SEQ ID NO: 68) |
| B51 | AIQMTQSPSSLSASVGDRVTITCRASQG IRNDLGWFQQKPVKAPKLLIYPASSLQS GVPSRFSGSGSGTDFTLTISSLQPEDFA TYYCLQDYNYPWTFGQGTKVEIKRTVA APSVFIFPPSDEQLKSGTASVVCLLNNF YPREAKVQWKVDNALQSGNSQESVTE QDSKDSTYSLSSTLTLSKADYEKHKVYA CEVTHQGLSSPVTKSFNRGEC (SEQ ID NO: 69) | QVQLVESGGGVVQPGRSLRLSCAASG FTFSSHGMHWVRQAPGKGLEWVAVIW YDGSNKNYADSVKGRFTISRDNSKNTL YLQMNSLRAEDTAVYYCARRGRVGVT RNYYYYGMDVWGQGTTVTVSSASTKG PSVFPLAPSSKSTSGGTAALGCLVKDYF PEPVTVSWNSGALTSGVHTFPAVLQSS GLYSLSSVVTVPSSSLGTQTYICNVNHK PSNTKVDKKVEPKSCDKTHTCPPCPAP EAAGGPSVFLFPPKPKDTLMISRTPEVT CVVVDVSHEDPEVKFNWYVDGVEVHN AKTKPREEQYNSTYRVVSVLTVLHQDW LNGKEYKCKVSNKALPAPIEKTISKAKG QPREPQVYTLPPSRDELTKNQVSLTCL VKGFYPSDIAVEWESNGQPENNYKTTP PVLDSDGSFFLYSKLTVDKSRWQQGNV FSCSVMHEALHNHYTQKSLSLSPG (SEQ ID NO: 70) |
| B54 | AIQMTQSPSSLSASVGDRVTITCRTSQD IRNDLGWFQQKPGKAPKFLIYPASSLQG GVPSRFSGSGSGTDFILTISSLQPEDFA TYYCLQDYNFPWTFGEGTKVEIKRTVA APSVFIFPPSDEQLKSGTASVVCLLNNF YPREAKVQWKVDNALQSGNSQESVTE QDSKDSTYSLSSTLTLSKADYEKHKVYA CEVTHQGLSSPVTKSFNRGEC (SEQ ID NO: 71) | QVQLVESGGGVVQPGRSLRLSCAASG FTFSTYGMHWVRQAPGKGLEWVALIW YDGSKKYYADSVQGRFTISRDSSKNTL YLQMNSLRVEDTAVYYCARRGRVGVT RNYYYYGMDVWGQGTTVTVSSASTKG PSVFPLAPSSKSTSGGTAALGCLVKDYF PEPVTVSWNSGALTSGVHTFPAVLQSS GLYSLSSVVTVPSSSLGTQTYICNVNHK PSNTKVDKKVEPKSCDKTHTCPPCPAP EAAGGPSVFLFPPKPKDTLMISRTPEVT |

TABLE 1-continued

Full-length heavy chain sequences and light chain sequences of exemplary
binding peptides.

| clone | Full-length light chain sequence | Full-length heavy chain sequence |
|---|---|---|
| | | CVVVDVSHEDPEVKFNWYVDGVEVHN<br>AKTKPREEQYNSTYRVVSVLTVLHQDW<br>LNGKEYKCKVSNKALPAPIEKTISKAKG<br>QPREPQVYTLPPSRDELTKNQVSLTCL<br>VKGFYPSDIAVEWESNGQPENNYKTTP<br>PVLDSDGSFFLYSKLTVDKSRWQQGNV<br>FSCSVMHEALHNHYTQKSLSLSPG<br>(SEQ ID NO: 72) |
| B73 | QAVVTQESALTTSPGGTVILTCRSSTGA<br>VTTSNYANWVQEKPDHLFTGLIGETNN<br>RAPGVPVRFSGSLIGDKAALTITGAQTE<br>DDAMYFCALWYSTHWVFGGGTKLTVL<br>GQPKAAPSVTLFPPSSEELQANKATLVC<br>LISDFYPGAVTVAWKADSSPVKAGVETT<br>TPSKQSNNKYAASSYLSLTPEQWKSHR<br>SYSCQVTHEGSTVEKTVAPTECS<br>(SEQ ID NO: 73) | QLQLQMSGPGLVKPSETLSLTCTVSGG<br>SISSSSYYWGWIRQSPGKGLEWIGSIYY<br>SGRTYYNPSLKSRVTISVDTSKNQFSLK<br>LSSVTAADTAMYYCARRSSGRPYYWG<br>QGTLVTVSSASTKGPSVFPLAPSSKSTS<br>GGTAALGCLVKDYFPEPVTVSWNSGAL<br>TSGVHTFPAVLQSSGLYSLSSVVTVPSS<br>SLGTQTYICNVNHKPSNTKVDKKVEPKS<br>CDKTHTCPPCPAPEAAGGPSVFLFPPK<br>PKDTLMISRTPEVTCVVVDVSHEDPEVK<br>FNWYVDGVEVHNAKTKPREEQYNSTY<br>RVVSVLTVLHQDWLNGKEYKCKVSNKA<br>LPAPIEKTISKAKGQPREPQVYTLPPSR<br>DELTKNQVSLTCLVKGFYPSDIAVEWES<br>NGQPENNYKTTPPVLDSDGSFFLYSKL<br>TVDKSRWQQGNVFSCSVMHEALHNHY<br>TQKSLSLSPG (SEQ ID NO: 74) |
| B75 | EIVMTQSPATLSVSPGEKATLSCRASQS<br>FSSNLAWYQQKPGQAPRLLIYGASTRA<br>TGIPARFSGSGSGTEFTLTISSLQSEDFA<br>VYYCQQYNNWPYTFGQGTKLEIKRTVA<br>APSVFIFPPSDEQLKSGTASVVCLLNNF<br>YPREAKVQWKVDNALQSGNSQESVTE<br>QDSKDSTYSLSSTLTLSKADYEKHKVYA<br>CEVTHQGLSSPVTKSFNRGEC<br>(SEQ ID NO: 75) | QVQLVESGGGVVQPGRSLRLSCAASG<br>FTFSSYGMHWVRQAPGKGLEWVAVIW<br>YDGSYKYYADSVKGRFTISRDNSKNTL<br>YLQMNSLRVEDTAVYYCAREGRTYYDF<br>LTGYFDFWGQGTLVTVSSASTKGPSVF<br>PLAPSSKSTSGGTAALGCLVKDYFPEP<br>VTVSWNSGALTSGVHTFPAVLQSSGLY<br>SLSSVVTVPSSSLGTQTYICNVNHKPSN<br>TKVDKKVEPKSCDKTHTCPPCPAPEAA<br>GGPSVFLFPPKPKDTLMISRTPEVTCVV<br>VDVSHEDPEVKFNWYVDGVEVHNAKT<br>KPREEQYNSTYRVVSVLTVLHQDWLNG<br>KEYKCKVSNKALPAPIEKTISKAKGQPR<br>EPQVYTLPPSRDELTKNQVSLTCLVKGF<br>YPSDIAVEWESNGQPENNYKTTPPVLD<br>SDGSFFLYSKLTVDKSRWQQGNVFSCS<br>VMHEALHNHYTQKSLSLSPG<br>(SEQ ID NO: 76) |
| B90 | AIQMTQSPSSLSASVGDRVTITCRASQG<br>IRNDLGWFHQKPGKAPKLLIYAASSLQS<br>GVPSRFSGSGSGTDFTLTISSLQPEDFA<br>TYYCLQDYVYPWTFGQGTKVEIKRTVA<br>APSVFIFPPSDEQLKSGTASVVCLLNNF<br>YPREAKVQWKVDNALQSGNSQESVTE<br>QDSKDSTYSLSSTLTLSKADYEKHKVYA<br>CEVTHQGLSSPVTKSFNRGEC<br>(SEQ ID NO: 77) | QVQLVESGGGVVQPGRSLRLSCAASG<br>FTFSSYGMHWVRQAPGKGLEWVAIIWY<br>DGSKKYYADSVKGRFTISRDNSKNTLYL<br>QMNSLRVEDTAVYYCARRGRVGATRD<br>YYYYSMDVWGQGTTVTVSSASTKGPS<br>VFPLAPSSKSTSGGTAALGCLVKDYFPE<br>PVTVSWNSGALTSGVHTFPAVLQSSGL<br>YSLSSVVTVPSSSLGTQTYICNVNHKPS<br>NTKVDKKVEPKSCDKTHTCPPCPAPEA<br>AGGPSVFLFPPKPKDTLMISRTPEVTCV<br>VVDVSHEDPEVKFNWYVDGVEVHNAK<br>TKPREEQYNSTYRVVSVLTVLHQDWLN<br>GKEYKCKVSNKALPAPIEKTISKAKGQP<br>REPQVYTLPPSRDELTKNQVSLTCLVK<br>GFYPSDIAVEWESNGQPENNYKTTPPV<br>LDSDGSFFLYSKLTVDKSRWQQGNVFS<br>CSVMHEALHNHYTQKSLSLSPG<br>(SEQ ID NO: 78) |
| C11 | DIQMTQSPSSLSASVGDRVTITCRASQG<br>IRNDLGWYQQKPGKAPTLLIYAASSLQS<br>GVPSRFSGSGSGTDFTLTISSLQPEDFA<br>TYYCLQDFNYPYTFGQGTKLEIKRTVAA<br>PSVFIFPPSDEQLKSGTASVVCLLNNFY<br>PREAKVQWKVDNALQSGNSQESVTEQ<br>DSKDSTYSLSSTLTLSKADYEKHKVYAC<br>EVTHQGLSSPVTKSFNRGEC<br>(SEQ ID NO: 79) | QVQLQESGPGLVKPSETLSLTCTVSGG<br>SISSYYWSWIRQPPGKGLEWIGSIYYSG<br>TTKYNPSLKSRVTISVGTSKNQFSLKLN<br>SVTAADTAVYYCARDNWGSRFDYWGQ<br>GTLVTVSSASTKGPSVFPLAPSSKSTSG<br>GTAALGCLVKDYFPEPVTVSWNSGALT<br>SGVHTFPAVLQSSGLYSLSSVVTVPSSS<br>LGTQTYICNVNHKPSNTKVDKKVEPKS<br>CDKTHTCPPCPAPEAAGGPSVFLFPPK<br>PKDTLMISRTPEVTCVVVDVSHEDPEVK |

TABLE 1-continued

Full-length heavy chain sequences and light chain sequences of exemplary
binding peptides.

| clone | Full-length light chain sequence | Full-length heavy chain sequence |
|---|---|---|
| | | FNWYVDGVEVHNAKTKPREEQYNSTY RVVSVLTVLHQDWLNGKEYKCKVSNKA LPAPIEKTISKAKGQPREPQVYTLPPSR DELTKNQVSLTCLVKGFYPSDIAVEWES NGQPENNYKTTPPVLDSDGSFFLYSKL TVDKSRWQQGNVFSCSVMHEALHNHY TQKSLSLSPG (SEQ ID NO: 80) |

The light chain variable region (LCVR) sequences and the heavy chain variable region (HCVR) sequences of exemplary binding peptides described herein are set forth in Table 2.

TABLE 2 heavy chain variable region sequences and light chain variable region sequences
of exemplary binding peptides.

| clone | light chain variable region (LCVR) sequences | heavy chain variable region (HCVR) sequences |
|---|---|---|
| B24 | EIVMTQSPATLSLSPGERATLSCRASQ SVSSSYFSWYQQKPGQAPRLLIYGAS TRATGIPARFSGSGSGTDFTLTISSLQ PEDFAVYYCQQDSNLPLTFGGGTKVE IK (SEQ ID NO: 1) | EVQLLESGGGLVQPGGSLRLSCAASGFTF SSYAMTWVRQAPGEGLEWVSTISGSGIRT YYADSVKGRFTISRDNSKNTMYLQMNSLR AEDTAVYYCAKDGLTGDRRWYFDLWGRG TLVTVSS (SEQ ID NO: 2) |
| B28 | AIQMTQSPSSLSASVGDRVTITCRASQ GIRNDLGWFQQKPGKAPKLLIYPASSL QSGVPSRFSGSGSDTDFTLTISSLQP EDFATYYCLQDYNFPFTFGPGTKVDIK (SEQ ID NO: 3) | QVQLVESGGGVVQPGRSVRLSCAATGFT FSSYGMHWVRQAPGKGLEWVAVIWFDGS NEYYADSVRGRFTISRDNSKNTLYLQMNS LRAEDTAVYYCARRGRVGVTRNYYYYNM DVWGQGTTVTVSS (SEQ ID NO: 4) |
| B51 | AIQMTQSPSSLSASVGDRVTITCRASQ GIRNDLGWFQQKPVKAPKLLIYPASSL QSGVPSRFSGSGSGTDFTLTISSLQP EDFATYYCLQDYNYPWTFGQGTKVEI K (SEQ ID NO: 5) | QVQLVESGGGVVQPGRSLRLSCAASGFT FSSHGMHWVRQAPGKGLEWVAVIWYDG SNKNYADSVKGRFTISRDNSKNTLYLQMN SLRAEDTAVYYCARRGRVGVTRNYYYYG MDVWGQGTTVTVSS (SEQ ID NO: 6) |
| B54 | AIQMTQSPSSLSASVGDRVTITCRTSQ DIRNDLGWFQQKPGKAPKFLIYPASSL QGGVPSRFSGSGSGTDFILTISSLQPE DFATYYCLQDYNFPWTFGEGTKVEIK (SEQ ID NO: 7) | QVQLVESGGGVVQPGRSLRLSCAASGFT FSTYGMHWVRQAPGKGLEWVALIWYDGS KKYYADSVQGRFTISRDSSKNTLYLQMNS LRVEDTAVYYCARRGRVGVTRNYYYYGM DVWGQGTTVTVSS (SEQ ID NO: 8) |
| B73 | QAVVTQESALTTSPGGTVILTCRSSTG AVTTSNYANWVQEKPDHLFTGLIGET NNRAPGVPVRFSGSLIGDKAALTITGA QTEDDAMYFCALWYSTHWVFGGGTK LTVL (SEQ ID NO: 9) | QLQLQMSGPGLVKPSETLSLTCTVSGGSI SSSSYYWGWIRQSPGKGLEWIGSIYYSGR TYYNPSLKSRVTISVDTSKNQFSLKLSSVT AADTAMYYCARRSSGRPYYWGQGTLVTV SS (SEQ ID NO: 10) |
| B75 | EIVMTQSPATLSVSPGEKATLSCRAS QSFSSNLAWYQQKPGQAPRLLIYGAS TRATGIPARFSGSGSGTEFTLTISSLQ SEDFAVYYCQQYNNWPYTFGQGTKL EIK (SEQ ID NO: 11) | QVQLVESGGGVVQPGRSLRLSCAASGFT FSSYGMHWVRQAPGKGLEWVAVIWYDG YKYYADSVKGRFTISRDNSKNTLYLQMNS LRVEDTAVYYCAREGRTYYDFLTGYFDFW GQGTLVTVSS (SEQ ID NO: 12) |
| B90 | AIQMTQSPSSLSASVGDRVTITCRASQ GIRNDLGWFHQKPGKAPKLLIYAASSL QSGVPSRFSGSGSGTDFTLTISSLQP EDFATYYCLQDYVYPWTFGQGTKVEI K (SEQ ID NO: 13) | QVQLVESGGGVVQPGRSLRLSCAASGFT FSSYGMHWVRQAPGKGLEWVAIIWYDGS KKYYADSVKGRFTISRDNSKNTLYLQMNS LRVEDTAVYYCARRGRVGATRDYYYSM DVWGQGTTVTVSS (SEQ ID NO: 14) |
| C11 | DIQMTQSPSSLSASVGDRVTITCRAS QGIRNDLGWYQQKPGKAPTLLIYAAS SLQSGVPSRFSGSGSGTDFTLTISSLQ PEDFATYYCLQDFNYPYTFGQGTKLEI K (SEQ ID NO: 15) | QVQLQESGPGLVKPSETLSLTCTVSGGSIS SYYWSWIRQPPGKGLEWIGSIYYSGTTKY NPSLKSRVTISVGTSKNQFSLKLNSVTAAD TAVYYCARDNWGSRFDYWGQGTLVTVSS (SEQ ID NO: 16) |

The light chain framework (LFW) sequences and the heavy chain framework (HFW) regions of exemplary binding peptides described herein are set forth in Table 3.

TABLE 3

| | Light chain framework sequences and heavy chain framework sequences of exemplary binding peptides. | |
| --- | --- | --- |
| clone | light chain framework (LFW) sequences | heavy chain framework (HCF) sequences |
| B24 | EIVMTQSPATLSLSPGERATLSCRAS (FW1) (SEQ ID NO: 81) FSWYQQKPGQAPRLLIY (FW2)(SEQ ID NO: 82) TRATGIPARFSGSGSGTDFTLTISSLQPEDFA VYYC (FW3)(SEQ ID NO: 83) FGGGTKVEIK (FW4)(SEQ ID NO: 84) | EVQLLESGGGLVQPGGSLRLSCAAS (FW1)(SEQ ID NO: 85) MTWVRQAPGEGLEWVST (FW2)(SEQ ID NO: 86) YYADSVKGRFTISRDNSKNTMYLQMNSL RAEDTAVYYC (FW3)(SEQ ID NO: 87) WGRGTLVTVSS (FW4)(SEQ ID NO: 88) |
| B28 | AIQMTQSPSSLSASVGDRVTITCRAS (FW1) (SEQ ID NO: 89) LGWFQQKPGKAPKLLIY (FW2)(SEQ ID NO: 90) SLQSGVPSRFSGSGSDTDFTLTISSLQPEDF ATYYC (FW3)(SEQ ID NO: 91) FGPGTKVDIK (FW4)(SEQ ID NO: 92) | QVQLVESGGGVVQPGRSVRLSCAAT (FW1)(SEQ ID NO: 93) MHWVRQAPGKGLEWVAV (FW2)(SEQ ID NO: 94) YYADSVRGRFTISRDNSKNTLYLQMNSLR AEDTAVYYC (FW3)(SEQ ID NO: 95) WGQGTTVTVSS (FW4)(SEQ ID NO: 96) |
| B51 | AIQMTQSPSSLSASVGDRVTITCRAS (FW1) (SEQ ID NO: 97) LGWFQQKPVKAPKLLIY (FW2)(SEQ ID NO: 98) SLQSGVPSRFSGSGSGTDFTLTISSLQPEDF ATYYC (FW3)(SEQ ID NO: 99) FGQGTKVEIK (FW4)(SEQ ID NO: 100) | QVQLVESGGGVVQPGRSLRLSCAAS (FW1)(SEQ ID NO: 101) MHWVRQAPGKGLEWVAV (FW2)(SEQ ID NO: 102) NYADSVKGRFTISRDNSKNTLYLQMNSLR AEDTAVYYC (FW3)(SEQ ID NO: 103) WGQGTTVTVSS (FW4)(SEQ ID NO: 104) |
| B54 | AIQMTQSPSSLSASVGDRVTITCRTS (FW1) (SEQ ID NO: 105) LGWFQQKPGKAPKFLIY (FW2)(SEQ ID NO: 106) SLQSGVPSRFSGSGSGTDFILTISSLQPEDF ATYYC (FW3)(SEQ ID NO: 107) FGEGTKVEIK (FW4)(SEQ ID NO: 108) | QVQLVESGGGVVQPGRSLRLSCAAS (FW1)(SEQ ID NO: 109) MHWVRQAPGKGLEWVAL (FW2)(SEQ ID NO: 110) YYADSVQGRFTISRDSSKNTLYLQMNSLR VEDTAVYYC (FW3)(SEQ ID NO: 111) WGQGTTVTVSS (FW4)(SEQ ID NO: 112) |
| B73 | QAVVTQESALTTSPGGTVILTCRSS (FW1) (SEQ ID NO: 113) ANWVQEKPDHLFTGLIG (FW2)(SEQ ID NO: 114) NRAPGVPVRFSGSLIGDKAALTITGAQTEDD AMYFC (FW3)(SEQ ID NO: 115) FGGGTKLTVL (FW4)(SEQ ID NO: 116) | QLQLQMSGPGLVKPSETLSLTCTVS (FW1)(SEQ ID NO: 117) WGWIRQSPGKGLEWIGS (FW2)(SEQ ID NO: 118) YYNPSLKSRVTISVDTSKNQFSLKLSSVTA ADTAMYYC (FW3)(SEQ ID NO: 119) WGQGTLVTVSS (FW4)(SEQ ID NO: 120) |
| B75 | EIVMTQSPATLSVSPGEKATLSCRAS (FW1) (SEQ ID NO: 121) LAWYQQKPGQAPRLLIY (FW2)(SEQ ID NO: 122) TRATGIPARFSGSGSGTEFTLTISSLQSEDFA VYYC (FW3)(SEQ ID NO: 123) FGQGTKLEIK (FW4)(SEQ ID NO: 124) | QVQLVESGGGVVQPGRSLRLSCAAS (FW1)(SEQ ID NO: 125) MHWVRQAPGKGLEWVAV (FW2)(SEQ ID NO: 126) YYADSVKGRFTISRDNSKNTLYLQMNSLR VEDTAVYYC (FW3)(SEQ ID NO: 127) WGQGTLVTVSS (FW4)(SEQ ID NO: 128) |
| B90 | AIQMTQSPSSLSASVGDRVTITCRAS (FW1) (SEQ ID NO: 129) LGWFHQKPGKAPKLLIY (FW2)(SEQ ID NO: 130) SLQSGVPSRFSGSGSGTDFTLTISSLQPEDF ATYYC (FW3)(SEQ ID NO: 131) FGQGTKVEIK (FW4)(SEQ ID NO: 132) | QVQLVESGGGVVQPGRSLRLSCAAS (FW1)(SEQ ID NO: 133) MHWVRQAPGKGLEWVAI (FW2)(SEQ ID NO: 134) YYADSVKGRFTISRDNSKNTLYLQMNSLR VEDTAVYYC (FW3)(SEQ ID NO: 135) WGQGTTVTVSS (FW4)(SEQ ID NO: 136) |
| C11 | DIQMTQSPSSLSASVGDRVTITCRAS (FW1) (SEQ ID NO: 137) LGWYQQKPGKAPTLLIY (FW2)(SEQ ID NO: 138) SLQSGVPSRFSGSGSGTDFTLTISSLQPEDF ATYYC (FW3)(SEQ ID NO: 139) FGQGTKLEIK (FW4)(SEQ ID NO: 140) | QVQLQESGPGLVKPSETLSLTCTVS (FW1)(SEQ ID NO: 141) WSWIRQPPGKGLEWIGS (FW2)(SEQ ID NO: 142) KYNPSLKSRVTISVGTSKNQFSLKLNSVTA ADTAVYYC (FW3)(SEQ ID NO: 143) WGQGTLVTVSS (FW4)(SEQ ID NO: 144) |

The complementarity determining region (CDR) sequences of the heavy chains and the light chains of exemplary binding peptides described herein are set forth in Table 4.

TABLE 4

Heavy chain CDR sequences and light chain CDR sequences of exemplary binding peptides.

| clone | light chain CDR (LCDR) sequences | heavy chain CDR (HCDR) sequences |
|---|---|---|
| B24 | QSVSSSY (SEQ ID NO: 17), LCDR1<br>GAS (SEQ ID NO: 18), LCDR2<br>QQDSNLPLT (SEQ ID NO: 19), LCDR3 | GFTFSSYA (SEQ ID NO: 20), HCDR1<br>ISGSGIRT (SEQ ID NO: 21), HCDR2<br>AKDGLTGDRRWYFDL (SEQ ID NO: 22), HCDR3 |
| B28 | QGIRND (SEQ ID NO: 23), LCDR1<br>PAS (SEQ ID NO: 24), LCDR2<br>LQDYNFPFT (SEQ ID NO: 25), LCDR3 | GFTFSSYG (SEQ ID NO: 26), HCDR1<br>IWFDGSNE (SEQ ID NO: 27), HCDR2<br>ARRGRVGVTRNYYYYNMDV (SEQ ID NO: 28), HCDR3 |
| B51 | QGIRND (SEQ ID NO: 29), LCDR1<br>PAS (SEQ ID NO: 30), LCDR2<br>LQDYNYPWT (SEQ ID NO: 31), LCDR3 | GFTFSSHG (SEQ ID NO: 32), HCDR1<br>IWYDGSNK (SEQ ID NO: 33), HCDR2<br>ARRGRVGVTRNYYYYGMDV (SEQ ID NO: 34), HCDR3 |
| B54 | QDIRND (SEQ ID NO: 35), LCDR1<br>PAS (SEQ ID NO: 36), LCDR2<br>LQDYNFPWT (SEQ ID NO: 37), LCDR3 | GFTFSTYG (SEQ ID NO: 38), HCDR1<br>IWYDGSKK (SEQ ID NO: 39), HCDR2<br>ARRGRVGVTRNYYYYGMDV (SEQ ID NO: 40), HCDR3 |
| B73 | TGAVTTSNY (SEQ ID NO: 41), LCDR1<br>ETN (SEQ ID NO: 42), LCDR2<br>ALWYSTHWV (SEQ ID NO: 43), LCDR3 | GGSISSSSYY (SEQ ID NO: 44), HCDR1<br>IYYSGRT (SEQ ID NO: 45), HCDR2<br>ARRSSGRPYY (SEQ ID NO: 46), HCDR3 |
| B75 | QSFSSN (SEQ ID NO: 47), LCDR1<br>GAS (SEQ ID NO: 48), LCDR2<br>QQYNNWPYT (SEQ ID NO: 49), LCDR3 | GFTFSSYG (SEQ ID NO: 50), HCDR1<br>IWYDGSYK (SEQ ID NO: 51), HCDR2<br>AREGRTYYDFLTGYFDF (SEQ ID NO: 52), HCDR3 |
| B90 | QGIRND (SEQ ID NO: 53), LCDR1<br>AAS (SEQ ID NO: 54), LCDR2<br>LQDYVYPWT (SEQ ID NO: 55), LCDR3 | GFTFSSYG (SEQ ID NO: 56), HCDR1<br>IWYDGSKK (SEQ ID NO: 57), HCDR2<br>ARRGRVGATRDYYYYSMDV (SEQ ID NO: 58), HCDR3 |
| C11 | QGIRND (SEQ ID NO: 59), LCDR1<br>AAS (SEQ ID NO: 60), LCDR2<br>LQDFNYPYT (SEQ ID NO: 61), LCDR3 | GGSISSYY (SEQ ID NO: 62), HCDR1<br>IYYSGTT (SEQ ID NO: 63), HCDR2<br>ARDNWGSRFDY (SEQ ID NO: 64), HCDR3 |

The term "antigen" or "target antigen," as used herein, refers to a molecule or a portion of a molecule that is capable of being bound by the binding site of a binding polypeptide. A target antigen may have one or more epitopes.

The term "about" or "approximately" means within about 20%, such as within about 10%, within about 5%, or within about 1% or less of a given value or range.

As used herein, "administer" or "administration" refers to the act of injecting or otherwise physically delivering a substance as it exists outside the body (e.g., an isolated binding polypeptide provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms.

As used herein, the term "composition" is intended to encompass a product containing the specified ingredients (e.g., an isolated binding polypeptide provided herein) in, optionally, the specified amounts, as well as any product which results, directly or indirectly, from combination of the specified ingredients in, optionally, the specified amounts.

"Effective amount" means the amount of active pharmaceutical agent (e.g., an isolated binding polypeptide of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject is can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets.

As used herein, the term "therapy" refers to any protocol, method and/or agent that can be used in the prevention, management, treatment and/or amelioration of a disease or a symptom related thereto. In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, resulting from the administration of one or more therapies (including, but not limited to, the administration of one or more prophylactic or therapeutic agents, such as an isolated binding polypeptide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

In certain exemplary embodiments, a binding polypeptide described herein treats one or more symptoms of Alzheimer's disease.

Binding Polypeptides

In one aspect, the present disclosure provides binding polypeptides (e.g., antibodies, immunoadhesins, antibody variants, and fusion proteins) that binds Aβ and treats one or more symptoms of Alzheimer's disease. The binding polypeptides disclosed herein encompass any binding polypeptide that comprises a modified Fc domain. In certain embodiments, the binding polypeptide is an antibody, or immunoadhesin or derivative thereof. Any antibody from any source or species can be employed in the binding polypeptides disclosed herein. Suitable antibodies include without limitation, human antibodies, humanized antibodies, or chimeric antibodies. Suitable antibodies include without limitation, monoclonal antibodies, polyclonal antibodies, full-length antibodies, or single chain antibodies.

Fc domains from any immunoglobulin class (e.g., IgM, IgG, IgD, IgA and IgE) and species can be used in the binding polypeptides disclosed herein. Chimeric Fc domains comprising portions of Fc domains from different species or Ig classes can also be employed. In certain embodiments, the Fc domain is a human Fc domain. In some embodiments, the Fc domain is an IgG1 Fc domain. In other embodiments, the Fc domain is an IgG4 Fc domain. In some embodiments, the Fc domain is a human IgG1 or IgG4 Fc domain. In some embodiments, the Fc domain is a human IgG1 Fc domain. In some embodiments, the Fc domain is a human IgG1 Fc domain that contains the "LALA" mutation. In the case of Fc domains of other species and/or Ig classes or isotypes, the skilled artisan will appreciate that any of the amino acid substitutions described herein can be adapted accordingly. Certain embodiments include antibodies which comprise at least one amino acid in one or more of the constant region domains and/or at least one amino acid in one or more of the variable region domains that has been deleted or otherwise altered so as to provide desired biochemical characteristics such as, e.g., reduced or enhanced effector functions, the ability to non-covalently dimerize, increased ability to localize at the site of a tumor, reduced serum half-life, increased serum half-life when compared with a whole, unaltered antibody of approximately the same immunogenicity and the like.

In certain other embodiments, binding polypeptides comprise constant regions derived from different antibody isotypes (e.g., constant regions from two or more of a human IgG1, IgG2, IgG3, or IgG4). In other embodiments, binding polypeptides comprise a chimeric hinge (i.e., a hinge comprising hinge portions derived from hinge domains of different antibody isotypes, e.g., an upper hinge domain from an IgG4 molecule and an IgG1 middle hinge domain).

In certain embodiments, the Fc domain may be mutated to increase or decrease effector function using techniques known in the art. In some embodiments, a binding polypeptide of the present disclosure comprising a modified Fc domain has altered binding affinity to an Fc receptor. There are several different types of Fc receptors, which are classified based on the type of antibody that they recognize. For example, Fc-gamma receptors (FcγR) bind to IgG class antibodies, Fc-alpha receptors (FcαR) bind to IgA class antibodies, and Fc-epsilon receptors (FcεR) bind to IgE class antibodies. The FcγRs belong to a family that includes several members, e.g., FcγRI, FcγRIIa, FcγRIIb, FcγRIIIa, and FcγRIIIb. In some embodiments, a binding polypeptide comprising a modified Fc domain has altered FcγRIIIa binding affinity, compared to a binding polypeptide comprising a wild-type Fc domain. In some embodiments, a binding polypeptide comprising a modified Fc domain has reduced FcγRIIIa binding affinity, compared to a binding polypeptide comprising a wild-type Fc domain. In some embodiments, a binding polypeptide comprising a modified Fc domain has enhanced FcγRIIIa binding affinity, compared to a binding polypeptide comprising a wild-type Fc domain. In some embodiments, a binding polypeptide comprising a modified Fc domain has approximately the same FcγRIIIa binding affinity, compared to a binding polypeptide comprising a wild-type Fc domain.

In other embodiments, binding polypeptides described herein have a constant region, e.g., an IgG1 heavy chain constant region, which is altered to reduce or eliminate glycosylation. For example, binding polypeptides (e.g., antibodies or immunoadhesins) comprising a modified Fc domain may further comprise an amino acid substitution which alters the glycosylation of the antibody Fc. For example, said modified Fc domain may have reduced glycosylation (e.g., N- or O-linked glycosylation).

Exemplary amino acid substitutions which confer reduced or altered glycosylation are disclosed in International PCT Publication No. WO 2005/018572, which is incorporated in its entirety by reference herein. In some embodiments, the binding polypeptides are modified to eliminate glycosylation. Such binding polypeptides may be referred to as "agly" binding polypeptides (e.g., "agly" antibodies). While not being bound by theory, it is believed that "agly" binding polypeptides may have an improved safety and stability profile in vivo. Agly binding polypeptides can be of any isotype or subclass thereof, e.g., IgG1, IgG2, IgG3, or IgG4. Numerous art-recognized methods are available for making "agly" antibodies or antibodies with altered glycans. For example, genetically engineered host cells (e.g., modified yeast, e.g., Picchia, or CHO cells) with modified glycosylation pathways (e.g., glycosyl-transferase deletions) can be used to produce such antibodies.

In certain embodiments, binding polypeptides may comprise an antibody constant region (e.g., an IgG constant region e.g., a human IgG constant region, e.g., a human IgG1 constant region) which mediates one or more effector functions. For example, binding of the C1-complex to an antibody constant region may activate the complement system. Activation of the complement system is important in the opsonization and lysis of cell pathogens. The activation of the complement system also stimulates the inflammatory response and may also be involved in autoimmune hypersensitivity. Further, antibodies bind to receptors on various cells via the Fc domain (Fc receptor binding sites on the antibody Fc region bind to Fc receptors (FcRs) on a cell). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In some embodiments, the binding polypeptides (e.g., antibodies or immunoadhesins) bind to an Fc-gamma receptor. In alternative embodiments, binding polypeptides may comprise a constant region which is devoid of one or more effector functions (e.g., ADCC activity) and/or is unable to bind Fcγ receptor.

In certain embodiments, the binding polypeptide of the current disclosure may comprise an antigen binding fragment of an antibody. The term "antigen-binding fragment" refers to a polypeptide fragment of an immunoglobulin or antibody which binds antigen or competes with intact antibody (i.e., with the intact antibody from which they were derived) for antigen binding (i.e., specific binding). Antigen-binding fragments can be produced by recombinant or biochemical methods that are well known in the art. Exemplary antigen-binding fragments include Fv, Fab, Fab', and (Fab')2.

In some embodiments, the binding polypeptide comprises a single chain variable region sequence (ScFv). Single chain variable region sequences comprise a single polypeptide having one or more antigen binding sites, e.g., a VL domain linked by a flexible linker to a VH domain. ScFv molecules can be constructed in a VH-linker-VL orientation or VL-linker-VH orientation. The flexible hinge that links the VL and VH domains that make up the antigen binding site includes from about 10 to about 50 amino acid residues. Connecting peptides are known in the art. Binding polypeptides may comprise at least one scFv and/or at least one constant region. In one embodiment, a binding polypeptide of the current disclosure may comprise at least one scFv linked or fused to a modified Fc domain.

In some embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc fragment of an antibody via a flexible linker (e.g., a gly/ser linker). In another embodiment a tetravalent antibody of the current disclosure can be made by fusing an ScFv molecule to a connecting peptide, which is fused to a modified Fc domain to construct an ScFv-Fab tetravalent molecule.

In another embodiment, a binding polypeptide of the current disclosure is an altered minibody. An altered minibody of the current disclosure is a dimeric molecule made up of two polypeptide chains each comprising an ScFv molecule which is fused to a modified Fc domain via a connecting peptide. Minibodies can be made by constructing an ScFv component and connecting peptide components using methods described in the art (see, e.g., U.S. Pat. No. 5,837,821 or WO 1994/009817). In another embodiment, a tetravalent minibody can be constructed. Tetravalent minibodies can be constructed in the same manner as minibodies, except that two ScFv molecules are linked using a flexible linker. The linked scFv-scFv construct is then joined to a modified Fc domain.

In another embodiment, a binding polypeptide of the current disclosure comprises a diabody. Diabodies are dimeric, tetravalent molecules each having a polypeptide similar to scFv molecules, but usually having a short (less than 10, e.g., about 1 to about 5) amino acid residue linker connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise an scFv-like molecule fused to a modified Fc domain.

In other embodiments, a binding polypeptide comprises a multi-specific or a multivalent antibody comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two VH domains in series separated by a peptide linker (VH1-linker-VH2) and the other polypeptide chain consists of complementary VL domains connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH domains in series separated by a peptide linker (VH1-linker-VH2) and the other polypeptide chain consists of complementary VL domains connected in series by a peptide linker in the opposite orientation (VL2-linker-VL1). Additional antibody variants based on the "Dual-Fv" format include the Dual-Variable-Domain IgG (DVD-IgG) bispecific antibody (see U.S. Pat. No. 7,612,181 and the TBTI format (see US 2010/0226923 A1). In some embodiments, binding polypeptides comprise multi-specific or multivalent antibodies comprising one or more variable domain in series on the same polypeptide chain fused to a modified Fc domain.

In another exemplary embodiment, the binding polypeptide is an immunoadhesin. As used herein, an "immunoadhesin" refers to a binding polypeptide comprising one or more binding domains (e.g., from a receptor, ligand, or cell-adhesion molecule) linked to an immunoglobulin constant domain (i.e., an Fc region) (see e.g., Ashkenazi et al. 1995, *Methods* 8 (2): 104-115, and Isaacs (1997) *Brit. J. Rheum.* 36:305 which are incorporated by reference herein in their entireties). Immunoadhesins are identified by the suffix "-cept" in their international nonproprietary names (INN). Like antibodies, immunoadhesins have long circulating half-lives, are readily purified by affinity-based methods, and have avidity advantages conferred by bivalency. Examples commercially available therapeutic immunoadhesins include etanercept (ENBREL®), abatacept (ORENCIA®), rilonacept (ARCALYST®), aflibercept (ZALTRAP®/EYLEA®), and belatacept (NULOJIX®).

In certain embodiments, the binding polypeptide comprises immunoglobulin-like domains. Suitable immunoglobulin-like domains include, without limitation, fibronectin domains (see, for example, Koide et al. (2007), *Methods Mol. Biol.* 352:95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

For binding polypeptides and immunoadhesins of the present disclosure, virtually any antigen may be targeted by the binding polypeptides, including but not limited to proteins, subunits, domains, motifs, and/or epitopes of target antigens, which includes both soluble factors such as cytokines and membrane-bound factors, and transmembrane receptors.

In certain embodiments, a binding polypeptide, e.g., an antibody, is a multispecific antibody, e.g. a bispecific antibody. Multispecific antibodies are monoclonal antibodies that have binding specificities for at least two different sites. In certain embodiments, bispecific antibodies can be used to cross the blood brain barrier (BBB). Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J.

Immunol. 152 (1994) 5368-5374); and preparing trispecific antibodies as described, e.g., in Tutt, A. et al., J. Immunol. 147 (1991) 60-69).

In one embodiment the CH3 domains of the heavy chains of the bispecific antibody are altered by the "knob-into-holes" technology which is described in detail with several examples in e.g. WO 96/027011, WO 98/050431, Ridgway J. B., et al., Protein Eng. 9 (1996) 617-621, Merchant, A. M., et al., Nat Biotechnol 16 (1998) 677-681. In this method, the interaction surfaces of the two CH3 domains are altered to increase the heterodimerization of both heavy chains containing said two CH3 domains. Each of the two CH3 domains (of the two heavy chains) can be the "knob," while the other is the "hole." The introduction of a disulfide bridge can be utilized to stabilize the heterodimers (Merchant, A. M, et al., Nature Biotech 16 (1998) 677-681, Atwell, S., et al. J. Mol. Biol. 270 (1997) 26-35), as well as to increase the yield.

In one embodiment, a bispecific antibody is characterized in that the CH3 domain of one heavy chain and the CH3 domain of the other heavy chain each meet at an interface which comprises an original interface between the antibody CH3 domains, wherein said interface is altered to promote the formation of the bispecific antibody, wherein the alteration is characterized in that: a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain; and b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

In one embodiment the amino acid residue having a larger side chain volume is selected from the group consisting of arginine (R), phenylalanine (F), tyrosine (Y) and tryptophan (W).

In one embodiment the amino acid residue having a smaller side chain volume is selected from the group consisting of alanine (A), serine(S), threonine (T) and valine (V).

In one embodiment both CH3 domains are further altered by the introduction of cysteine (C) as amino acid in the corresponding positions of each CH3 domain such that a disulfide bridge between both CH3 domains can be formed.

In an exemplary embodiment, the multispecific antibody comprises the amino acid T366W mutation in the first CH3 domain of the "knobs chain and the amino acid T366S, L368A, Y407V mutations in the second CH3 domain of the "hole chain." An additional interchain disulfide bridge between the CH3 domains can also be used (Merchant, A. M., et al., Nature Biotech. 16 (1998) 677-681) e.g. by introducing the amino acid Y349C mutation into the CH3 domain of the "hole chain and the amino acid E356C mutation or the amino acid S354C mutation into the CH3 domain of the "knobs chain."

In one embodiment the bispecific antibody comprises Y349C, T366W mutations in one of the two CH3 domains and E356C, T366S, L368A, Y407V mutations in the other of the two CH3 domains. In one embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering according to EU index of Kabat; (Kabat, E. A., et al., Sequences of Proteins of Immunological Interest, 5th ed., Public Health Service, National Institutes of Health, Bethesda, Md. (1991))). Further knobs-in-holes technologies as described by EP 1 870 459 A1, can be used alternatively or additionally. Thus, another example for the bispecific antibody are R409D, K370E mutations in the CH3 domain of the "knobs chain" and D399K, E357K mutations in the CH3 domain of the "hole chain" (numbering according to EU index of Kabat; (Kabat, E. A., et al., Sequences of Proteins of Immunological Interest, 5th ed., Public Health Service, National Institutes of Health, Bethesda, Md. (1991)).

In one embodiment the bispecific antibody comprises a T366W mutation in the CH3 domain of the "knobs chain" and T366S, L368A, Y407V mutations in the CH3 domain of the "hole chain" and additionally R409D, K370E mutations in the CH3 domain of the "knobs chain" and D399K, E357K mutations in the CH3 domain of the "hole chain."

Nucleic Acids and Expression Vectors

In one aspect, the invention provides polynucleotides encoding the binding polypeptides disclosed herein. Methods of making a binding polypeptide comprising expressing these polynucleotides are also provided.

Polynucleotides encoding the binding polypeptides disclosed herein are typically inserted in an expression vector for introduction into host cells that may be used to produce the desired quantity of the claimed antibodies, or immunoadhesins. Accordingly, in certain aspects, the invention provides expression vectors comprising polynucleotides disclosed herein and host cells comprising these vectors and polynucleotides.

The term "vector" or "expression vector" is used herein for the purposes of the specification and claims, to mean vectors used for introducing into and expressing a desired gene in a cell. As known to those skilled in the art, such vectors may easily be selected from the group consisting of plasmids, phages, viruses and retroviruses. In general, a vector will comprise a selection marker, appropriate restriction sites to facilitate cloning of the desired gene and the ability to enter and/or replicate in eukaryotic or prokaryotic cells.

Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments the cloned variable region genes are inserted into an expression vector along with the heavy and light chain constant region genes (such as human genes) synthesized as discussed above.

In other embodiments, a binding polypeptide as described herein may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is incorporated by reference herein. Those skilled in the art will appreciate that such expression systems may be used to effectively produce the full range of polypeptides disclosed in the instant application.

More generally, once a vector or DNA sequence encoding a binding polypeptide of the present disclosure has been prepared, the expression vector may be introduced into an appropriate host cell. That is, the host cell may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, e.g., Ridgway, A. A. G. "Mammalian Expression Vectors" Chapter 24.2, pp. 470-472 Vectors, Rodriguez and Denhardt, Eds. (Butterworths, Boston, MA 1988). The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refer to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for expression of the binding polypeptide is of eukaryotic or prokaryotic origin. In one embodiment, the host cell line used for expression of the binding polypeptide is of bacterial origin. In one embodiment, the host cell line used for expression of the binding polypeptide is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER6™ (Crucell) or FUT8-knock-out CHO cell lines (POTELLIGENT™ cells) (Biowa, Princeton, NJ)). In one embodiment NS0 cells may be used. Host cell lines are typically available from commercial services, the American Tissue Culture Collection or from published literature.

In vitro production allows scale-up to give large amounts of the desired binding polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

One or more genes encoding binding polypeptides can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

Methods of Treatment

In one aspect, the invention provides methods of treating one or more symptoms of Alzheimer's disease in a patient in need thereof comprising administering an effective amount of a binding polypeptide disclosed herein. In certain embodiments, the present disclosure provides kits and methods for the treatment of Alzheimer's disease in a mammalian subject in need of such treatment. In certain exemplary embodiments, the subject is a human.

A binding polypeptide disclosed herein may be administered in a number of ways depending upon whether local or systemic treatment is desired and upon the area to be treated. For example, administration may be parenteral, including, but not limited to intravenous drip administration, subcutaneous administration, intraperitoneal administration, intramuscular administration, intrathecal administration, or intraventricular (e.g., intracerebroventricular) administration. In certain exemplary embodiments, a binding polypeptide is delivered across the blood-brain barrier (BBB) using a variety of suitable compositions and methods described herein.

A subject diagnosed with or suspected of having Alzheimer's disease can be administered a binding polypeptide directly into the brain (e.g., into the globus pallidus or the corpus striatum of the basal ganglia, and near the medium spiny neurons of the corpus striatum). In addition to a binding polypeptide, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). For the treatment of Alzheimer's disease, for example, symptomatic therapies can include the drugs Razadyne® (galantamine), Exelon® (rivastigmine), Aricept® (donepezil), Namenda® (memantine), or Namzaric® (memantine and donepezil). Other therapies can include psychotherapy, physiotherapy, speech therapy, communicative and memory aids, social support services, and dietary advice.

A binding polypeptide can be delivered to neural cells of the brain. Delivery methods that do not require passage of the composition across the BBB can be utilized. For example, a pharmaceutical composition containing a binding polypeptide can be delivered to the patient by injection directly into the area containing the disease-affected cells. For example, the pharmaceutical composition can be delivered by injection directly into the brain. The injection can be by stereotactic injection into a particular region of the brain (e.g., the cerebral ventricles the substantia nigra, cortex, hippocampus, striatum, or globus pallidus). The binding polypeptide can be delivered into multiple regions of the central nervous system (e.g., into multiple regions of the brain, and/or into the spinal cord). The binding polypeptide can be delivered into diffuse regions of the brain (e.g., diffuse delivery to the cortex of the brain).

In one embodiment, a binding polypeptide can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of binding polypeptide. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is mediated by a conduit leading from the pump or reservoir to the site of release. Devices for delivery to the brain are described, for example, in U.S. Pat. Nos. 6,093,180 and 5,814,014, incorporated herein by reference.

One skilled in the art would be able, by routine experimentation, to determine what an effective, non-toxic amount of modified binding polypeptide would be for the purpose of treating malignancies. For example, a therapeutically active amount of a binding polypeptide of the present disclosure may vary according to factors such as the disease stage (e.g., pre-clinical Alzheimer's disease, mild cognitive impairment, mild dementia, moderate dementia or severe dementia), age, sex, medical complications (e.g., immunosuppressed conditions or diseases) and weight of the subject, and the ability of the modified antibody to elicit a desired response in the subject. The dosage regimen may be adjusted to provide the optimum therapeutic response. For example, several divided doses may be administered daily, weekly, every other week, every three weeks, every four weeks or the like, and/or the dose may be proportionally reduced as indicated by the exigencies of the therapeutic situation.

Pharmaceutical Compositions

Methods of preparing and administering binding polypeptides of the current disclosure to a subject are well known to or are readily determined by those skilled in the art. The route of administration of the binding polypeptides of the current disclosure may be oral, parenteral, by inhalation or topical. The term parenteral as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. In some embodiments, the binding polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M, e.g., 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will typically be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, isotonic agents will be included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified binding polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation include vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will typically have labels or package inserts indicating that the associated compositions are useful for treating a subject suffering from, or predisposed to autoimmune or neoplastic disorders.

Effective doses of the compositions of the present disclosure, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals, including transgenic mammals, can also be treated. Treatment dosages may be titrated using routine methods known to those of skill in the art to optimize safety and efficacy.

Binding polypeptides of the current disclosure can be administered on multiple occasions. Intervals between single dosages can be weekly, monthly or yearly. Intervals can also be irregular as indicated by measuring blood levels of modified binding polypeptide or antigen in the patient. In some methods, dosage is adjusted to achieve a plasma modified binding polypeptide concentration of about 1-1000 µg/ml and in some methods about 25-300 µg/ml. Alternatively, binding polypeptides can be administered as a sustained release formulation, in which case less frequent administration is required. For antibodies, dosage and frequency vary depending on the half-life of the antibody in the patient. In general, humanized antibodies show the longest half-life, followed by chimeric antibodies and non-human antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from about 0.1 to about 25 mg per dose, especially about 0.5 to about 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose) at relatively short intervals is sometimes required until progression of the disease is reduced or terminated, or until the patient shows partial or complete amelioration of disease symptoms. Thereafter, the patient can be administered a prophylactic regime.

A pharmaceutical composition in accordance with the present disclosure can comprise a pharmaceutically acceptable, non-toxic, sterile carrier such as physiological saline, nontoxic buffers, preservatives and the like. For the purposes of the instant application, a pharmaceutically effective amount of the binding polypeptide, immunoadhesin or recombinant thereof, conjugated or unconjugated to a therapeutic agent, shall be held to mean an amount sufficient to achieve effective binding to an antigen and to achieve a benefit, e.g., to ameliorate one or more symptoms of Alzheimer's disease. The pharmaceutical compositions of the present disclosure may be administered in single or multiple doses to provide for a pharmaceutically effective amount of a binding polypeptide.

In keeping with the scope of the present disclosure, the binding polypeptides of the disclosure may be administered to a human or other animal in accordance with the aforementioned methods of treatment in an amount sufficient to produce a therapeutic or prophylactic effect. The binding polypeptides of the disclosure can be administered to such human or other animal in a conventional dosage form prepared by combining an antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding polypeptides described in the current disclosure may prove to be particularly effective.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

44

EXAMPLES

The present invention is further illustrated by the following examples which should not be construed as further limiting.

Example 1: Brief Overview of Aβ Monoclonal Antibody Discovery Process

Trianni mice were immunized either with sonicated human Alzheimer's disease (AD) brain amyloid plaques (FusA), aggregated synthetic Aβ (FusB), or human AD brain amyloid plaque-seeded synthetic Aβ (FusC) (FIG. 1). Of note, the Fc domains were mouse but Fv domains were human in most cases.

Hybridomas having good-to-moderate binding to synthetic Aβ protofibrils (PF) were selected. Antibodies that bound with high affinity to monomeric Aβ and low affinity to other types of aggregated proteins (e.g., synuclein and SOD) were counter-selected. Finally, murine IgG antibodies were screened using the "cellular iN assay" (described further below) wherein neuroprotection against AD-brain synaptotoxic forms of oligomeric Aβ (oAβ) was assessed. Active antibodies having low binding to both Aβ protofibrils and fibrillar Aβ were selected. Promising antibodies were cloned and reformatted into a human IgG1 LALA Fc domain.

The binding properties of the reformatted, human IgG1 monoclonal antibodies (mAbs) were assessed for selectivity against monomer Aβ, as well as low binding to Aβ PF and to fibrillar Aβ. Two of the identified human mAbs that did not show significant binding to Aβ PF (nor to the other forms) were retested in the iN cellular assay and were determined to be neuro-protective.

Human mAbs (hIgGs) that did not bind other aggregated proteins were assessed using the iN assay, EC50s were obtained, and the results were reproduced. Five hIgGs were tested in a second functional assay, the electrophysiology LTP assay, as described further herein below.

Example 2: Trianni Mouse Immunization and Hybridoma Generation

Immunization

Trianni mice transgenic for the human IgG heavy and kappa light chains were immunized with synthetic Aβ 1-42 peptide that had been aggregated as previously reported [please provide cite] or synthetic Aβ 1-42 peptide seeded and aggregated on a scaffold of sonicated human AD-brain derived amyloid plaque fragments. Mice were boosted with these proteins 3-5 times every two weeks.

Hybridoma cells were made by fusing mouse myeloma cells (from the BALB/c B-lymphoblast cell line SP2/0 fused with Sendai virus) deficient in adenosine phosphoribosyl-transferase (APRT) with spleen cells from immunized mice. Hypoxanthine, azaserine, and thymidine (HAT) selection and serial dilutions were performed to achieve single cell clonality.

Screening

Indirect ELISA was utilized for screening and counter-screening assays. Surface plasma resonance (SPR) off-rate analyses were performed to determine binding affinity. Analysis was performed on a Biacore T100 with HBS-EP and running buffer (10 mM HEPES, 150 mM NaCl, 3 mM EDTA, 0.005% P20). A series A Protein A sensor chip was used for the analysis. Antibodies were diluted to 5 μg/ml in HBS-EP+. Monomeric Aβ1-42 peptide (SEC purified) was diluted to 1000 μM (4.5 mg/ml) in HBS-EP+ and then serially diluted two-fold for a total of six concentrations. Aβ1-42 PFs were diluted to 100 nM (66 μg/ml) in HBS-EP+ and then serially diluted two-fold for a total of six concentrations. Antibodies were captured via Fc domains on a Protein A surface for 60 seconds at 10 μl/min and then the Aβ peptide solution (monomeric or PFs) was injected over the surface for 180 seconds at 30 μl/minute, followed by a 360-second dissociation. The protein A surface was regenerated with a 60 second injection of 10 mM glycine-HCl, pH 1.7. The resulting sensorgrams were double-referenced and fitted to a 1:1 binding model to determine $k_a$, $k_d$ and $K_D$.

Octet Off-rate and kinetics analyses was performed using an OctetRed96 (Forte Bio), PBS running buffer and Protein A sensor tips. Antibodies were diluted to 1 or 5 μg/mL in PBS for binding evaluation to PFs or monomer, respectively. Antigens were diluted to 1 μM (Aβ1-40) or 30 nM (PFs), then serially diluted 1:3 for a total of 3 concentrations. Antibodies were captured onto sensor tips to 1 nm load (Aβ1-40) or 0.2 nm load (PFs) which were then dipped into antigen for 300 seconds, then dissociated for 360 seconds in PBS. Data were double referenced and fit with 1:1 binding model.

Screening and counter-screening workflows were performed as follows. For the analysis of mouse sera titers, indirect ELISA was performed on Aβ Protofibrils or Aβ-derived diffusible ligands, i.e. synthetic Aβ oligomers (AD-DLs) and/or Aβ $^{1/2}$tmax. For primary screens, indirect ELISA was performed on Aβ PFs and/or ADDLs. For counter-screens, oligomeric versus monomeric Aβ was selected for in order to eliminate clones that strongly bound the monomeric form. Off-rates were assessed using Biacore or indirect ELISA (FIG. 1A and FIG. 1B). Indirect ELISA was used to identify aggregated alpha synuclein and aggregated SOD in order to eliminate clones that also bound alternate, off-target amyloid structures.

For the secondary screens, an in vitro, cell-based assay was used to identify clones capable of neutralizing the neuritotoxic effects of AD-brain extracts on iN cells.

For the tertiary screen, an invitro, functional LTP assay was used to identify clones capable of neutralizing the inhibitory effects of AD-brain extracts on LTP as measured in brain slices.

Hybridoma Screening Summary

Approximately 4400 clones were put through the primary ELISA screen. Three different immunization strategies were employed, and five fusions were performed. The primary ELISA screen was performed on Aβ 1-42-derived protofibrils and/or Aβ 1-42-derived ADDLs.

Approximately 80 clones were assessed by a counter-screen to identify clones with minimal to no binding to off target entities, e.g., Aβ 1-40 monomer and/or Aβ 1-42 monomer, Aβ 1-42 fibrils, synuclein fibrils, and aggregated SOD-1.

Approximately 50 clones were assessed by a secondary screen using cell-based functional screens (e.g., the iN cell assay). Multiple assay runs were performed using the original hybridomas. Additionally, cloned, reformatted and recombinantly produced IgG1 LALA versions of the top candidates were also tested. EC50 data were obtained and replicated for the top clones in order to rank the clones according to those best able to neutralize oligomeric Aβ synaptotoxicity.

Four clones were assessed by tertiary LTP functional screens at one or more concentrations, and rank ordered according to their relative ability to rescue LTP.

Lead clone(s) were selected based on good binding selectivity and preservation of functional activity in both IN and LTP assays.

Example 3: Fusion B (FusB) Summary

Aggregated synthetic Aβ was administered to Trianni mice using Sigma adjuvant. The immunizations were performed i.p. using 200 μl (50 μg antigen) total/injection. Titers assessed were assessed post 5th immunization on ½ tmax (4 μg/mL coat) or ADDLs (1 μg/mL coat) (FIG. 3). Based on these data, mouse M13 was set aside to rest prior to final boost and fusion.

Mouse M13 (Titer Approximately 1:600,000)

Figure 37:
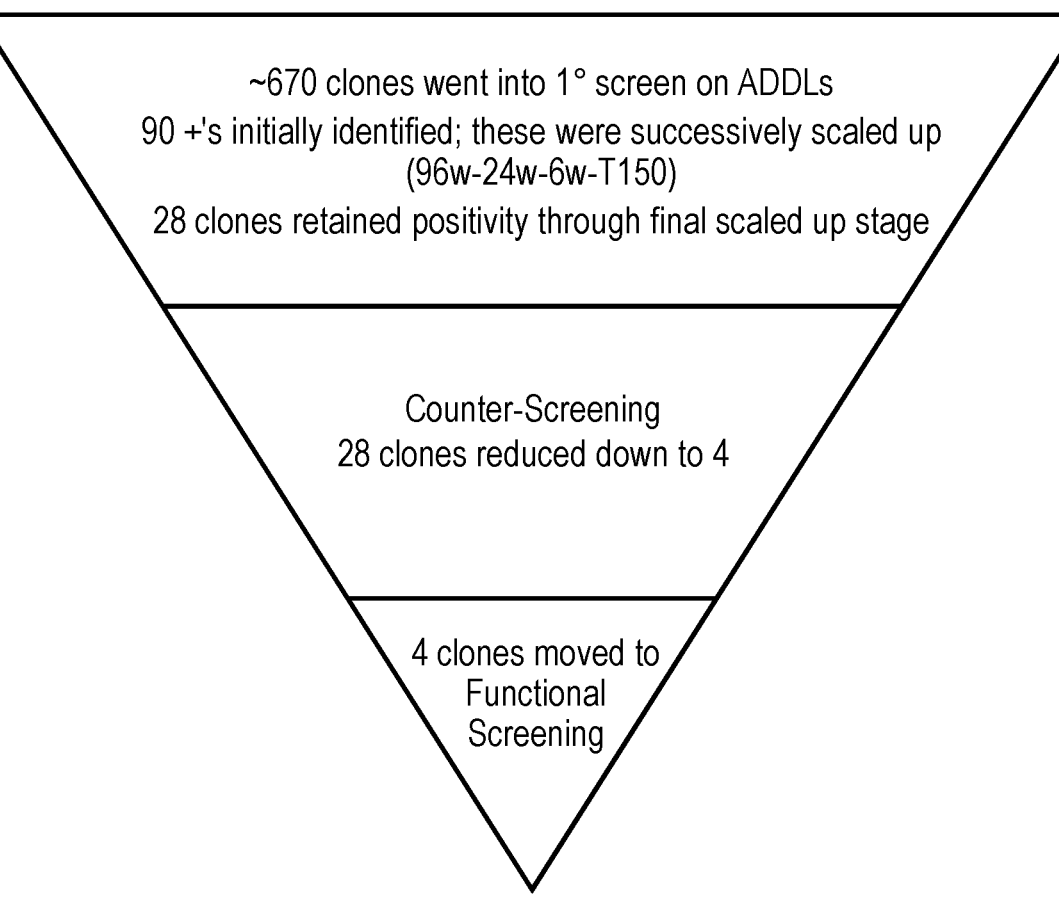
FIG. 37 summarizes the fusion B screen.

Approximately 670 clones were identified for a primary screen on ADDLs. 90 positive clones were initially identified by ELISA against ADDLs. The 90 positive clones were moved to a 24-well screen, of which 17 had lost binding or didn't have enough cells. Accordingly, 73 clones were moved to a 6-well stage. From the 6-well stage, 15 clones were scaled-up for production (Group 1), 13 slow growers were scaled up later (Group 2). In total, 28 clones were moved to production and purified by Protein Maker. Four clones moved on to functional screening. The FusB screen is summarized at FIG. 37. Binding and characterization data of the lead FusB clones are depicted in FIGS. 4-18.

Two clones were identified as two isotypes and were re-cloned. One clone, B47-6, was moved forward and purified along with the Fusion C clones.

Example 4: Fusion C (FusC) Summary

Figure 18:
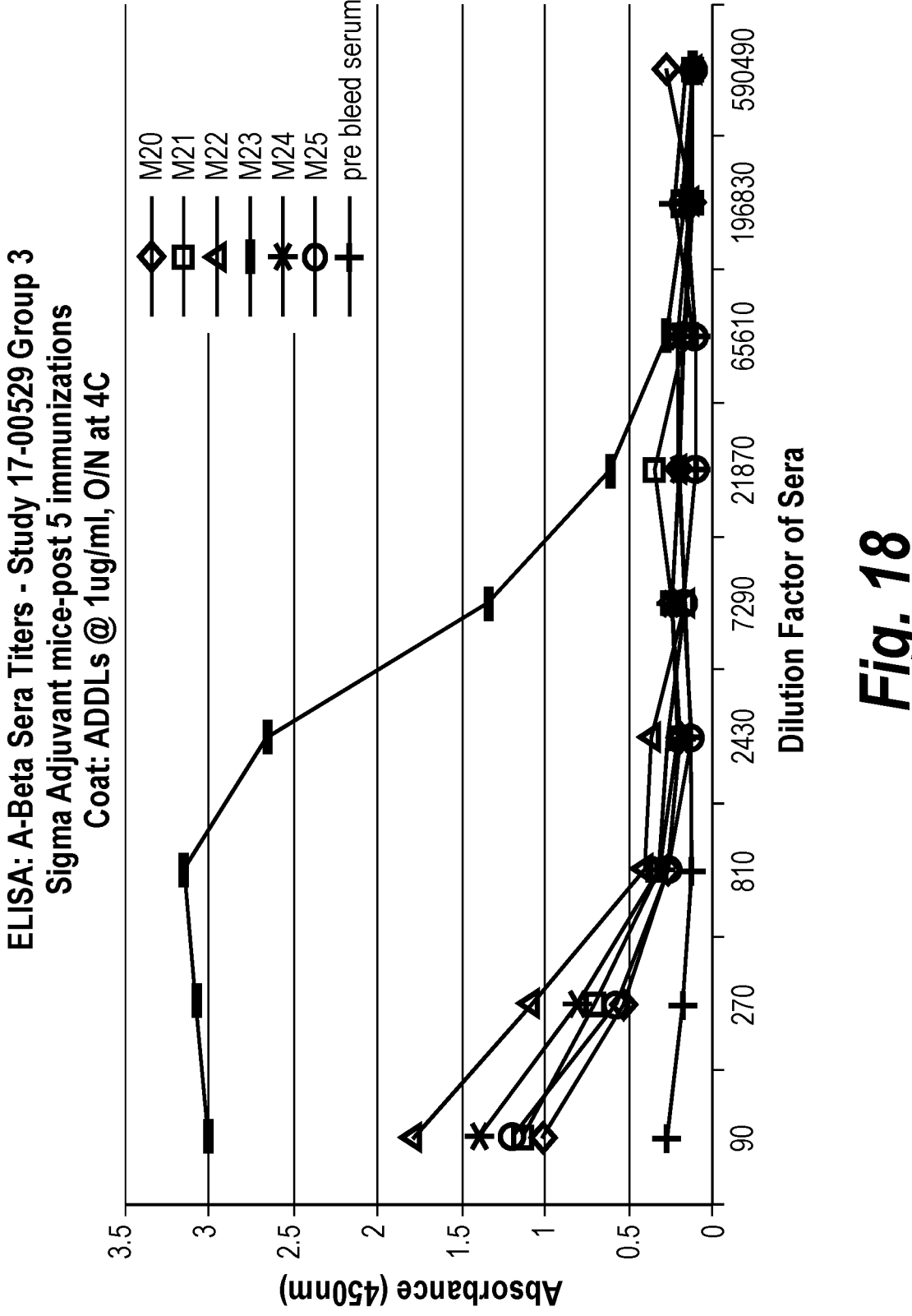
FIG. 18 graphically depicts post-fifth immunization titers for amyloid plaque-seeded Aβ cohort 3 showing results obtained by ELISA based on ADDLs (1 μg/ml, overnight at 4° C.). Mouse M23 was to be used to produce hybridoma cells (titer, 3× pre-immunized background).
Figure 21:
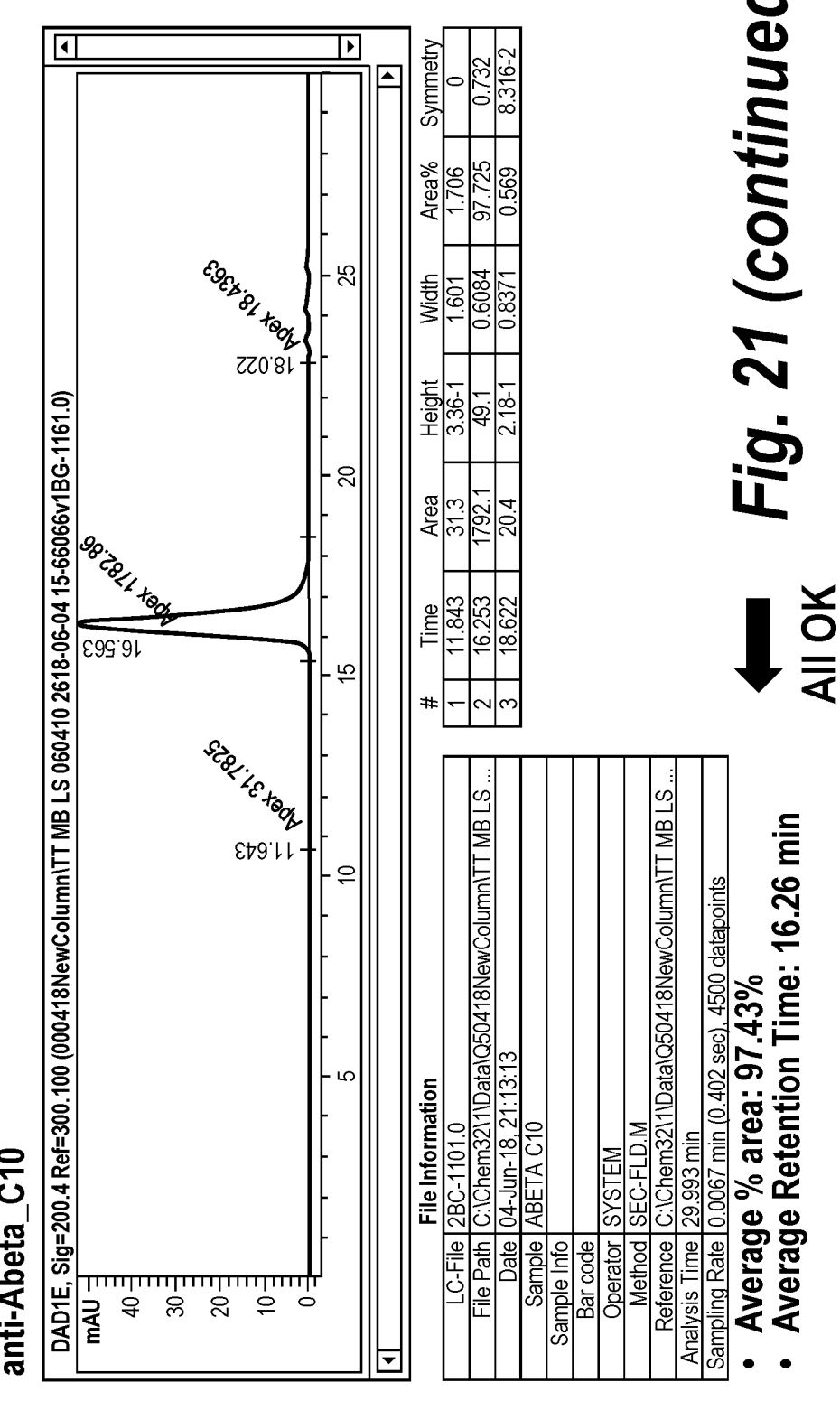
FIG. 21 graphically depicts aSEC profiles of select purified FusC clones.
Figure 21:
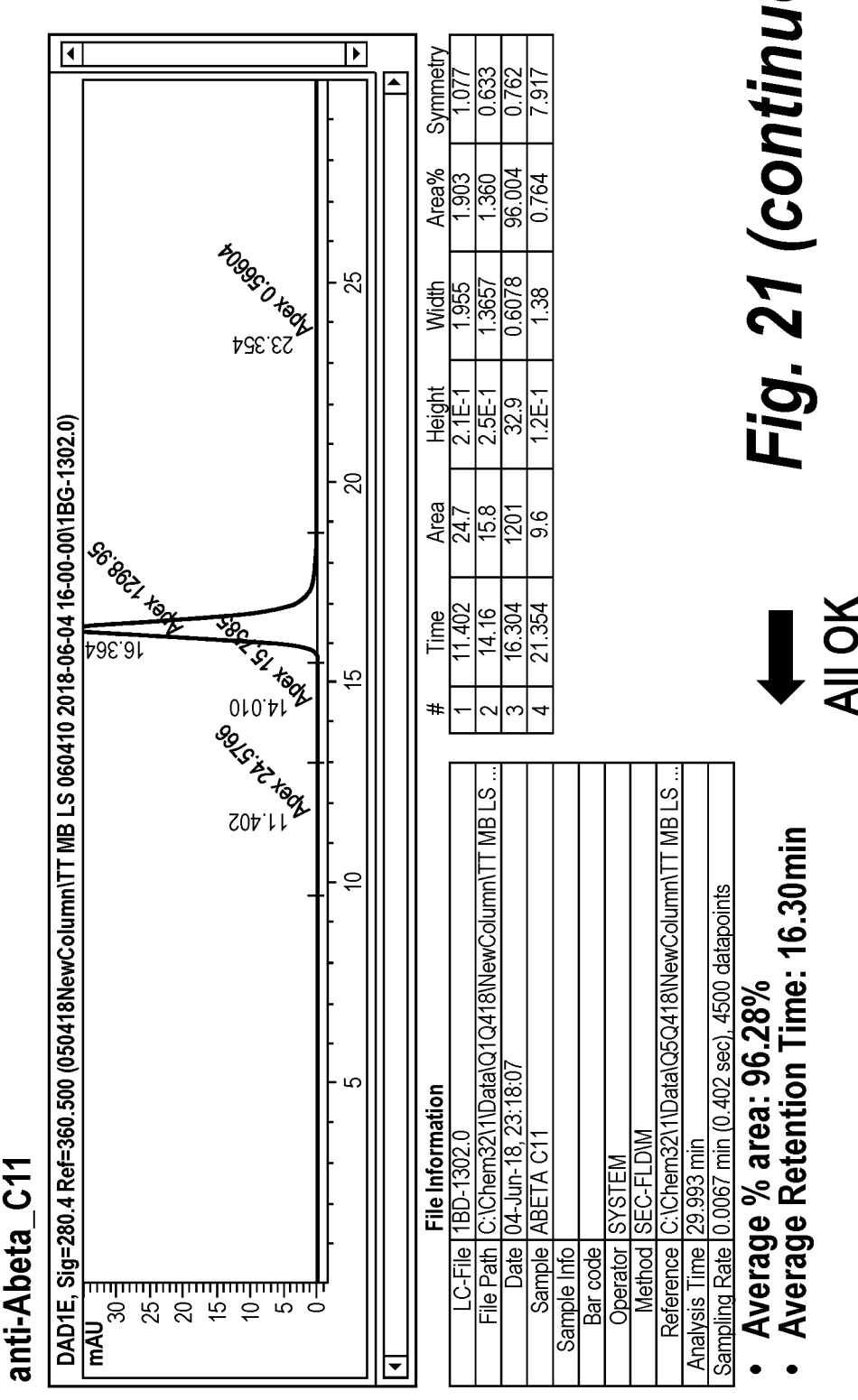
Figure 22:
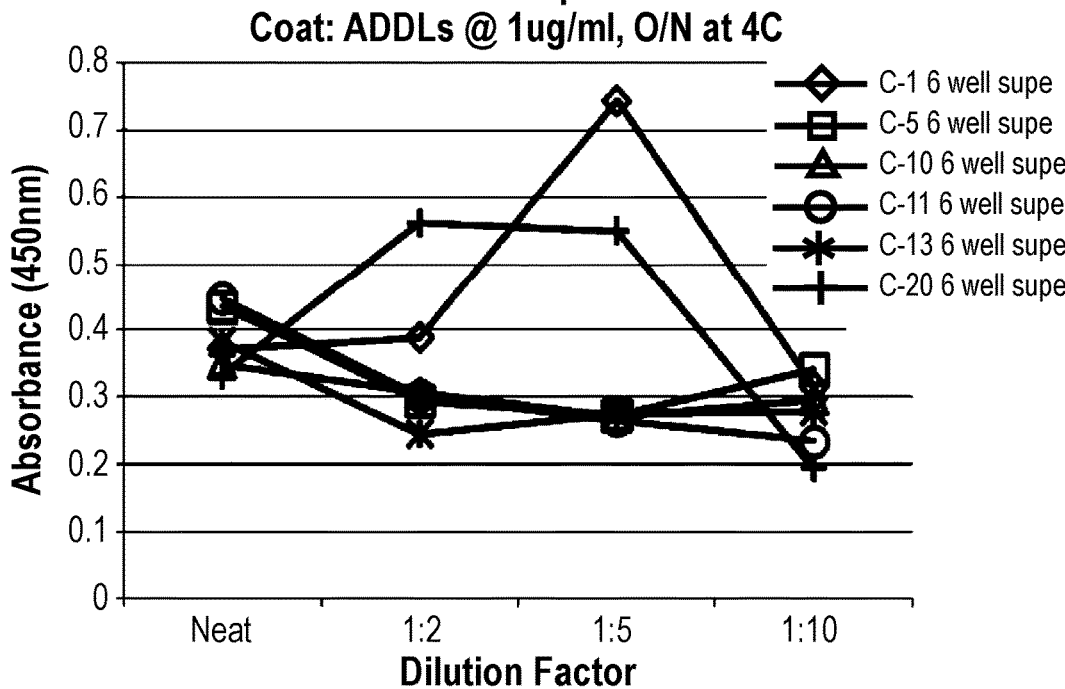
FIG. 22 graphically depicts ELISA results of FusC clone supernatants on ADDLs. Weak to no binding was observed for synthetic Aβ ADDLs by ELISA.
Figure 23:
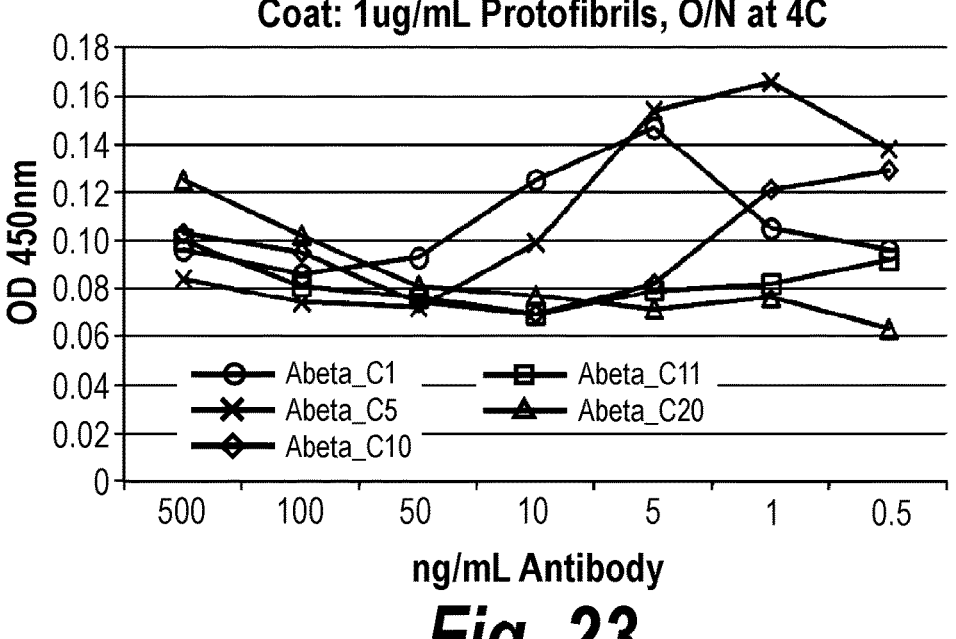
FIG. 23 graphically depicts titration ELISA results of purified FusC clones on PFs. Neither purified clone C10 nor clone C11 exhibited appreciable binding to synthetic Aβ PFs by ELISA.
Figure 25:
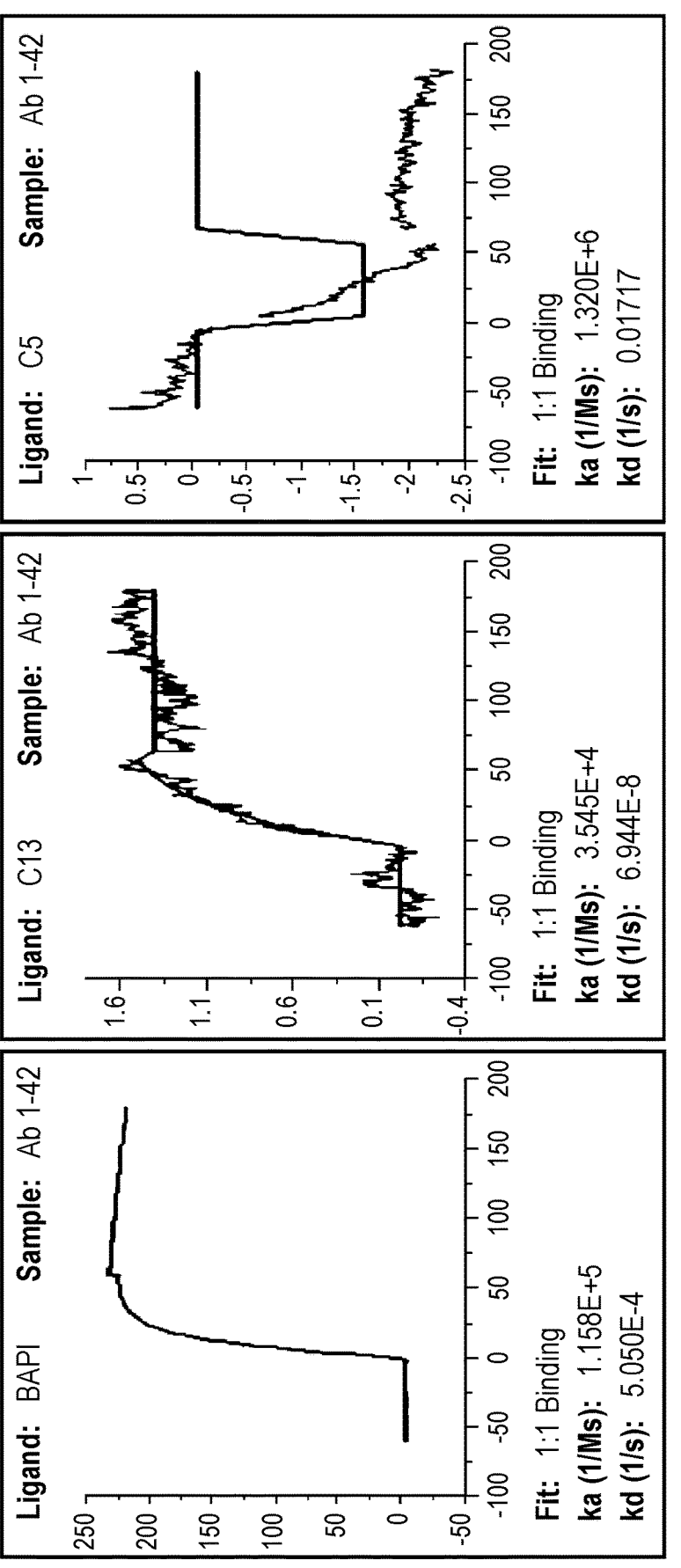
FIG. 25 graphically depicts off-rate data for selected purified FusC clones for the Aβ 1-42 monomer.
Figure 25:
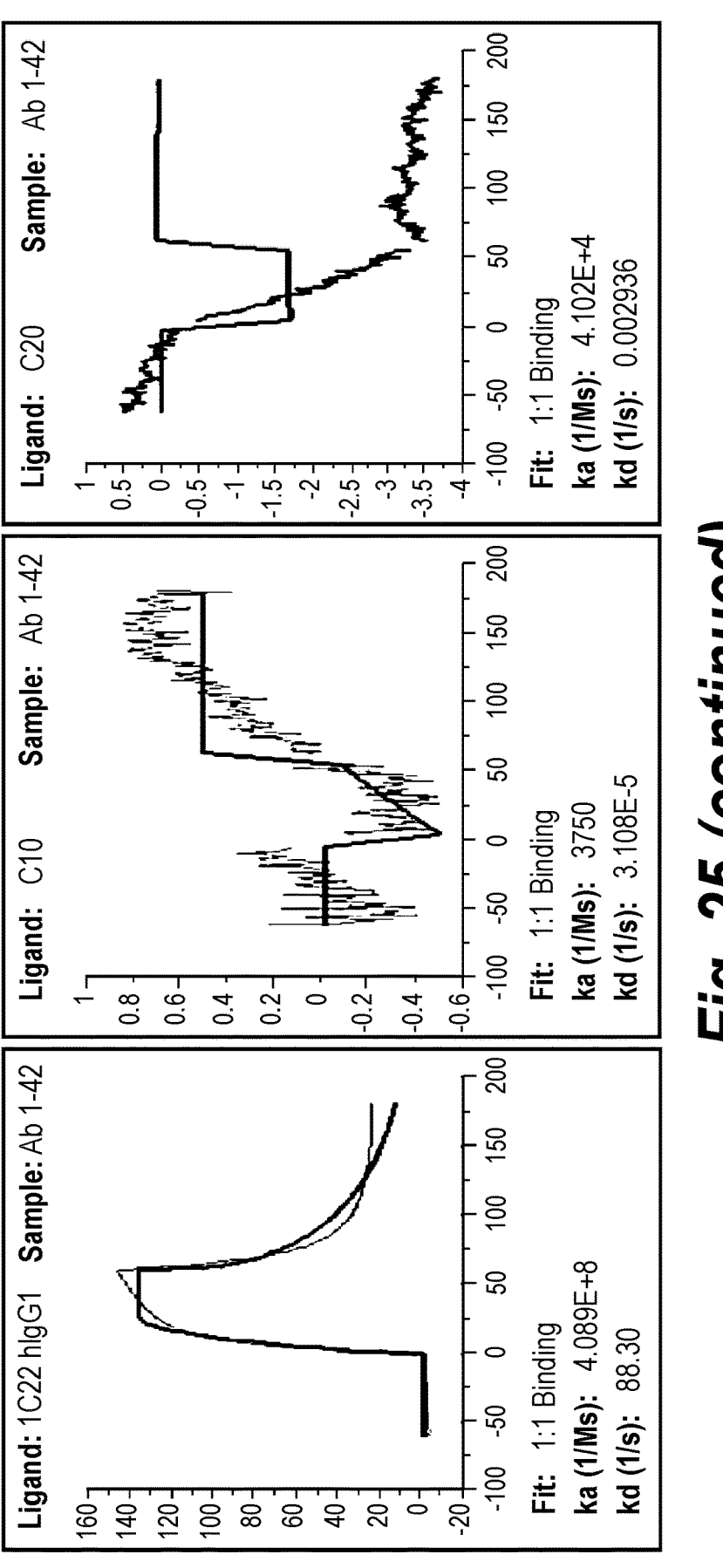
Figure 25:
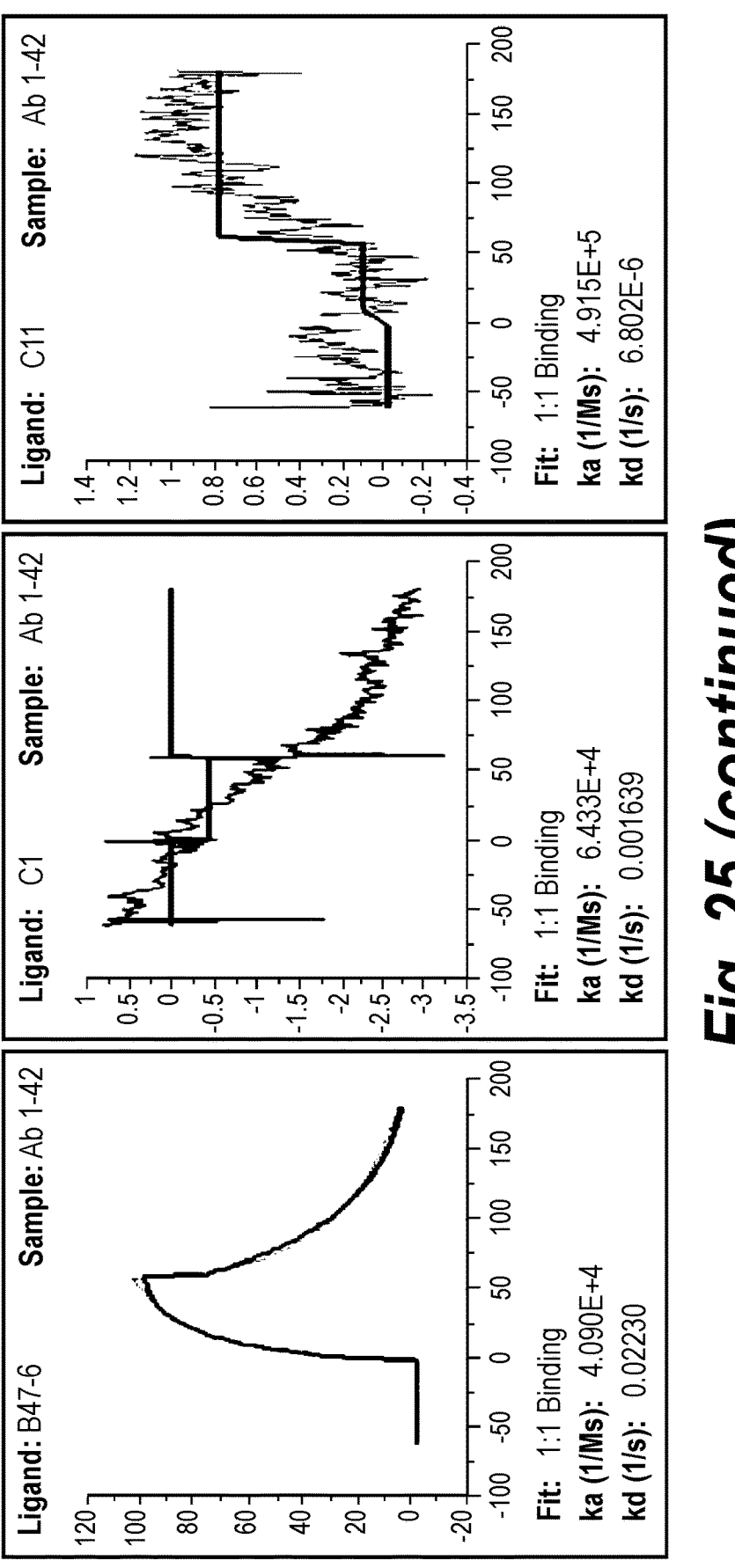
Figure 26:
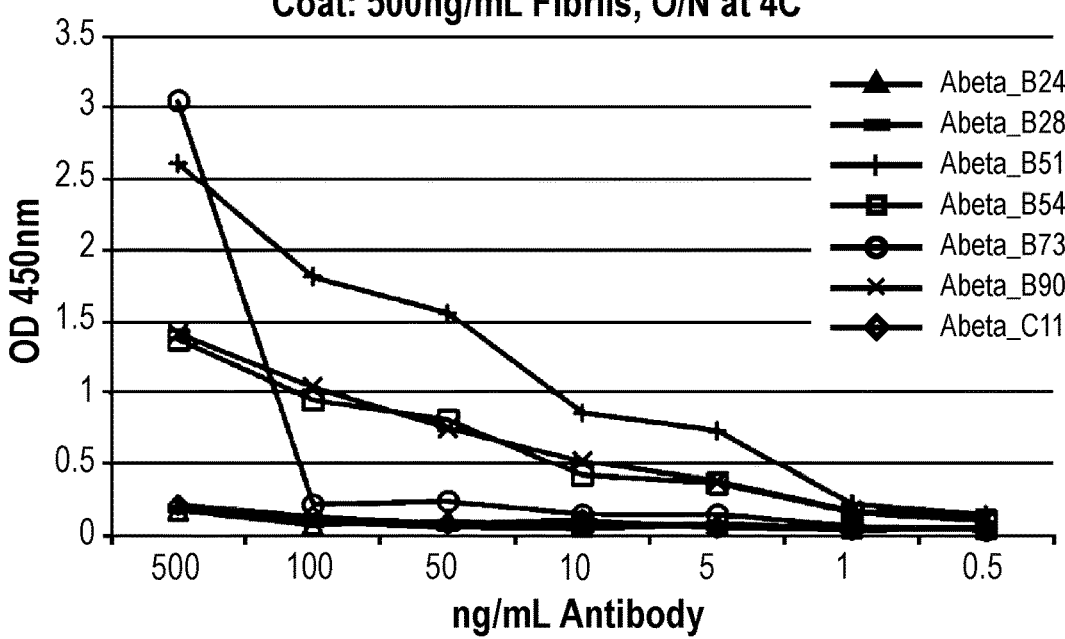
FIG. 26 graphically depicts the result of a counter-screen on fibrils for purified clone C11.
Figure 27:
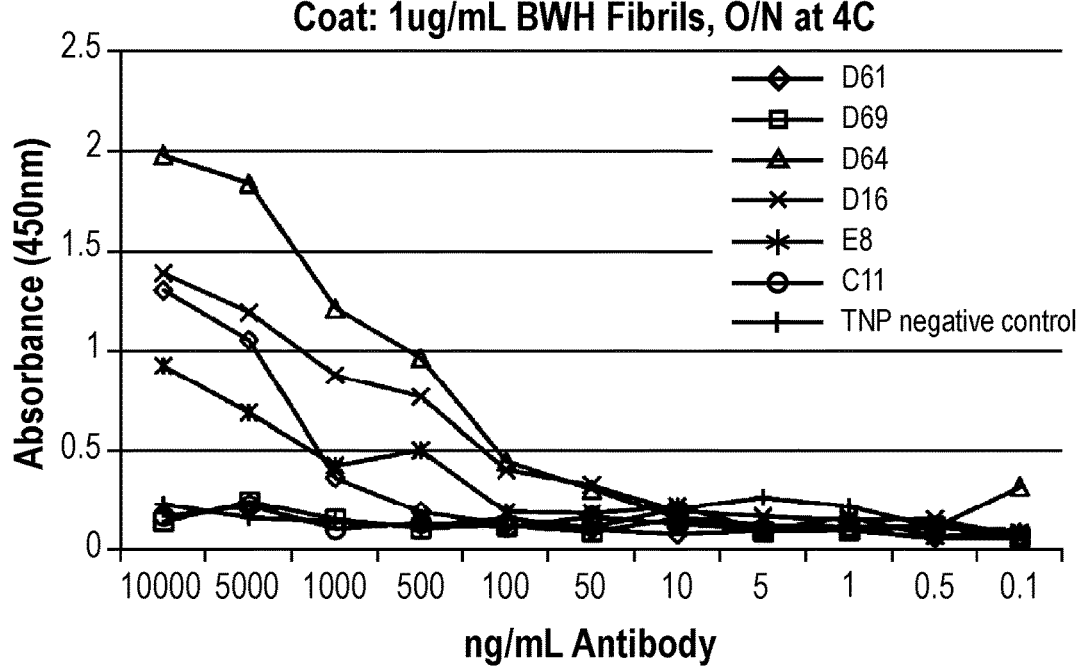
FIG. 27 graphically depicts the result of a fibrils counter-screen for purified clone C11.
Figure 28:
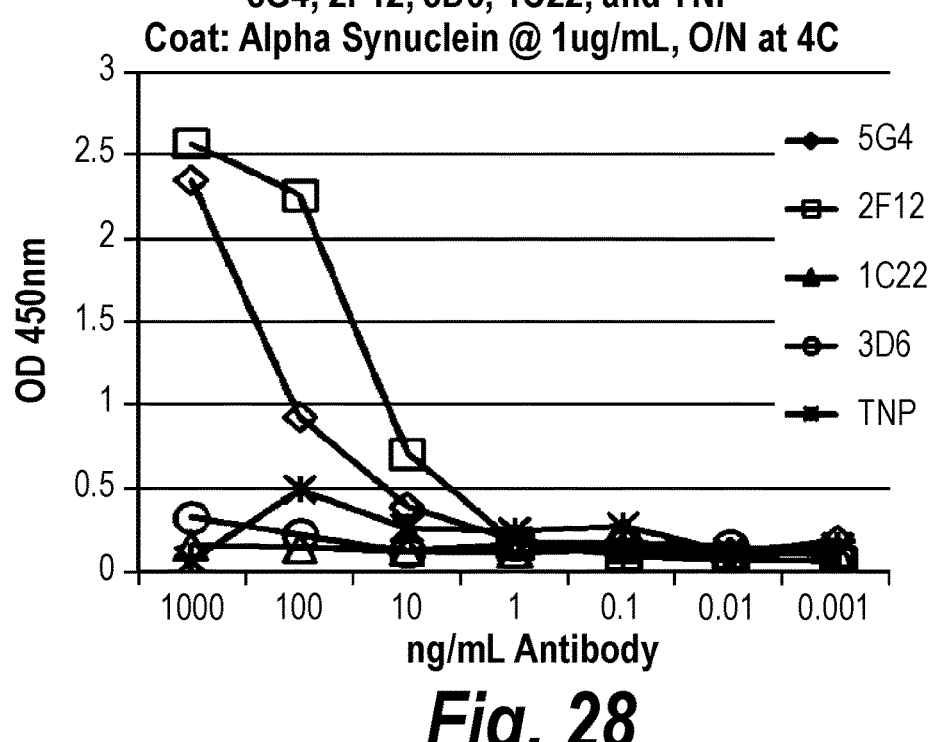
FIG. 28 graphically depicts the result of an aggregated alpha-synuclein counter-screen for purified clone C11.
Figure 29:
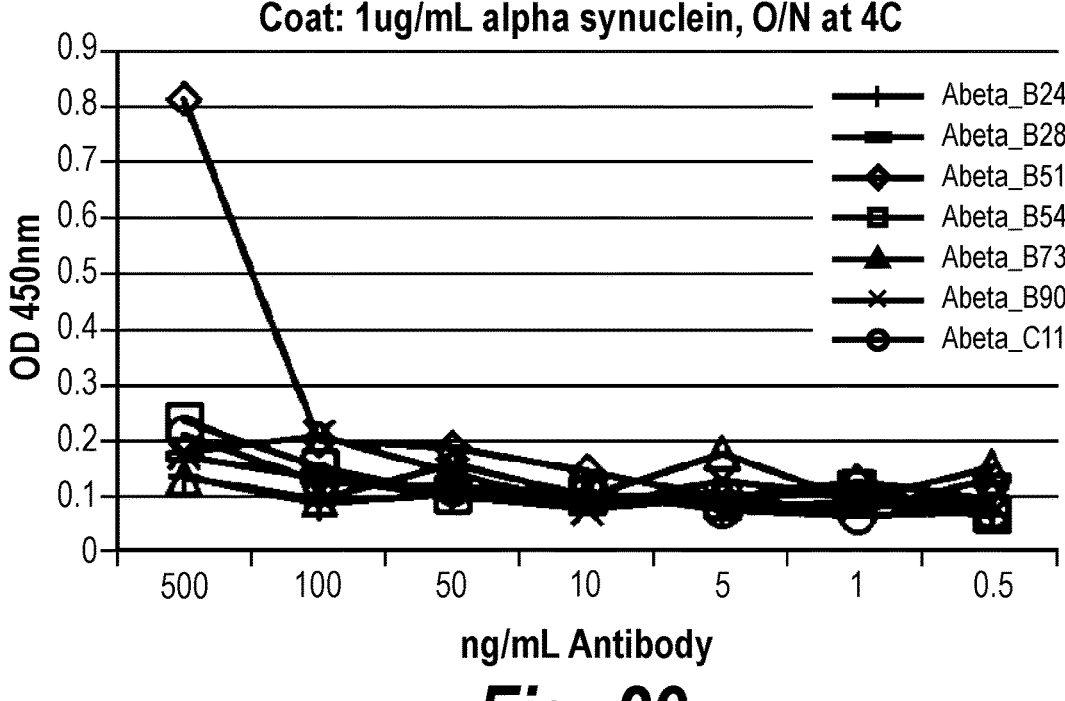
FIG. 29 graphically depicts the result of a SOD-1 counter-screen for fusion D and E clones (10,000 ng/ml-100 ng/ml). Clones C10 and C11 had identical variable regions and were referred to as C11 in later experiments.

AD-brain amyloid plaque-seeded synthetic Aβ was administered to Trianni mice using Sigma adjuvant. Titers were assessed post 5th immunization on ½ tmax (4 μg/mL coat) or ADDLs (1 μg/mL coat) (FIG. 18). Based on these data, mouse M23 was set aside to rest prior to final boost and fusion.

Figure 38:
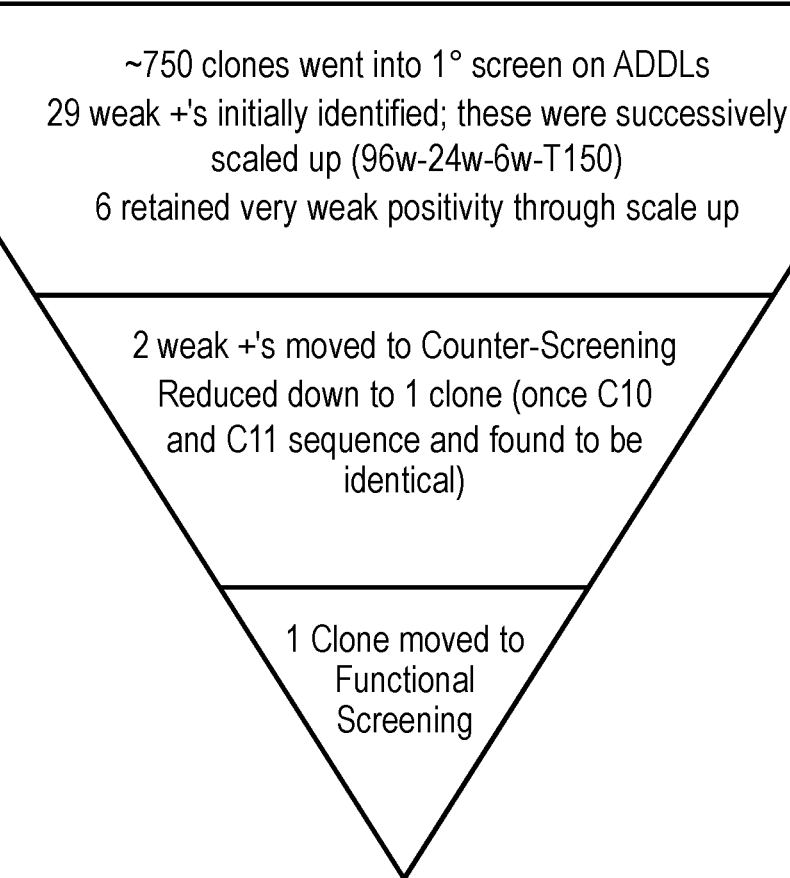
FIG. 38 summarizes the fusion C screen.

Approximately 750 clones underwent a primary screen on ADDLs. 29 weak positives were initially identified and scaled-up (96w-24w-6w-T150). 6 clones retained very weak positivity through the scale-up. 2 weakly positive clones were moved to counter-screening. The two clones were identical, so the remining clone was reformatted and produced recombinantly as hIgG1 LALA, then re-screened and re-counter-screened. The FusC screen is summarized at FIG. 38. Binding and characterization data of the lead FusC clones are depicted in FIGS. 19-29.

One clone was moved on to functional screening.

Example 5: Cellular iN Assay

Preparation of Aqueous Extracts from Human AD Brains

Frozen brain tissue was provided by the University of Miami Miller School of Medicine (Miami, FL) and Manchester Brain Bank of the Medical Research Council at University of Manchester (Manchester, UK). Brain tissue was obtained from two patients who died with mild to moderated stage AD. Aqueous extracts were prepared as described previously (Jin et al. (2018) Nature Comm. 9:2676). In brief, twenty grams of temporal cortical gray matter was Dounce-homogenized in 5 volumes of ice-cold artificial cerebrospinal fluid base buffer (aCSF-B) (124 mM NaCl, 2.8 mM KCl, 1.25 mM $NaH_2PO_4$, 26 mM $NaHCO_3$, pH 7.4) supplemented with protease inhibitors (5 mM ethylenediaminetetraacetic acid (EDTA), 1 mM ethyleneglycoltetraacetic acid, 5 µg/mL leupeptin, 5 µg/mL aprotinin, 2 µg/mL pepstatin, 120 µg/mL Pefabloc and 5 mM NaF). The resulting homogenates were centrifuged at 200,000 g for 110 minutes and 4° C. in a SW41 Ti rotor (Beckman Coulter, Fullerton, CA) and the upper 80% of the supernatant was removed and dialyzed against fresh aCSF-B, with 3 buffer changes every 24 hours over 72-hour period. Brain extracts were then divided into 2 parts: 1 portion was immunodepleted (ID) of Aβ by 3 rounds of 12 hours incubations with the anti-Aβ antibody, S97, plus Protein A sepharose (PAS) beads at 4° C. The second portion was treated in an identical manner with pre-immune serum plus PAS beads. Extracts depleted of Aβ are referred to as ID-AD and extracts treated with pre-immune serum are referred to as mock-AD. Samples were cleared of beads, and every 0.5 mL aliquots removed to low proteins binding Eppendorf tubes (Eppendorf, Hamburg, Germany) and stored at −80° C. until used. Samples were thawed once and used. Brain extract from two different cases AD10/27 and AD10/14 were used in the functional assays.

iPSC-Derived Human Neurons (iNs)

Neurogenin 2 (Ngn2)-induced human neurons (Zhang et al., 2013) were prepared as described previously (Hong et al., 2018; Jin et al., 2018). Briefly, YZ1 iPSCs were maintained in media containing DMEM/F12, Knockout Serum Replacement, penicillin/streptomycin/glutamine, MEM-NEAA, and 2-mercaptoethanol (all from Invitrogen, Carlsbad, CA) plus 10 µg/mL bFGF (Millipore, Billerica, MA). iPSCs were then plated at a density of 95,000 cells/cm$^2$ for viral infection at the following concentrations: pTet-O-NGN2-puro: 0.1 µL/50,000 cells; Tet-O-FUW-eGFP: 0.05 µL/50,000 cells; Fudelta GW-rtTA: 0.11 µL/50,000 cells (Alstem, Richmond, CA). To induce Neurogenin 2 expression, doxycycline was added on "IN day 1" at a concentration of 2 µg/mL, and puromycin was added on iN day 2 at 10 mg/ml and maintained in the media at all time thereafter. On iN day 4, cells were plated at 5,000 cells/well on Matrigel (BD Biosciences, San Jose, CA) coated Greiner 96 well microclear plates and maintained in media consisting of Neurobasal medium (Gibco), Glutamax, 20% Dextrose, MEM-NEAA and B27 with BDNF, CNTF, GDNF (PeprpTech, Rocky Hill, NJ) each at a concentration of 10 ng/ml. The neurite number and expression of neural markers reached maximal levels by iN day 14 and iNs were fully mature by iN day 21. To investigate the effects of AD brain extracts on neuritic integrity, cells were used at iN day 21.

Sample Addition and Live-Cell Imaging

At post-induction day 21, neurons were used to investigate the effects of samples on neuritic integrity using Incucyte live-imaging reader. Approximately 7 hours prior to addition of sample, images were collected from four fields per well every 2 hours for a total of 6 hours and baseline neurite length and branch points were calculated. During the last interval time, brain samples were exchanged into neurobasal medium supplemented with B27/Glutamax using PD MidiTrap G-25 columns (GE Healthcare Life Science, Milwaukee, WI). Following the 6-hour period of baseline imaging, half of the medium was removed from each well (leaving ~100 µL) and 50 µL of exchanged extract or vehicle, added along with 50 µL of fresh medium. Thereafter, images were collected from four fields per well every 2 hours for at least 72 hours. Phase contrast images sets were analyzed using IncuCyte Zoom 2016A Software (Essen Bioscience, Ann Arbor, MI). The analysis job Neural Track was used to automatically define neurite processes and cell bodies based on phase contrast images. Typical settings were: Segmentation Mode—Brightness; Segmentation Adjustment—1.2; Cell body cluster filter—minimum 500 µm2; Neurite Filtering—Best; Neurite sensitivity—0.4; Neurite Width—2 µm. Total neurite length (in millimeters) and number of branch points were quantified and normalized to the average value measured during the 6 hours period prior to sample addition. AD brain extracts (+/−immunodepletion) were added to neurons+/−test mAbs.

Neurite length at end of the 72-hour period was averaged over the last 3 time points and percent protection compared to a) no antibody condition (AD) and b) Immunodepleted brain extract (ID-AD) was calculated at each concentration. Concentration of 50% neuritotoxicity protection (EC50) was calculated.

Data Analysis and Statistical Test

For live-cell imaging experiments, samples and treatments were coded and tested in a blinded. Differences between groups were tested with two-way analysis of variance (ANOVA) with Bonferroni post-hoc tests or student's t-tests. #$p<0.05$, ##$p<0.01$, and ###$p<0.001$.

Functional Effect of Hybridoma-Purified mAbs in the Cellular iN Assay

Figure 30:
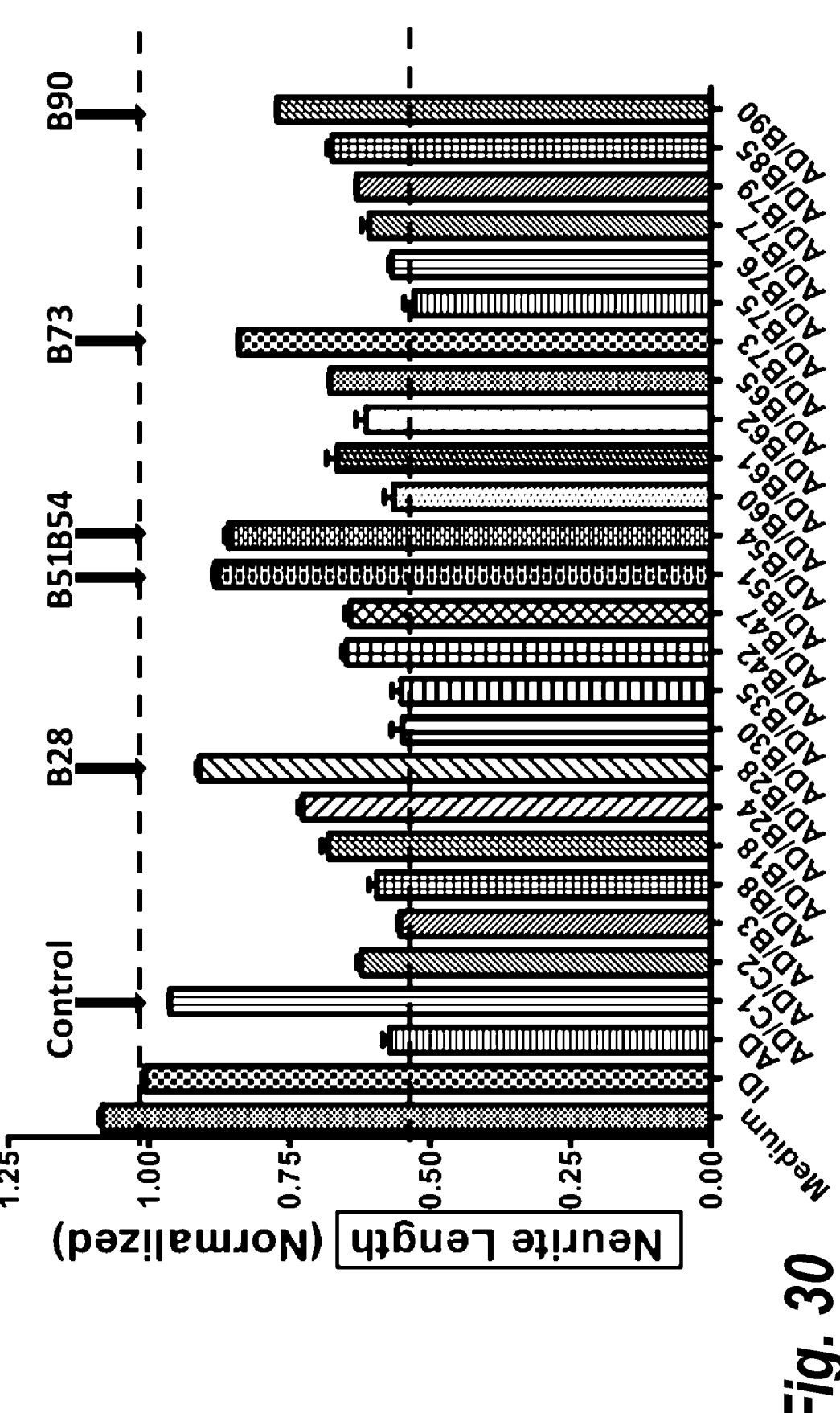
FIG. 30 depicts a test of hybridoma-purified mAbs in cellular neurite protection iN assay (run #1). iN cultures (Neurogenin-induced human neurons derived from iPSCs) were incubated with soluble AD brain extract for 72 hours in presence or absence of test antibodies (hybridoma purified preparations). Neurite length and branch points were quantified every 2 hours in Incucyte live microscopy. The bar graph shows the neurite length average of the last three time points, normalized to neurite length at baseline for each well. AD extract induced a 50% loss of neurite length, which was protected by pre-immunodepletion of Aβ from brain extract (ID) or co-incubation with control antibody 3D6 (C1), but not by an irrelevant antibody (C2), as well as by some of the novel tested antibodies described herein.

Hybridoma-purified mAbs were tested in the cellular iN assay to evaluate protection of neurite length against toxicity induced by soluble AD-brain extract. In the human neuron iN culture, continuous exposure to AD brain extract (AD10/27) led a decrease of human neurons by approximately 50% as measured after 3 days (see AD sample versus medium or ID samples in FIG. 30). Pre-Immunodepletion of Aβ from AD extract (sample ID) prevented neuritotoxicity, validating that AD brain extract contains an Aβ-dependent neurite toxic activity as previously demonstrated (Jin et al 2012; 2018). Further validation of the assay was provided by the positive control Aβ-directed antibody 3D6 at 3 µg/ml (code C1 in FIG. 30) that could neutralize the neuritotoxic brain extract as previously demonstrated (Shankar et al., 2008; Jin et al., 2011). 3D6 binds to the N-term free end of Aβ sequence and recognizes all conformations of Aβ. An additional positive control 1C22 (recognizing multiple oligomeric forms of Aβ but not monomeric Aβ, Jin et al 2018) was also used in other experiments (see Table 3). Because the exact nature of the toxic Aβ containing entity in AD brain extracts has not been characterized yet, care was taken to select a large panel of mAbs from the immunization campaigns with a broad range of affinity to soluble protofibrillar and aggregated Aβ but not binding to monomeric Aβ. This was only possible due to the good capacity/throughput of the unique cellular functional iN assay used (format multiwall MW96). Brain extract from two different preparations of the same case AD10/27 (noted AD10/27 1$^{st}$, 2$^{nd}$) were used. Several hybridoma-purified mAbs demonstrated neuroprotection similar to positive control (FIG. 30) ranging from mAbs with moderate-affinity for PF Aβ forms (such as B73 or B24), to mAbs with high-affinity to PF such as B51 or B90. However, the biochemical binding profile was not predictive of activity in the iN assay since B35 and B61 (with moderate affinity for PF Aβ forms) were inactive in the iN assay, whereas B8, B30 or B60 had very high affinity for Aβ.

TABLE 5

Summary of activity of different monoclonal antibodies in the iN neuritotoxicity protection assays.

| Binding profile | mAb tested | Experiment # | | | | | | |
|---|---|---|---|---|---|---|---|---|
| | | Run #1 and #2 | Run #3 | Run #4 | Run #5b Tox max | Run #6 26 Oct | Run #8 Nov. 9, 2018 | Run #9 Nov. 16, 2018 |
| | | Run#1 Tox ~45% Run#2 Tox ~70% | Tox ~60% | Tox ~55% | Tox ~65% Brain Extract | Tox ~70% | Tox 80% | Dilution ⅙ Tox ~75% |
| | | 10/27($1^{st}$) | 10/27 ($2^{nd}$) Sep. 20, 2018 | 10/27($2^{nd}$) Sep. 20, 2018 | 10/27($2^{nd}$) Sep. 27, 2018 | 10/27($2^{nd}$) Sep. 27, 2018 | 10/27($2^{nd}$) Nov. 1, 2018 | 10/27 ($2^{nd}$) Nov. 1, 2018 |
| NA | Anti-TNP | Neg (C2) | negative (C1) | | Negative (R6) | Negative (R2) | Neg. (A8) | Neg (2x) A3 A10 |
| M + PF | 3D6 | Active, (C1), | Active (C3 &C4) | NT | NT | Active (R1) | | |
| PF >> M | 1C22 | NT | Active (C2) | Active (R2) | Active (R8) | | | Active (A9) |
| PF >> M | B30 | Neg | Partial active (A11) | Active (R3) | Very modest(R9) | Active (A3) recombinant | | |
| Weak on PF but > M | B75 | Neg | NT | Active (R4) | Most Active (R7) | NT | Modest act (A11) hybrid | |
| PF >> M | B19 reprep (=B24) | Not yet available | Negative (A1) | NT | NT | NT | | |
| PF >> M | B24 | Active 2x (May prep and July re-prep) | Partial active (A12) | Active (R5) | Very weak active (R1) | Modest activity (A1) recombinant | Modest (A6) recombinant | |
| PF >> M | B28 | Active 2x (May prep and July re-prep) | Partial active (A13) | Negative *(pSEC) | ~Negative (R5)*(pSEC) | Modest activity (A2) recombinant | Active (A5) recombinant | |
| PF >> M | B51 | Active 2x (But = identical to B60 inactive) | Partial active (A14) | NT | NT | Active (A4) recombinant | Active (A4) recombinant | |
| PF >> M | B54 | Active 2x (two preps) | Negative (A15) | NT | NT | Most Active recombinant | Active recombinant | |
| PF >> M | B73 | Active 2x (two preps) | Active (A16) | NT | NT | Most Active recombinant | Active recombinant | |
| PF >> M | B90 | Active 2x (two preps) | Active (A17) | Partial active (R7) *(pSEC) | Partial active (R4) *(pSEC) | Very modest (A6) recombinant | Very modest (A1) recombinant | |
| No binding to PF, ADDL, or M | C10 | Active | Negative (A8) July prep | Negative (R8) July prep | ~Negative (R2) July prep | Most Active (A9); *new prep | | |
| No binding to PF, ADDL, or M | C11 | Most Active | Negative (A9) July prep | Partial active July prep | ~Negative (R3) *3 mo old prep from July | Most Active (A10); new prep | Active (A10); new prep | Hybridoma: partial (A4) Recombin: Neg (A5) |

The iN functional assay using AD brain extract represents, therefore, a unique tool to characterize and select novel Aβ mAbs with highly relevant biological activity. Due to the sensitivity of the iN assay, several independent experiments were conducted to confirm the data, including experiments using antibodies issued from additional fusions (see Table 5).

The neuroprotective effect by different antibodies was somewhat variable among experiments, in part, due to moderate stability of the antibody batches purified from hybridoma or to the limited stock concentration of those antibodies that led to only limited dilution in the media of iN cells that compromised cell viability. In some instances, independent antibody production batches had to be generated. For example, hybridoma B28 was only modestly active in run #3 and negative in Runs #4 and 5b, potentially due to stability issues. Also unexpected was clone B73, which was initially negative in the iN runs with the first hybridoma production, but for which a second preparation provided very significant activity in runs #4 and 5b.

For further analysis with a recombinant version of the hybridoma clones that enabled the transfer all mAbs to the same IgG1 LALA framework and enabled more controlled production conditions, clones were selected that offered neuroprotection in at least one iN experiment run, but with diverse affinity to synthetic Aβ conformers, in particular, those with low affinity for protofibrillar and fully aggregated synthetic Aβ preparations (in addition to low/no affinity for monomeric Aβ).

Functional Effect of Recombinant mAbs in the Cellular iN Assay

Figure 31A:
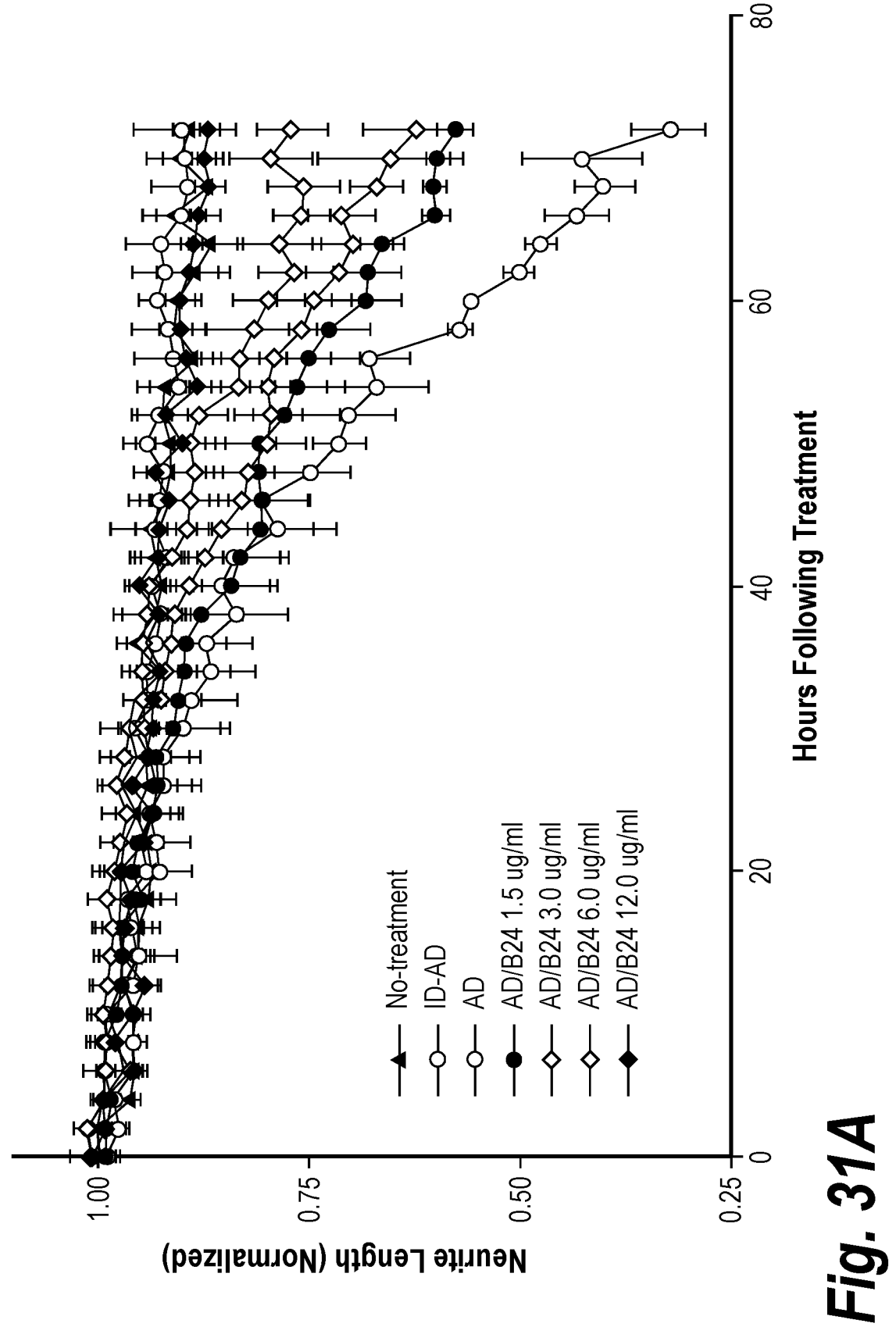
FIG. 31A-FIG. 31C depict a test of recombinant rB24 and rB75 in cellular neurite protection iN assay. iN cultures were incubated with AD brain extract for 72 hours in the presence or absence of test antibodies (recombinant rB24 and rB75 preparations). Neurite length and numbers were quantified every 2 hours in Incucyte live microscopy, and were normalized to baseline values for each well. The entire time course analysis of normalized neurite length is presented to exemplify the time-dependent neuritotoxicity of AD brain extract, and the concentration-dependent protection provided by recombinant antibodies (rB24 (A) and rB75 (B)). Using the average of the last three time points, a concentration of 50% neuritotoxicity protection (EC50) was determined for each antibody in comparison to the reference antibody 1C22 (C).
Figure 31B:
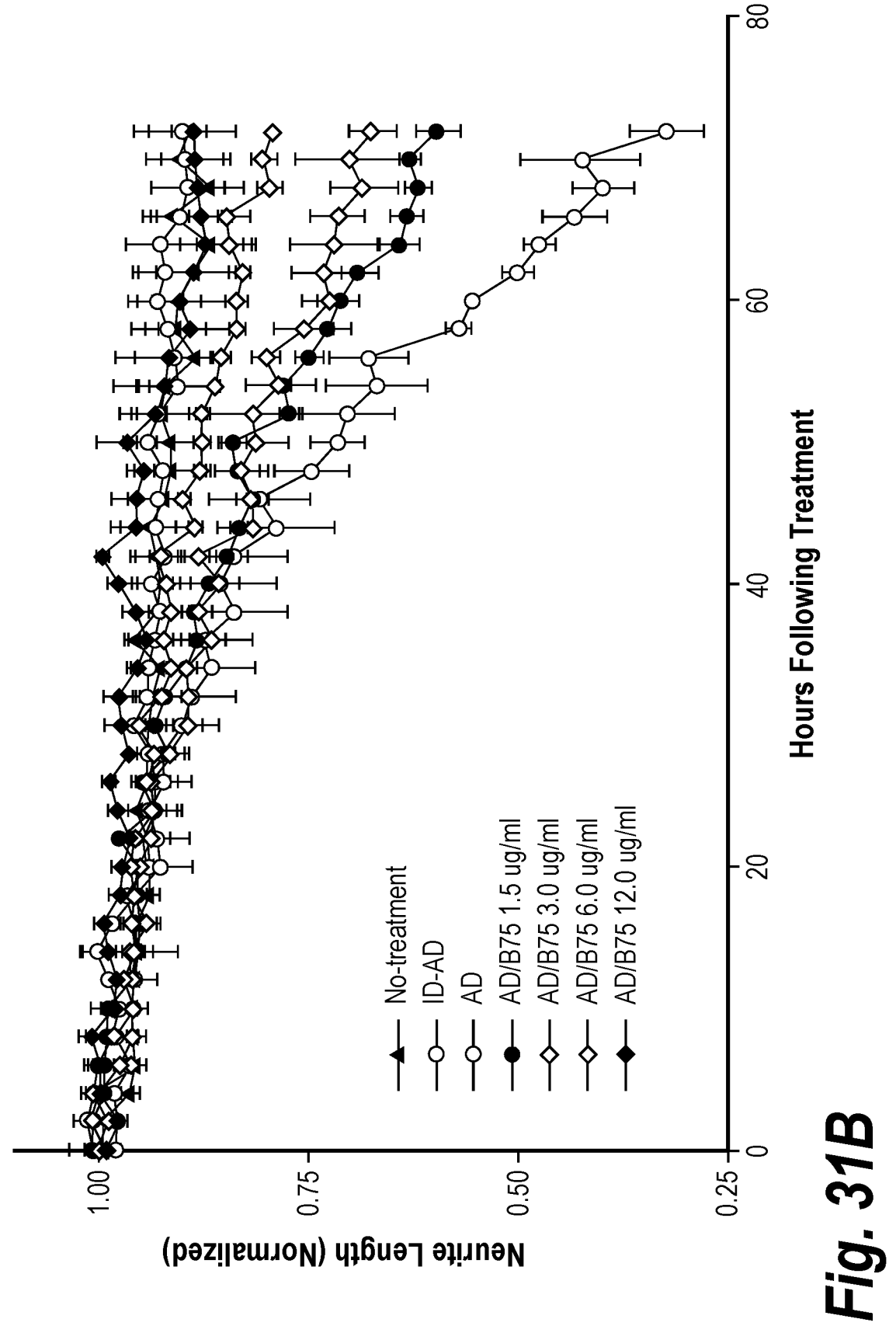
Figure 31C:
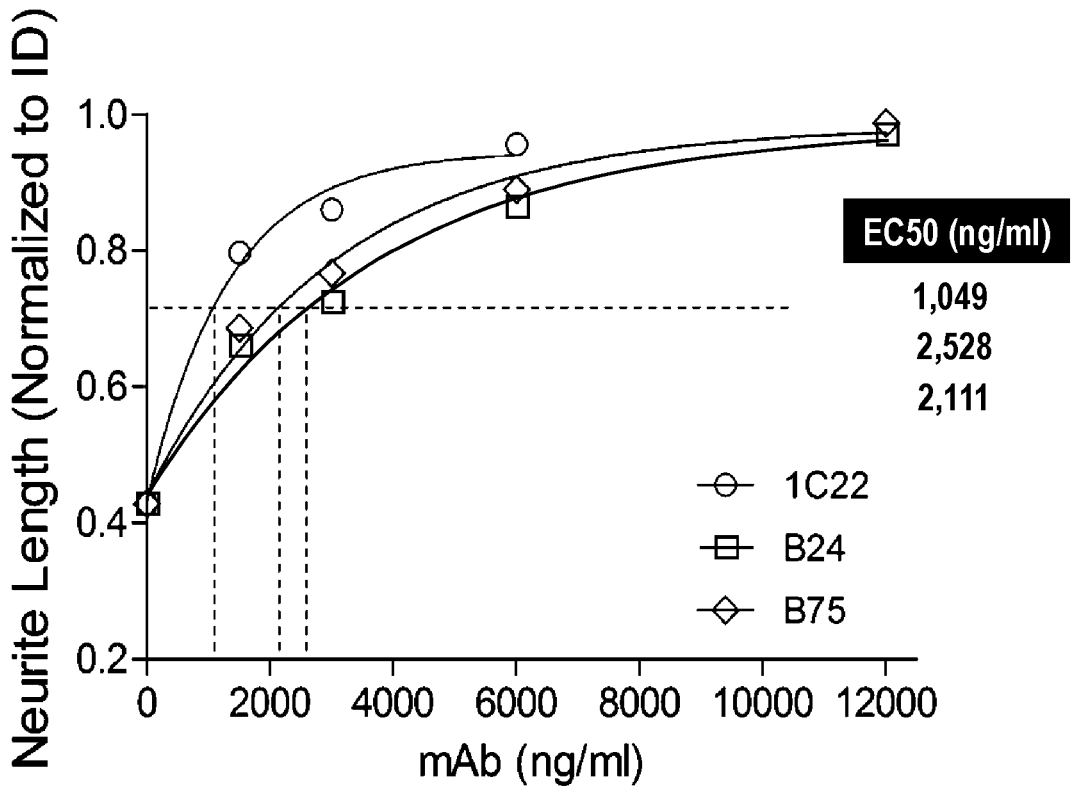
Figure 32A:
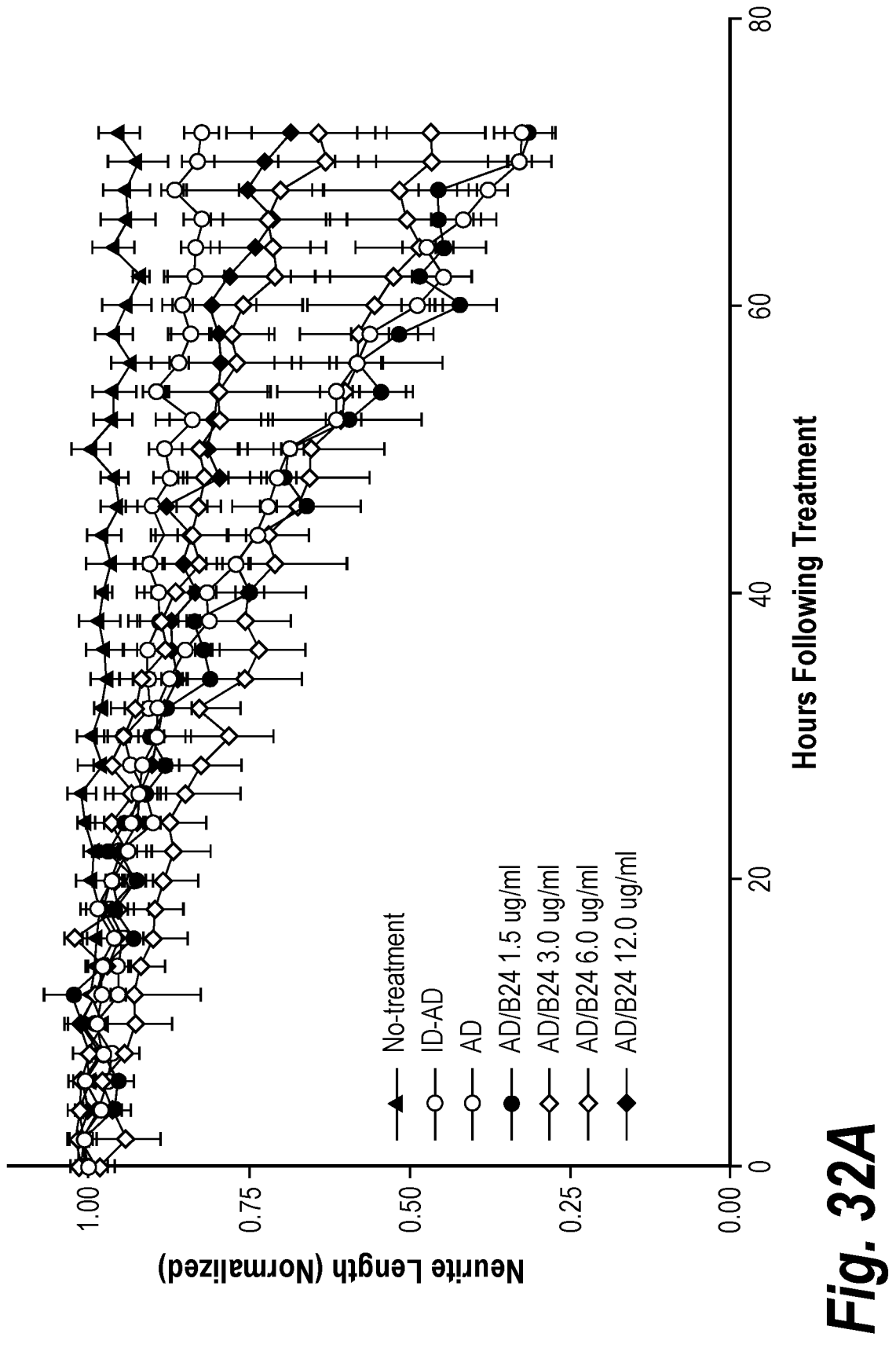
FIG. 32A-FIG. 32C depict a test of recombinant rB24 and rC11 in a cellular neurite protection iN assay. iN cultures were incubated with AD brain extract for 72 hours in the presence or absence of test antibodies (recombinant rB24 and rC11 preparations). Neurite length and numbers were quantified every 2 hours in Incucyte live microscopy, and were normalized to base line values for each well. The entire time course analysis of normalized neurite length is presented to exemplify the time-dependent neuritotoxicity of AD brain extract and the concentration-dependent protection provided by recombinant antibodies (rB24 (A), rC11 (B)). Using the average of the last three time points, a concentration of 50% neuritotoxicity protection (EC50) was determined for each antibody in comparison to the reference antibody 1C22 (C).
Figure 32B:
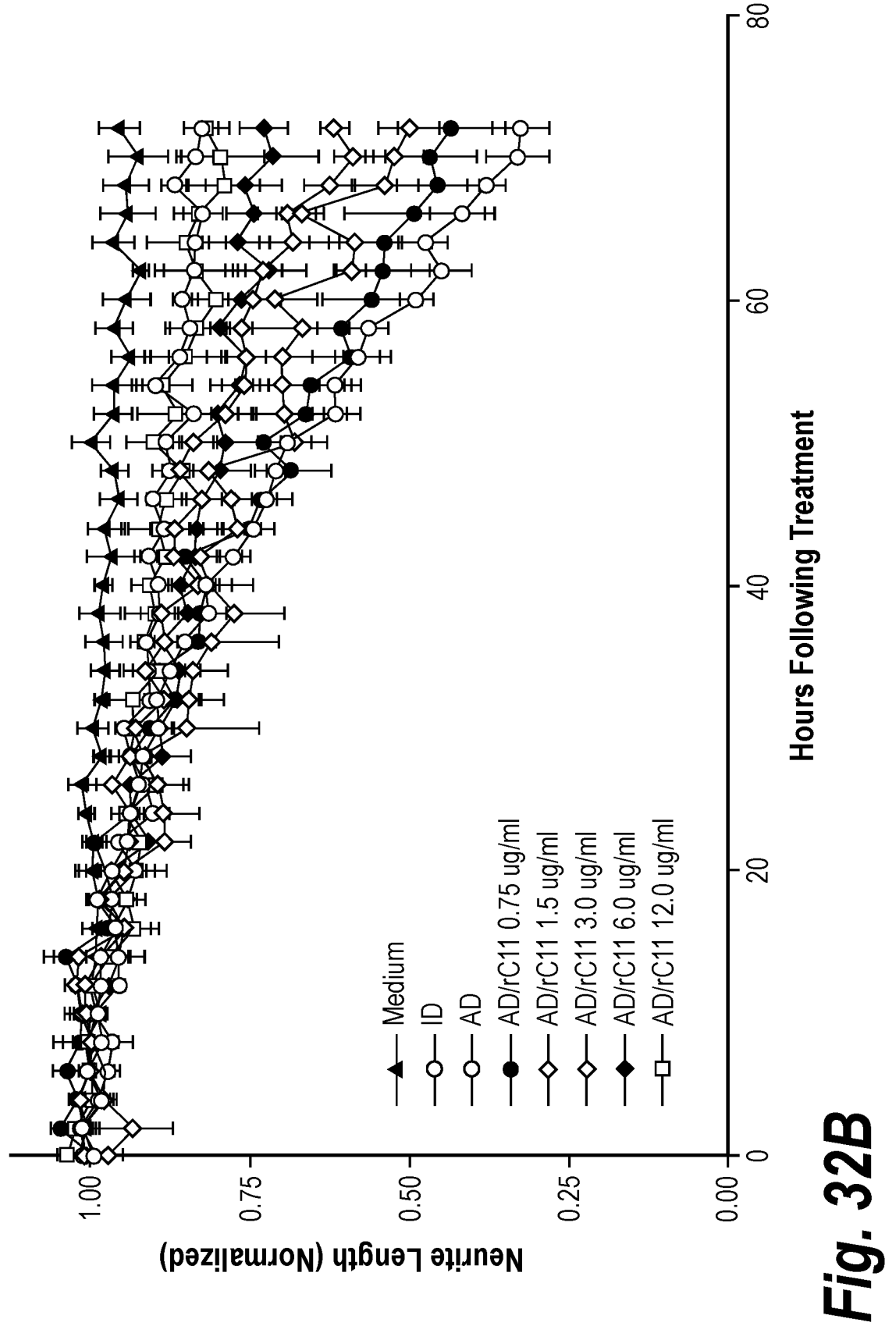
Figure 32C:
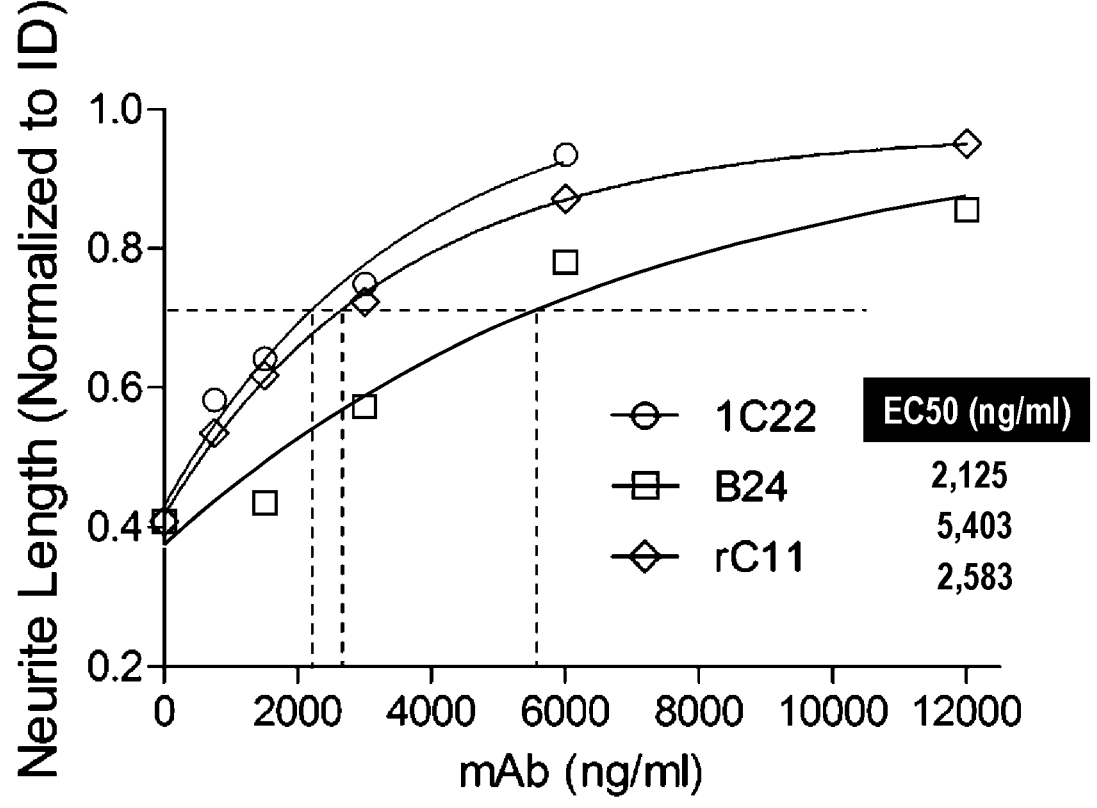
Figure 33A:
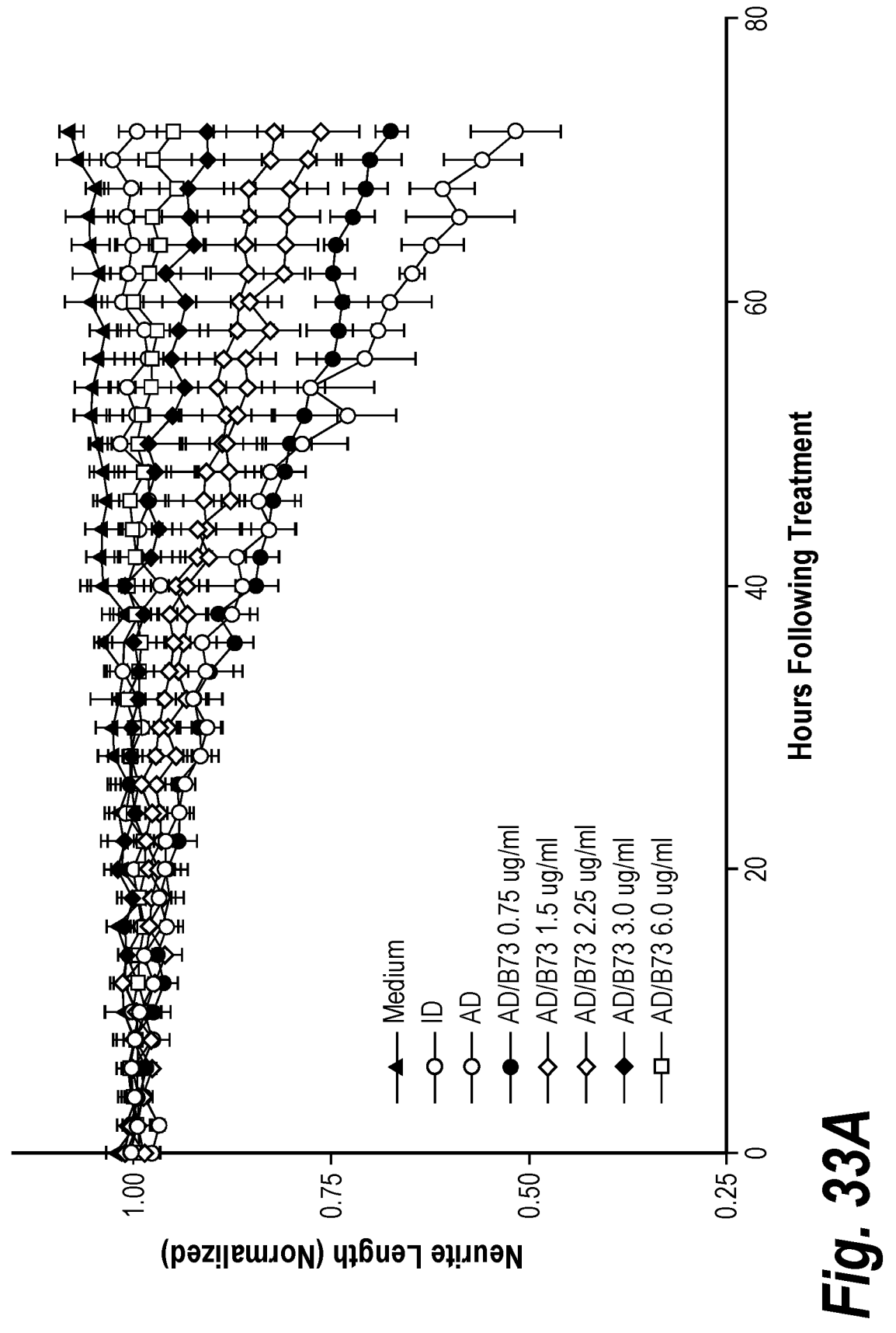
FIG. 33A-FIG. 33C depict a test of recombinant rB73 and rB28 in a cellular neurite protection iN assay. iN cultures were incubated with soluble AD brain extract for 72 hours in the presence or absence of test antibodies (recombinant rB73 and rB28 preparations). Neurite length and numbers were quantified every 2 hours in Incucyte live microscopy, and were normalized to base line values for each well. The entire time course analysis of normalized neurite length is presented to exemplify the time-dependent neuritotoxicity of AD brain extract and the concentration-dependent protection provided by recombinant antibodies (rB73 (A), rB28 (B)). Using the average of the last three time points, a concentration of 50% neuritotoxicity protection (EC50) was determined for each antibody in comparison to the reference antibody 1C22 (C).
Figure 33B:
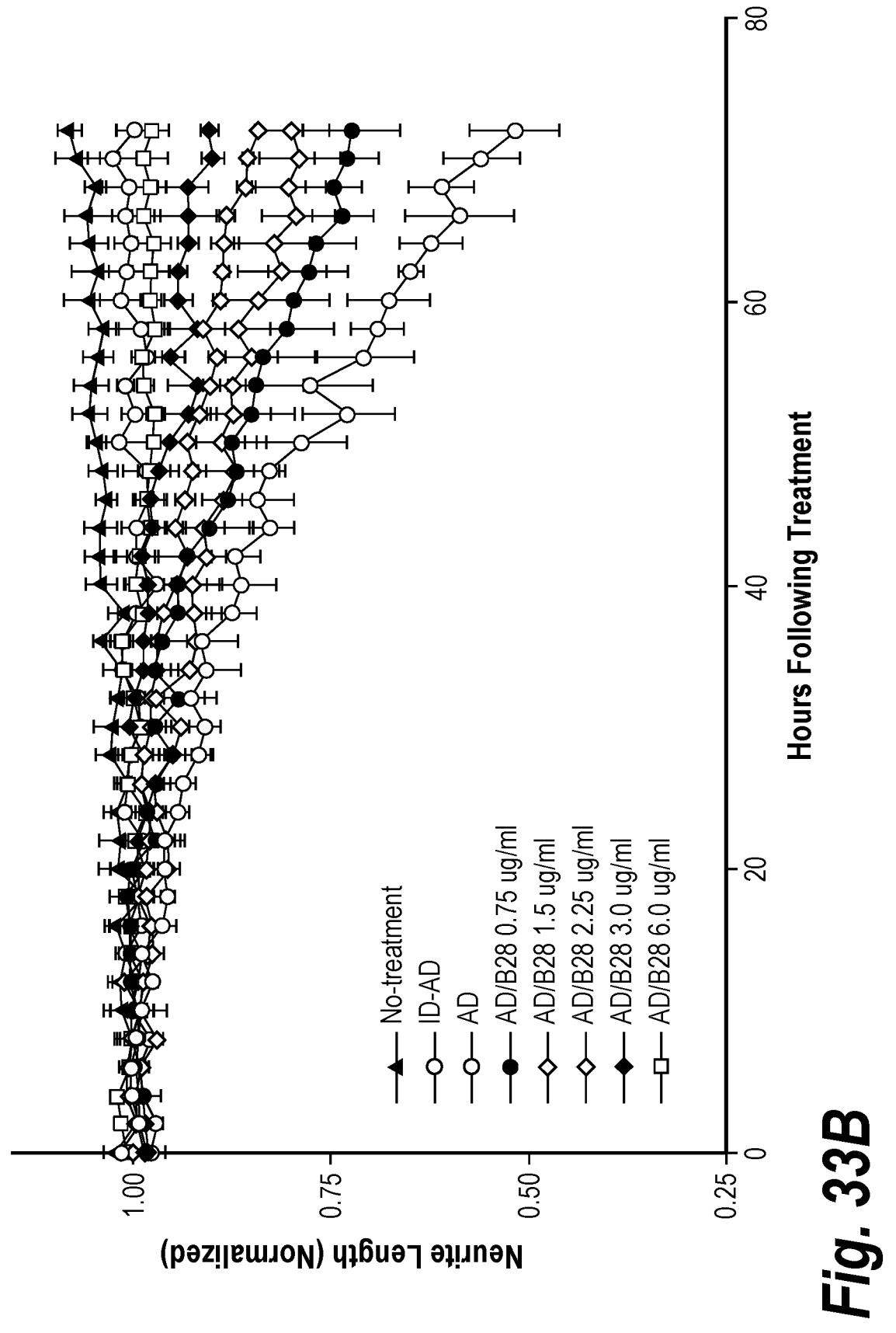
Figure 33C:
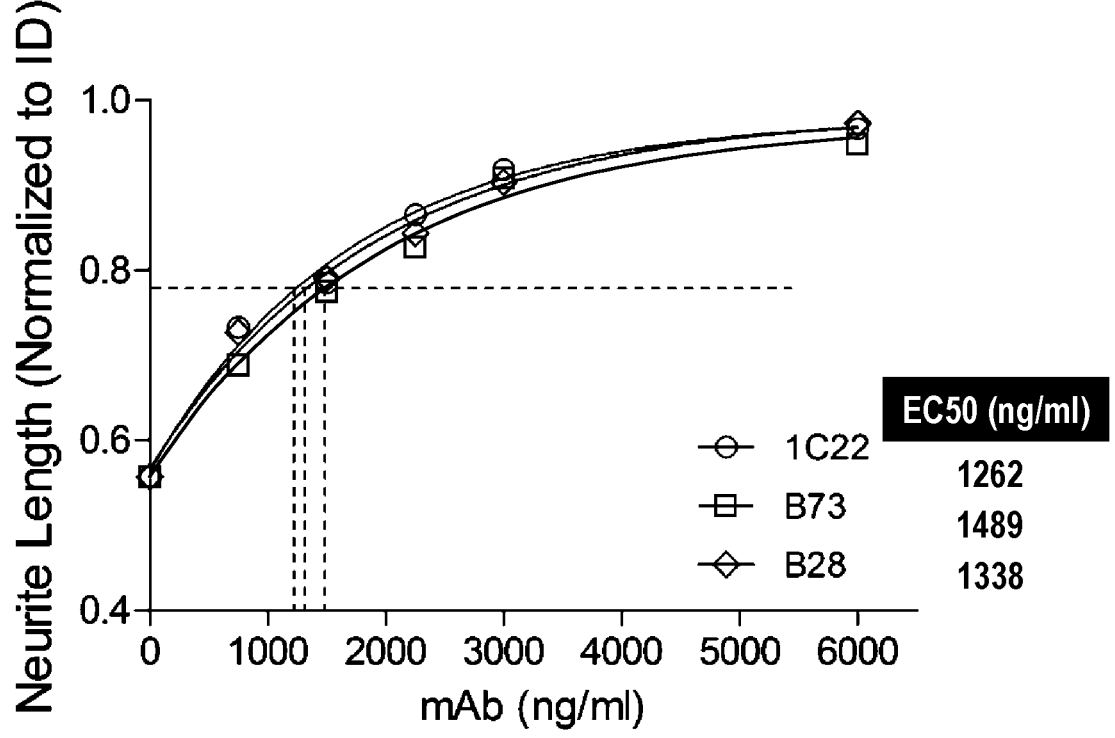

Recombinant versions of selected mAbs were produced at high stock concentrations (>2 mg/ml) and tested in the cellular iN assay. For each mAb, using brain extract AD10/27, a first test at one mAb concentration (3 μg/ml in well) was performed to confirm neurite protection previously observed with hybridoma-purified versions (Table 5, runs #6, 8 and 9). Based on the uniqueness of biochemical binding profile (as low as possible affinity for the classical synthetic forms of Aβ but very significant protection against Aβ Ad brain extract), for the most interesting mAbs, a complete concentration response curve was performed using a separate brain extract AD10/14. It was important to establish that the neuroprotective activity the mAbs could be also observed in separate AD case extracts. mAbs were tested at concentrations ranging from 0.75 up to 6 or to 12 µg/ml. As an example, full time-course results of mAbs rB24 and rB75 compared to positive control 1C22 is illustrated in FIG. 31, upper and middle panels, respectively, demonstrating a concentration-dependent protection over neuritic loss induced by AD brain extract AD10/14 by rB24 and rB75, respectively. Concentration of 50% neuritotoxicity protection (EC50) was determined as 2,528 and 2,111 ng/ml for rB24 and rB75 respectively as compared to 1,049 for the positive control 1C22 (FIG. 31, lower panel). Comparable data are provided for the pair rC11 and rB24 in FIG. 32 and for the pair rB73 and rB28 in FIG. 33.

Multiple experiments were conducted with two to three mAbs always in comparison to positive control 1C22, and the EC50 results are summarized in Table 6. All selected recombinant mAbs were within a two-fold level of activity of 1C22.

µg/ml. When testing AD extract, the control group, AD extracts group and the antibodies+AD extract conditions were randomly chosen to avoid any slice quality issue. Each mouse was checked for every day recording to confirm that all brain slices were good for responding to antibodies or AD extract. If the slices showed a small or no LTP in testing condition, the data from that mouse would not be used. 1) For the antibody alone condition, antibody was added to the 10 mL perfusion ACSF with recording for at least 30 minutes to ensure that the baseline was stable, and then the high-frequency stimulation (HFS) was applied. After the stimulation, recordings were continued for another 60 minutes. 2) For the antibodies plus AD extract experiments, both antibodies and AD extract (AD10/14, dilution 1/20) were thawed at room temperature, and then gently vortexed. Each antibody was mixed with AD extract aliquots (0.5 ml) and gently shaking for 60 minutes before added to the 9.5 mL perfusion ACSF (total volume brought up to 10 mL).

TABLE 6

| | Neuroprotective activity of selected recombinant antibodies in the iN cellular assay (EC50 values expressed in ng/ml). | | | | | | | | |
|---|---|---|---|---|---|---|---|---|---|
| EC50 ng/ml | Run10 | Run11 | Run12 | Run13 | Run14 | Run15 | Run16 | Run17 | Mean |
| 1C22 | 1662 | 1729 | 1262 | 1141 | 1744 | 1049 | 2700 | 2125 | 1677 ± 549 |
| rB73 | 1982 | 1969 | 1489 | | 2318 (2$^{nd}$ prep) | | | | 1940 ± 341 |
| rB28 | At 3 µg/ml ~1C22 | 1756 | 1338 | 1499 | At 3 µg/ml ~1C22 | | | | 1531 ± 211 |
| hB75 | | | | 2051 | | | | | 2051 |
| rB75 | | | | | At 3 µg/ml ~rB24 | 2111 | 6042 | | 4077 ± 2780 |
| rB24 | | | | | ~3-6 µg/ml (3 conc only) | 2528 | | 5403 | 3966 ± 2033 |
| rC11 | | | | | | | 3583 2188 | 2583 | 2785 ± 719 |

Example 6: Long-Term Potentiation Electrophysiology Functional Assay to Demonstrate Protection Against Soluble AD Brain Extracts Preparation of Aqueous Extracts from Human AD Brains Preparation of aqueous extracts from human AD brains was performed as above for the functional cellular iN assay. The samples were thawed only once and used. Brain extract from AD case AD10/14 was used in the long-term potentiation (LTP) assay.

Electrophysiology Recordings and Test of Protection by Antibodies

Hippocampal LTP recordings were performed similar to a previous method (Shankar et al. (2008) Nat. Med. 14 (8): 837-842; Li et al. (2011) J. Neurosci. 31 (18): 6627-6638; Li et al. (2018) Acta Neuropathol. Commun. 6 (1): 121) using adult mouse (2 to 3 months old, both genders) brain slices (350 µm thicknesses). Recording was performed for the stratum radiatum of the hippocampal CA1 region, and the stimulation electrode was placed on Schaffer collaterals using microelectrode array (MEA). The MED64 recording system (Alpha MED Scientific, Japan) was used for extracellular field potential recordings. There was an array of 64 planar microelectrodes in the MED64 probe (P515A), arranged in an 8×8 pattern, with an interpolar distance of 150 µm (Liu et al. (2011) Brain Res. 1382:57). Antibodies (C11, B24, B28, B73, and B75) were added to perfusion artificial cerebrospinal fluid (ACSF) at a concentration of 5

Data Analysis and Statistical Test

Samples and treatments were coded and tested in a blinded fashion. Values of EPSP slope at 60 minutes post-HFS were quantified versus baseline per brain section and mean calculated for each antibody (number of brain slices per antibody/conditions in figure legend). Differences among the groups were tested with two-way analysis of variance (ANOVA) with Bonferroni post-hoc tests or student's t-tests. #$p<0.05$, ##$p<0.01$, and ###$p<0.001$.

Test of Selected Human Recombinant mAb in Electrophysiological Assay

Figure 34A:
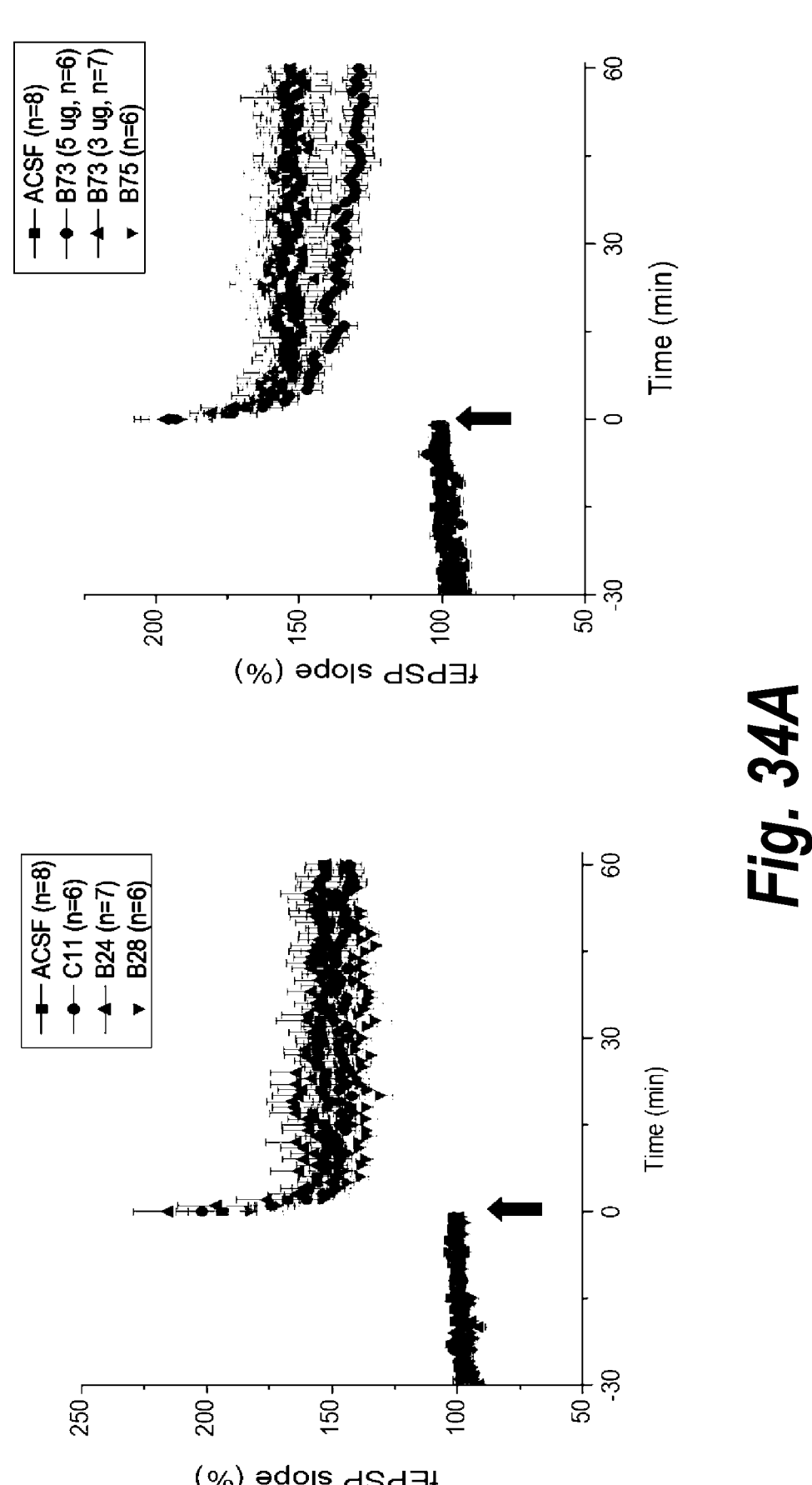
FIG. 34A-FIG. 34B depict the effect of selected antibodies on electrophysiology recordings in rodent brain slices in basal conditions. Synaptic transmission (fEPSP slope) was recorded in wild-type brain slices at baseline and after high-frequency stimulus (arrow), all values normalized to baseline transmission. Selected antibodies were added to the brain slices at the final concentration of 5 µg/ml, except for B73 where a second concentration was also tested. (A) Full-time recordings averaged by conditions. Four conditions represented in both left and right panels of the figure. (B) Analysis of synaptic transmission at end point (60 minutes post-HFS) under the different conditions. The number of slices recorded per condition were: ACSF (n=8), C11 (n=6), B24 (n=7), B28 (n=6), B73 (n=6 at 5 µg/ml and n=7 at 3 µg/ml) and B75 (n=6). Differences among groups were tested with two-way analysis of variance (ANOVA) with Bonferroni post-hoc tests or student's t-tests. ##p<0.01.
Figure 34B:
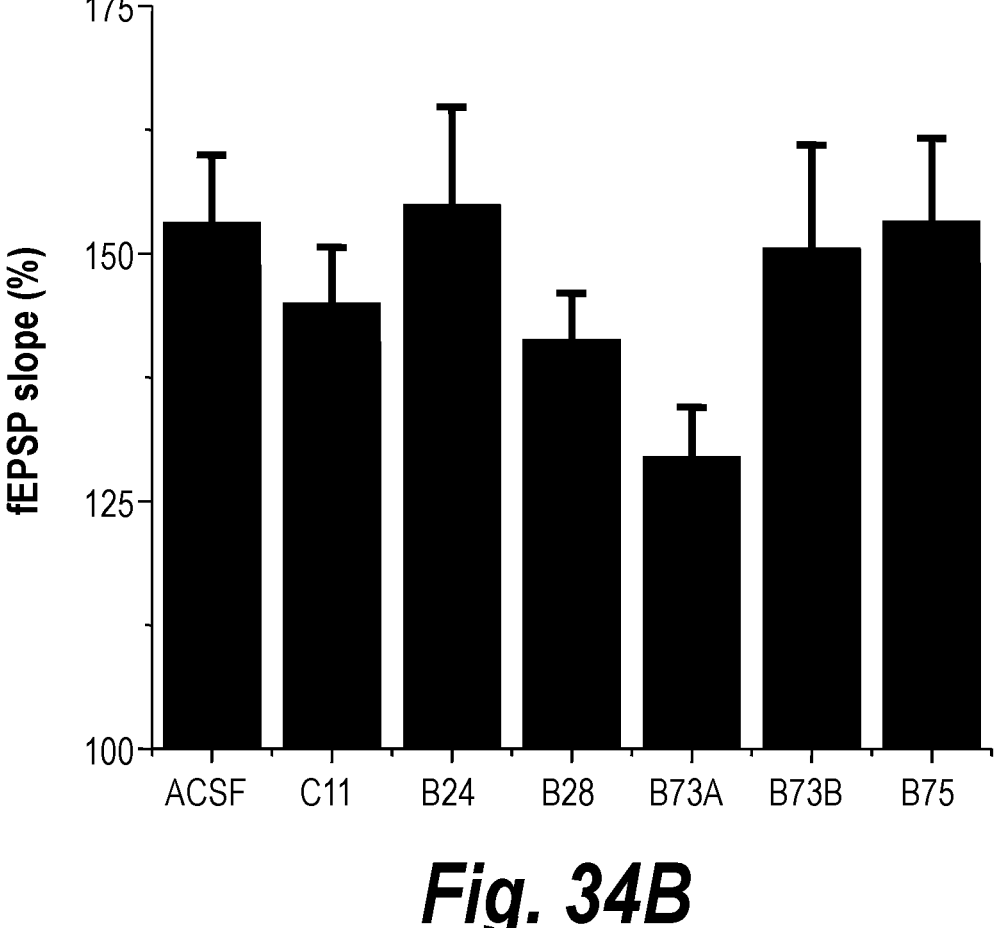

Hippocampal long-term potentiation (LTP) recordings were performed to analyze synaptic plasticity in brain sections, a model considered to represent memory encryption. It had been previously shown that AD soluble brain extracts contain an Aβ-dependent activity potently inhibiting induction of LTP by HFS in rodent brain slices (Shankar, G. M. et al. 2008, Hong, W. et al., 2018). First, the effect of selected antibodies (C11, B24, B28, B73 and B75) on basal LTP was investigated. Antibodies were added to perfusion ACSF at the concentration of 5 g/ml final concentration in ACSF. At this concentration, C11, B24, B28 and B75 did not affect basal transmission or LTP induction by HFS (FIG. 34A, FIG. 34B), while B73 significantly decreased it. B73, at the lower concentration of 3 µg/ml, did not affect LTP induction and was used thereafter.

Figure 35A:
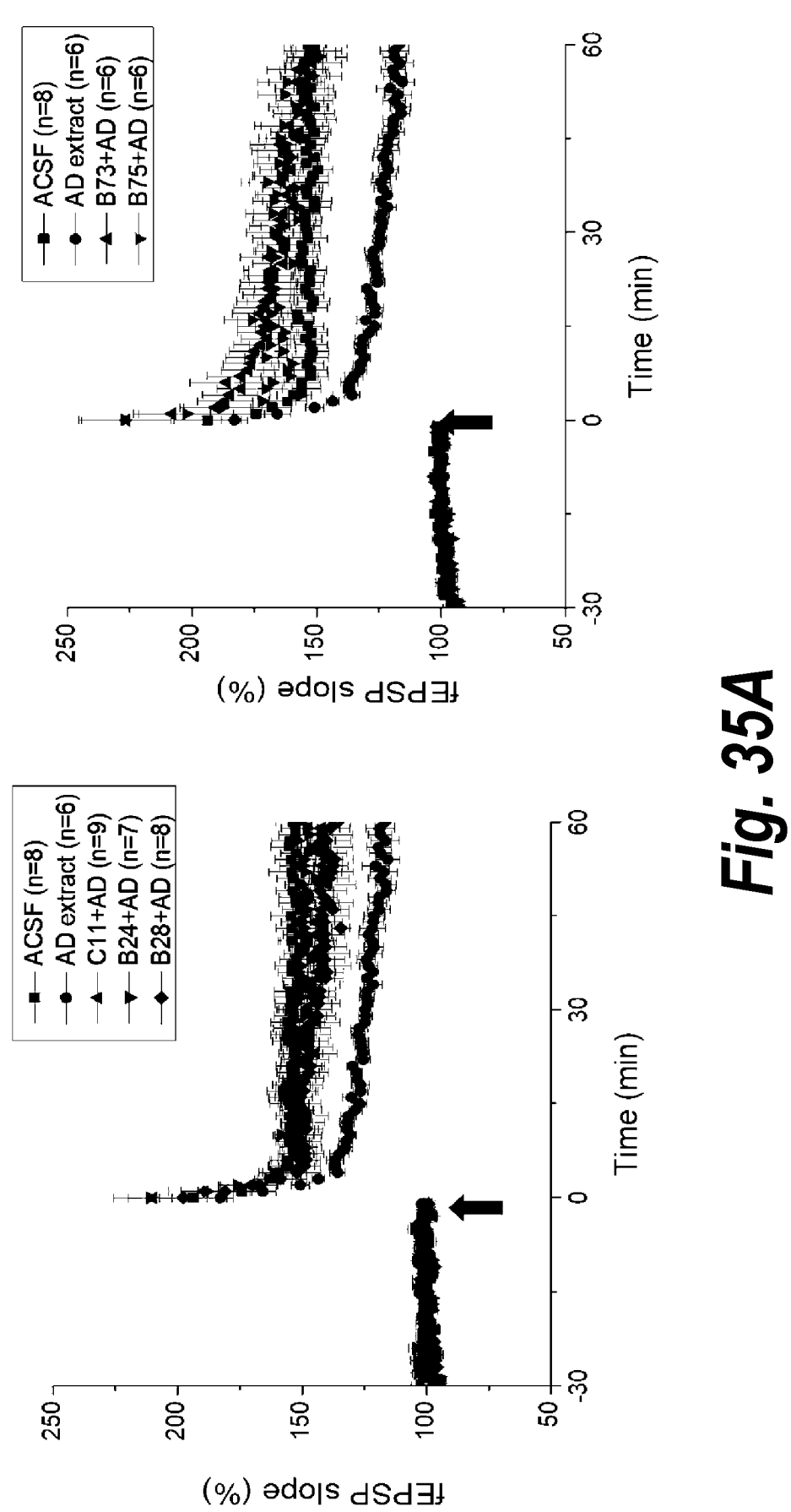
FIG. 35A-FIG. 35B depict the ability of selected antibodies to neutralize the inhibitory effect of AD brain extract on synaptic plasticity in wild-type mouse brain slices. Synaptic transmission (fEPSP slope) was recorded in brain slices at baseline and after a high-frequency electrical stimulus (arrow), all values normalized to baseline transmission. AD brain extract was added to brain slices alone or after pre-incubation with selected mAbs at the final concentration of 5 µg/ml, except for B73 which was used at 3 µg/ml. (A) Full-time recordings averaged by conditions showed the strong inhibitory effect of AD extract on induction of LTP. (B) Analysis of synaptic transmission at end-point (60 minutes post-HFS) under different conditions. Pre-incubation of AD brain extract with the different antibodies led to a very significant increase of fEPSP potentiation back to values with ACSF alone (Figure x+1, A and B). Remarkably, B75 at 5 µg/ml and B73 at 3 µg/ml led both to a full rescue of the AD brain extract inhibitory effect on LTP. The number of slices recorded per conditions were: AD brain extract (n=6), AD extract plus C11 (n=9), plus B24 (n=7), B28 (n=8), plus B73 (n=6 at 3 µg/ml) and plus B75 (n=6). Differences among groups were tested with two-way analysis of variance (ANOVA) with Bonferroni post-hoc tests or student's t-tests. #p<0.05, ##p<0.01, and ###p<0.001.
Figure 35B:
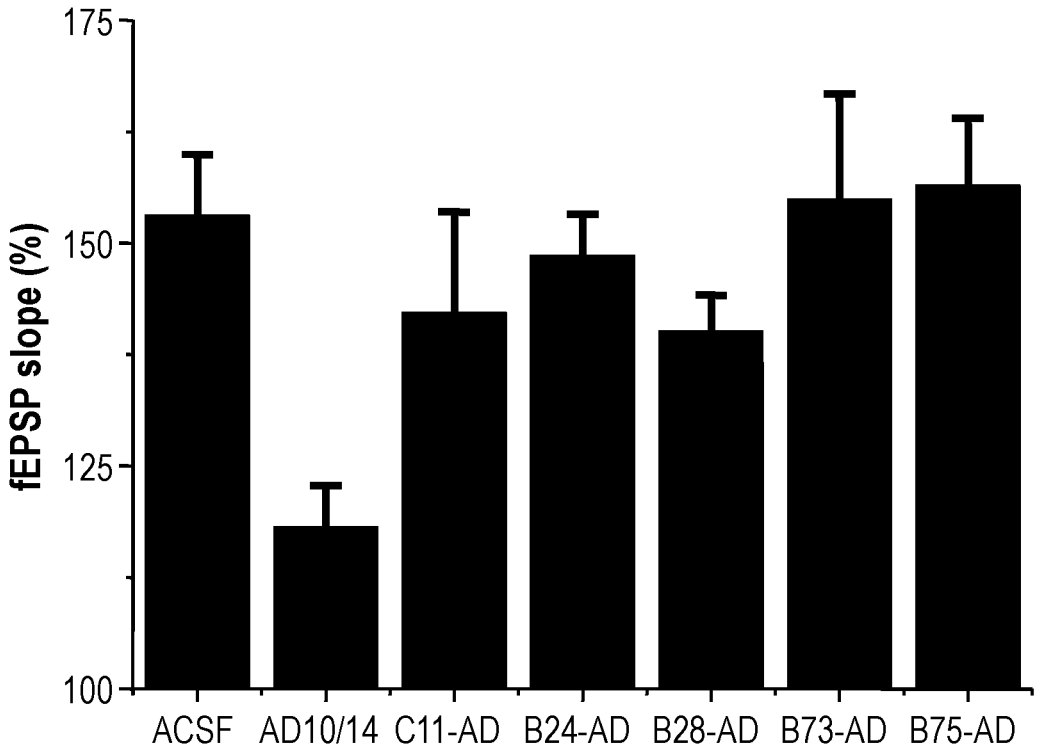

The different antibodies were next tested (5 µg/ml except B73 at 3 µg/ml) to analyze whether they could prevent the inhibitory effect of AD brain extract on induction of LTP. As can be observed in FIG. 35A and FIG. 35B, in the presence of AD brain extract AD10/14, the potentiation of EPSP 1 hour post-HFS was only 120% of baseline as compared to 150% with ACSF alone (FIG. 34), confirming inhibitory activity of AD brain extract. Pre-incubation of AD brain extract with the different antibodies led to a very significantly higher EPSP potentiation levels back to ACSF alone values (FIG. 35A, FIG. 35B, p values lower than 0.05). Most remarkably, B75 at 5 μg/ml and B73 at 3 μg/ml led both to a full rescue of the AD brain extract inhibitory effect on LTP. Therefore, it can be concluded that, the antibodies described herein are able to neutralize the LTP inhibitory activity present in AD brain extract, in addition to their protective effect observed in human neuronal cultures.

Figure 36A:
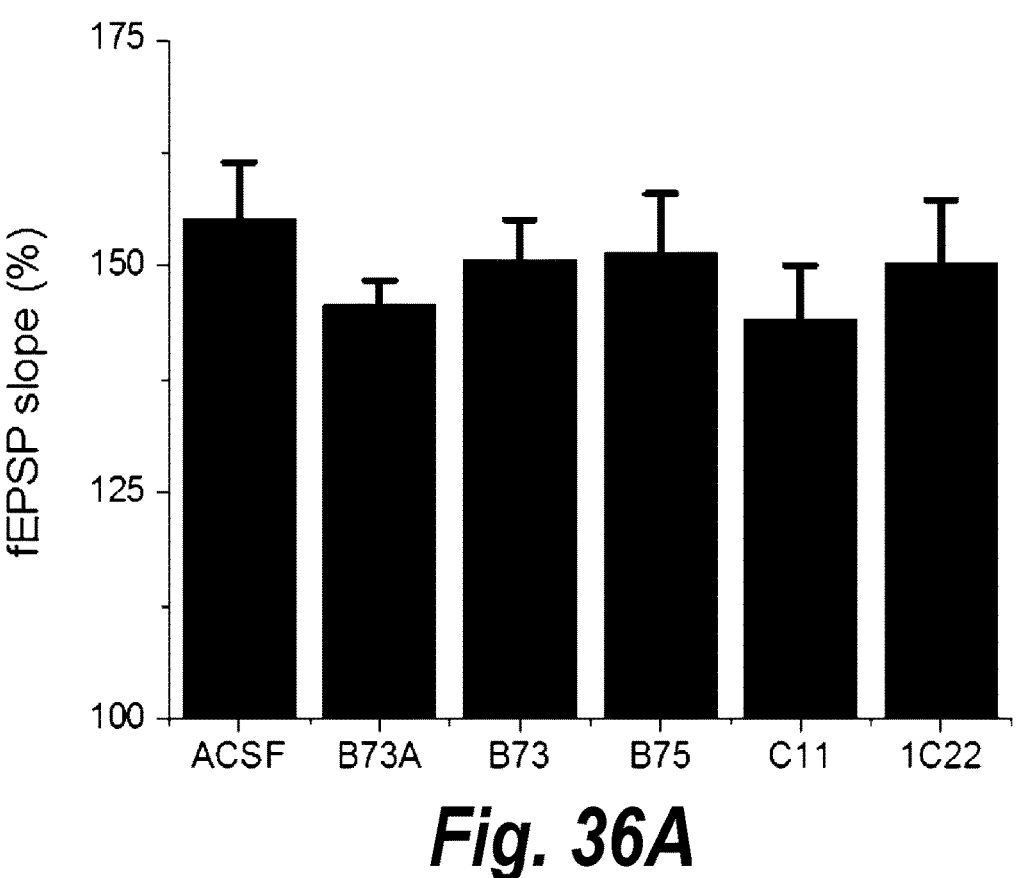
FIG. 36A-FIG. 36B depict the ability of selected antibodies to neutralize the inhibitory effect of AD brain extract on synaptic plasticity in brain slices at a lower concentration. Synaptic transmission (fEPSP stope) was recorded in brain slices at baseline and after high-frequency stimulus, all values normalized to baseline transmission as described above. A) None of the antibodies tested (at 2 µg/ml) had any effect on basal synaptic transmission and induction of LTP in basal conditions. B) Antibodies were tested in presence of AD brain extract (after pre-incubation as described above). B73 retained almost full prevention of AD brain extract effect (p values lower than 0.05). C11 also significantly prevented AD brain extract effect by well over 50% (p values lower than 0.01) and both compared favorably with the reference antibody 1C22. B75 was not significantly effective at this lower concentration.
Figure 36B:
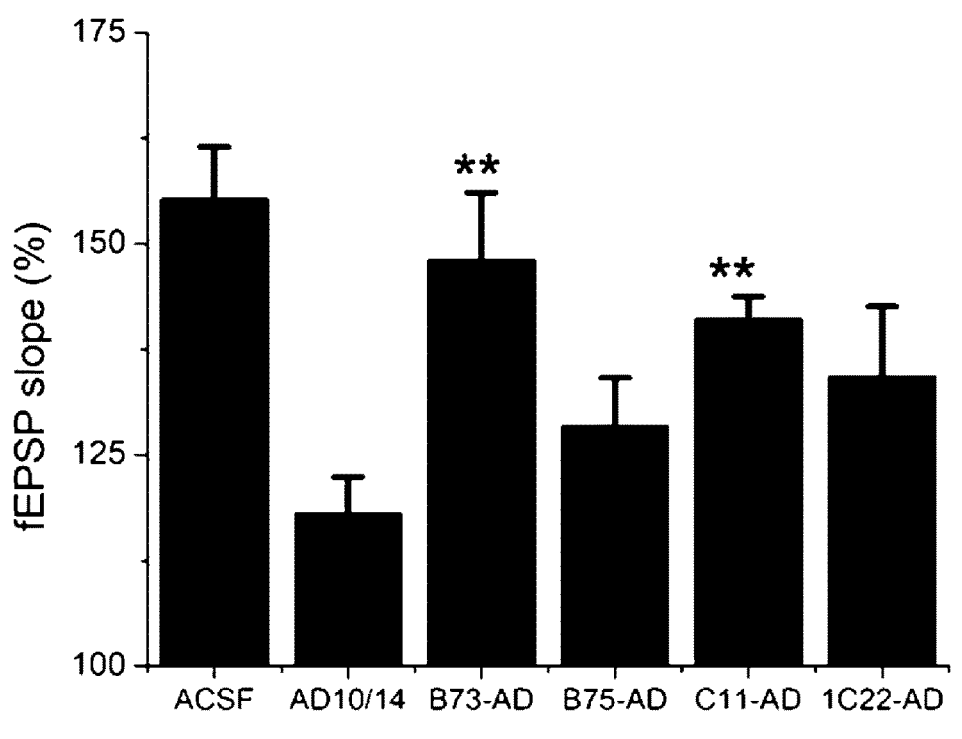

The best performing antibodies, B73, B75 and C11, were next tested at a lower concentration of 2 μg/ml, and compared to reference antibody 1C22 (FIG. 36A and FIG. 36B). A new batch of B73 was used for this experiment. It was confirmed that at these low concentrations, none of the antibodies affected basal transmission or LTP induction by HFS (FIG. 36A). The antibodies were next tested (at 2 μg/ml) for preventing the inhibitory effect of AD brain extract on LTP induction. At this concentration, B73 retained almost full prevention of AD brain extract effect on LTP (FIG. 36B, p values lower than 0.05), in line with the previous data obtained at 3 μg/ml. C11 also significantly prevented AD brain extract effect by well over 50% (p values lower than 0.01), and both compared favorably with the reference antibody 1C22. B75 was not significantly effective at this lower concentration. These data confirm and extend the electrophysiology results discussed Supra.

Figure 39A:
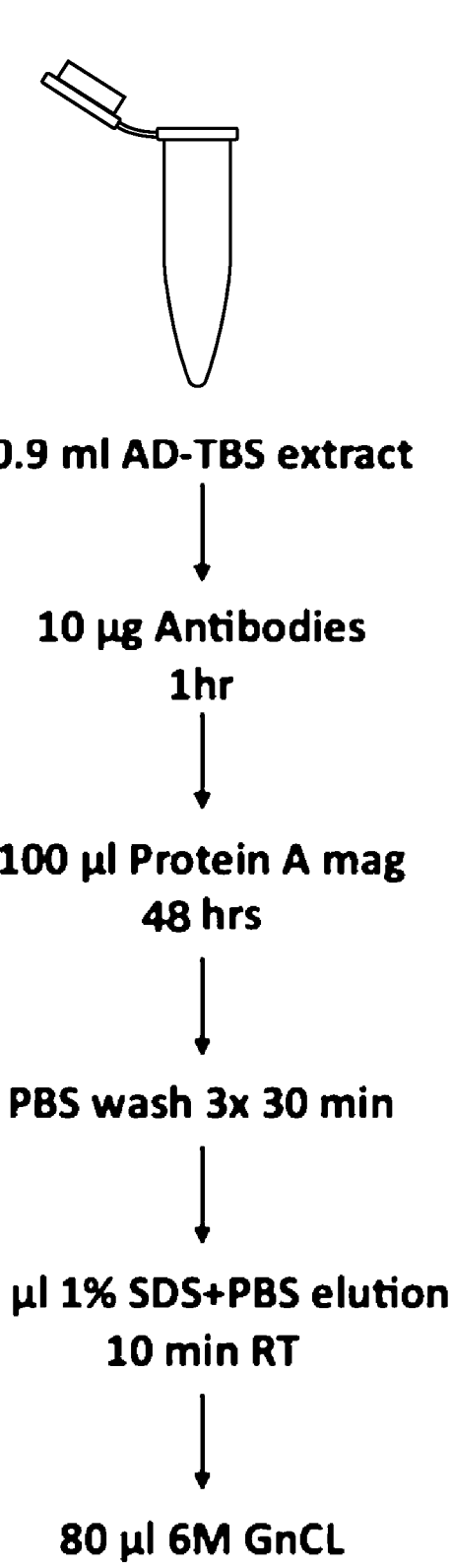
Figure 40B:
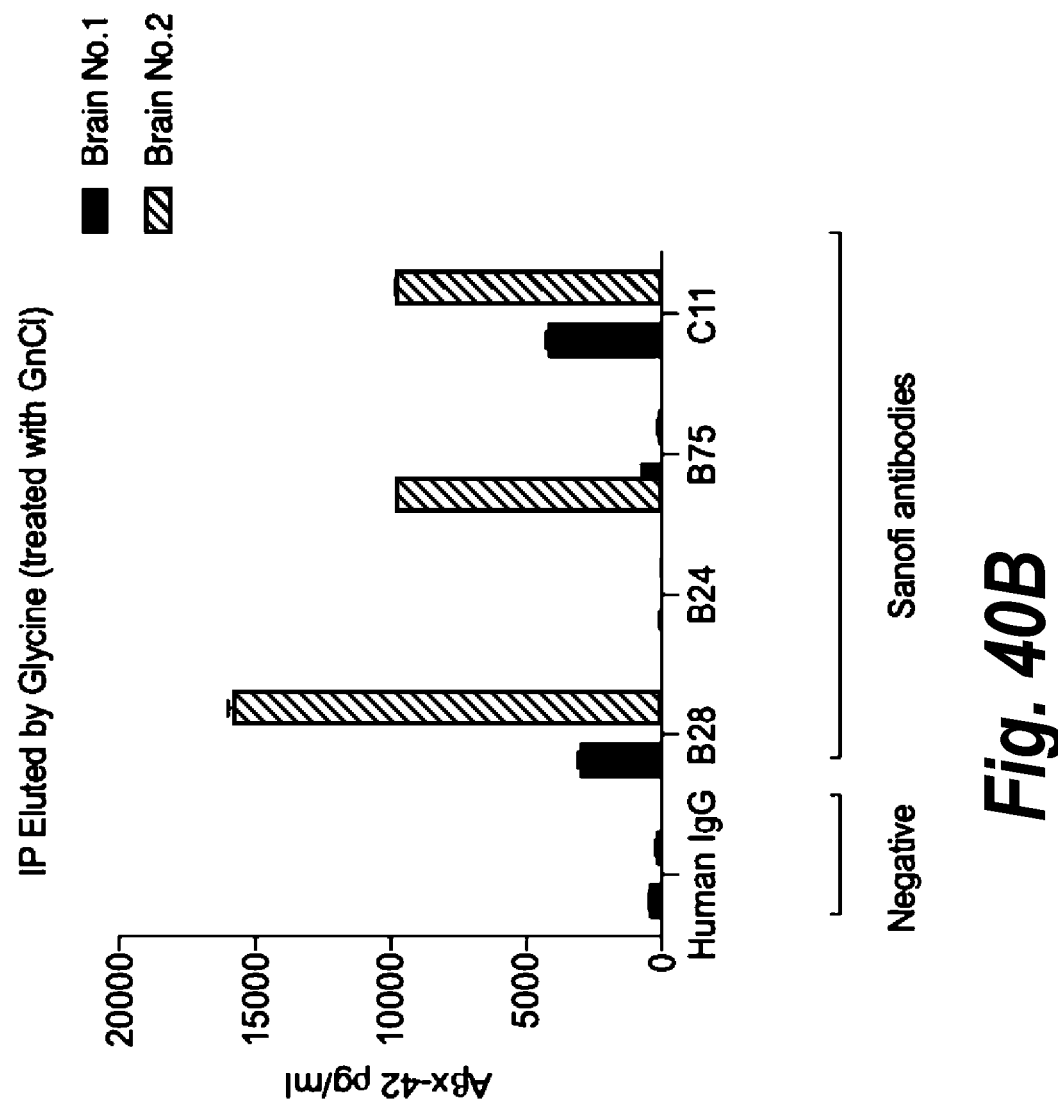
FIG. 40A-FIG. 40B depict immunoabsorption of two human brain extracts using mAbs B28, B75 and C11 on protein-A affinity columns. A) Schematically depicts the immunoabsorption work-flow of human brain extracts. B) Depicts an Aβ x-42 ELISA analysis of glycine elutions of immunoabsorptions from two brain extracts (n=2, mean±SD). Human IgG was used as negative control for immunoabsorption.
Figure 40A:
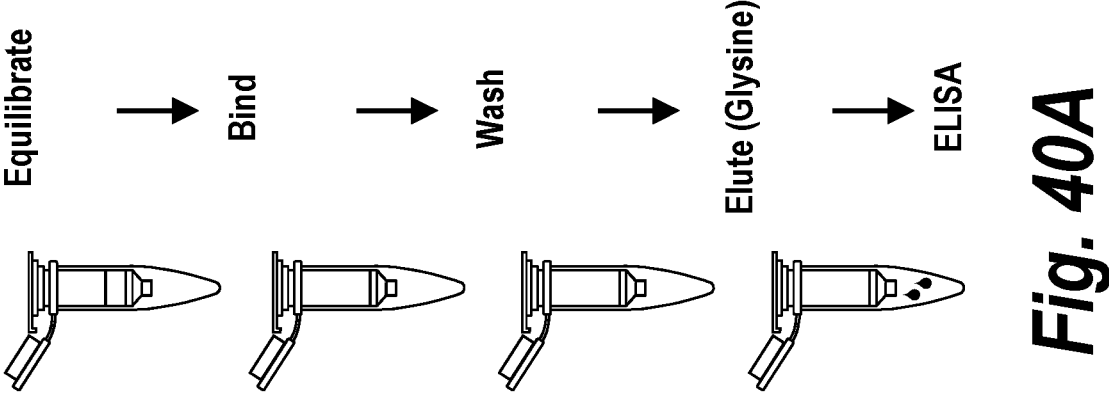

Example 7: Antibody can Capture Aβ from AD Brain But Do Not Bind Amyloid Deposits in AD Brain Sections Biochemical Data on B24, B28, B73, B75 and C11 mAbs Using Bead-Based Immunoprecipitation of Human AD Brain Extracts: B75 and C11 Immunoprecipitated Aβ x-42 Peptides from AD Brain Immunoprecipitation from human brain extracts was performed using a conventional magnetic beads method to test B24, B28, B73, B75 and C11 mAbs (FIG. 39A). Sequential elutions using 1% SDS and then 6M guanidine hydrochloride (GnCl) were measured by Aβ x-42 ELISA. Compared to the negative control (human IgG) and positive control (1C22), B28 and B73 could significantly immunoprecipitate Aβ 1-42-containing species from all four brains tested, consistent with their broad Aβ binding properties. Although to a somewhat lower extent, B75 and C11 could also significantly immunoprecipitate Aβ 1-42-containing species from two out of four brains, while B24 failed to immunoprecipitate Aβ 1-42-containing species from any brain tested (FIG. 39B). These data establish that B75 and C11 bind to Aβ 1-42-containing material in AD brain while not binding to the different synthetic Aβ preparations as described Supra. Biochemical Data Using Column Immunoabsorption of Human AD Brain Extracts: C11 and B28 Bound Aβ-Containing Species in Human AD Brain An alternative method was designed to re-test B24, B75 and C11, which showed modest affinities to Aβ-containing species by the conventional magnetic beads method. Using instead a protein-A spin column (FIG. 40A), procedures such as rotation or nutation, which would disrupt weak antibody-antigen associations, were eliminated. Through this alternative method, C11 was shown to capture as many Aβ 1-42-containing species as B28 (positive control) from two human brain extracts (FIG. 40B), while B75 was less active, underscoring that different antibody properties could be revealed by alternative techniques.

Figure 41:
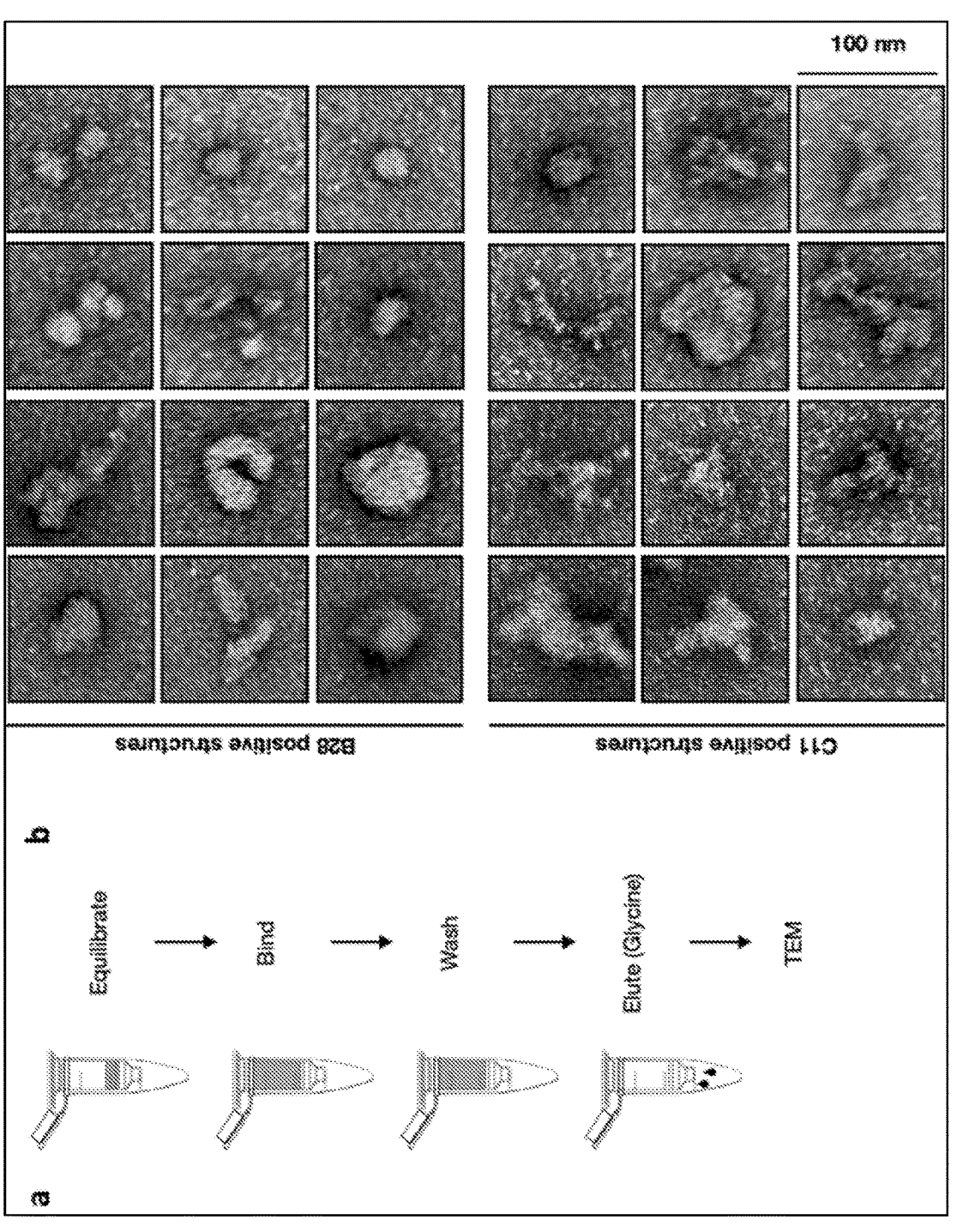
FIG. 41A-FIG. 41B depict ultrastructural analysis of immunocaptured material from human brain extracts using mAbs B28 and C11. A) Schematically depicts immunoabsorption work-flow from human brain extracts. B) depicts negative-stain transmission electron microscopy images of immunoabsorbed material from human brain extracts using B28 (top images) or C11 (bottom images).

In addition, with such spin columns, elution was performed using an acid-wash meant to destabilize the antigen-antibody interaction while having a more moderate impact on antigen structure than the SDS or guanidine wash performed in the bead immunoprecipitation example. Therefore, the potential structures of the immunocaptured materials were assessed using transmission electron microscopy (TEM) (FIG. 41A). Negatively-stained material purified by B28 and C11 was determined by TEM to be polymorphic (FIG. 41B). The B28-purified material possessed a principally globular structure with different sizes. C11 purified material possessed more diverse morphologies.

Figure 42:
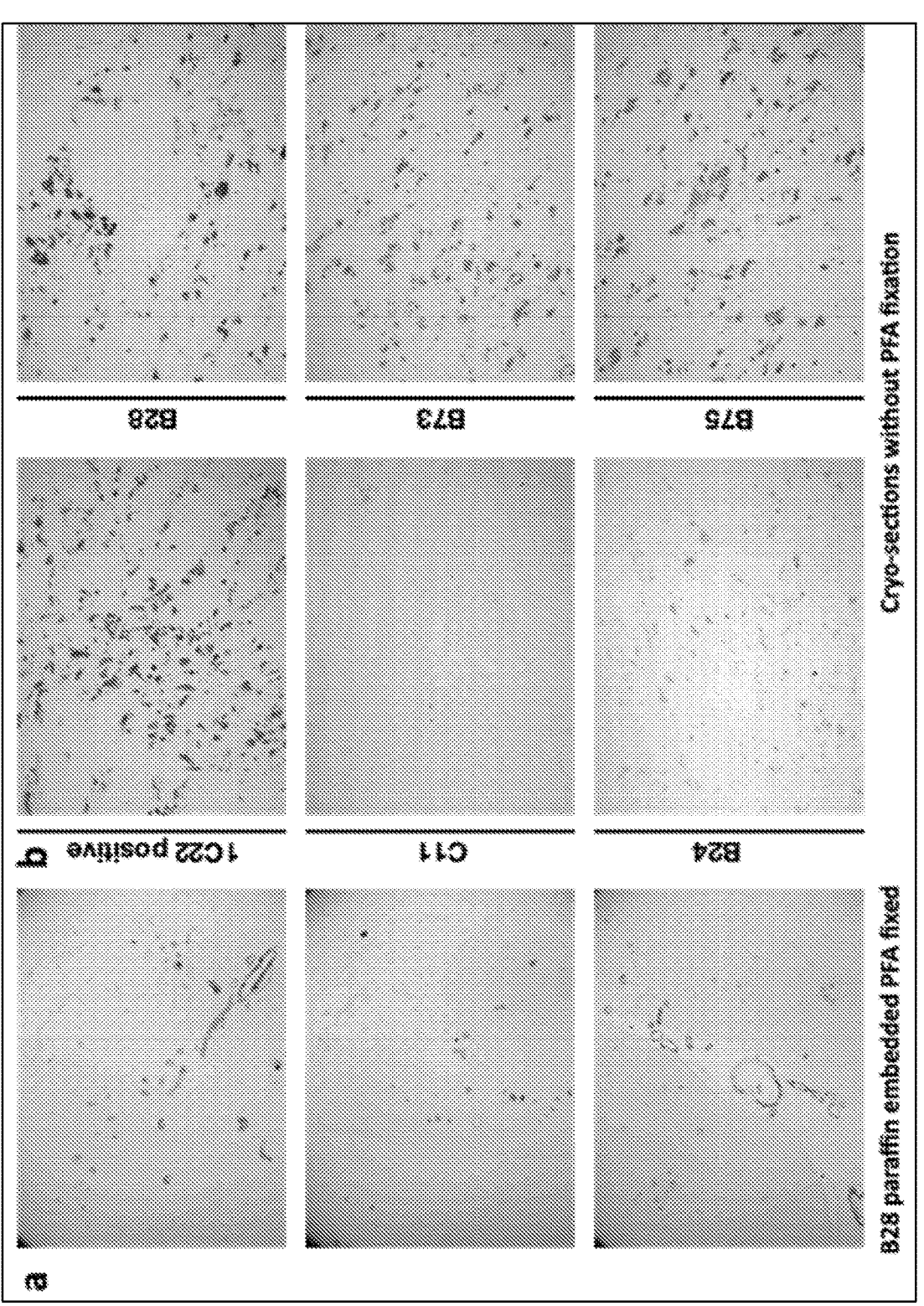
FIG. 42A-FIG. 42B depict light microscopic immunohistology of brain sections using mAbs B24, B28, B73, B75 and C11. Only B28 showed staining on paraffin-embedded PFA-fixed brain sections. A) Depicts immunohistochemistry of B28 on paraffin-embedded PFA-fixed brain sections. The other four mAbs were negative on such sections (not shown). B) depicts immunohistochemistry of mAbs B24, B28, B73, B75 and C11 on non-fixed brain cryo-sections. 1C22 was used as a positive control.

Immunohistology: C11 Did not Bind Aβ-Deposits in Human AD Brain as Assessed by Light Microscopic Immunohistology Immunohistochemistry techniques were used to compare binding patterns of the different antibodies to human AD brain sections that were fixed or fresh-frozen. Initially, all five mAbs were assessed by immunohistochemistry on the standard paraffin-embedded, PFA-fixed AD brain sections. It was determined that only B28 produced any staining, namely typical AD amyloid plaques and cerebral amyloid angiopathy (FIG. 42A). B24, B28, B73, B75 and C11 mAbs were further tested by immunohistochemistry on non-fixed brain cryo-sections, representing a likely more native conformation of Aβ assemblies in AD brain. Compared to 1C22 (the positive control), B28, B73 and B75 stained amyloid plaques strongly, B24 stained moderately, and C11 failed to stain (FIG. 42B).

Materials and Methods

Immunoprecipitation (Beads) and Immunoabsorption (Column) of Human Brain Extracts Beads: 800 μl TBS brain extracts were mixed with 10 μg mAb and protein-A magnetic beads, and were rotated at 4° C. for 12 hours. The magnetic beads were then washed with PBS 3 times, 30 minutes each at 4° C. The washed magnetic beads were sequentially eluted by 1% SDS in PBS and then 6 M guanidine hydrochloride.

Column: 800 μl TBS brain extracts were mixed with 10 μg mAb and were incubated at 4° C. for 12 hours. The mixture was added to a pre-wet protein-A column and spun at 1,000 g for 1 minute. The flow-through was added to the same column and spun at 1,000 g for 1 minute. The column was washed with PBS three times and spun at 1,000 g for 1 minute. 0.1 M glycine-HCl (pH 2.3) was added to the column and incubated for 5 minutes, followed by spinning at 1,000 g for 1 minute.

Aβ x-42 ELISA

MSD ELISA for Aβ 1-42 was performed as per an art-known method (Liu et al., 2019). Each well of an uncoated 96-well multi-array plate (Meso Scale Discovery, #L 15XA-3) was coated with 30 mL of a PBS solution containing 3 μg/mL of 266 capture antibody (Elan), and incubated at room temperature overnight. 266 epitope is in the region 13-25 of Aβ sequence. A detection antibody solution was prepared with biotinylated monoclonal antibody against the C-terminal residues of Aβ 1-42 (21F12), 100 ng/ml streptavidin sulfo-TAG (Meso Scale Discovery, #R32AD-5), and 1% BSA diluted in wash buffer. Following overnight incubation, 50 μL/well of the sample, followed by 25 μL/well of detection antibody solution, were incubated for 2 hours at room temperature with shaking at >300 rpm, washing wells with wash buffer between incubations. The plate was read and analyzed according to the manufacturer's protocol.

Transmission EM Analysis of Negatively Stained Samples

For TEM specimen preparation, 5 μL of the sample solution (glycine elution of the immunoabsorbed material (see above)) was placed onto a glow-discharged, formvar/carbon coated grid. The sample was incubated on the grid for 20 seconds at room temperature. Excess solvent was soaked away with filter paper (Whatman). The grid was washed three times with 10 μL water and stained three times with 10 μL 1% (w/v) uranyl acetate in water. The dried grids were examined in a JEM-1200EX TEM (JEOL) equipped with a AMT 2k CCD camera that was operated at 80 kV.

Immunohistochemistry

Paraffin-embedded, PFA-fixed brain sections: The rehydrated paraffin sections were treated with 0.3% $H_2O_2$ in PBS containing 0.2% Triton X-100. The sections were incubated with primary antibody at 4° C. overnight and then with biotinylated secondary antibodies for 1 hour. For visualization, the sections were treated with avidin-biotin complex (Vector) and then with 3,3'-Diaminobenzidine containing nickel ammonium sulfate.

Non-fixed brain cryo-sections: Fresh or thawed brain tissues were embedded into O.C.T. compound (Sakura) solution followed by −80° C. and −20° C. incubation each for 12 hours. Frozen blocks were sectioned at 20-30 μm intervals using a cryostat (Leica). Sections were directly mounted on adhesion microscope glass slides (Matsunami) for immunohistochemistry. The sections were then treated with 0.3% $H_2O_2$ in PBS containing 0.2% Triton X-100. The sections were incubated with primary antibody at 4° C. overnight and then with biotinylated secondary antibodies for 1 hour. For visualization, the sections were treated with avidin-biotin complex (Vector) and then with 3,3'-Diaminobenzidine containing nickel ammonium sulfate. Photomicrographs were taken with a DMi8 widefield microscope (Leica).

What is claimed is:

1. An isolated binding polypeptide that specifically binds soluble amyloid beta (Aβ), wherein the binding polypeptide comprises three heavy chain complementary determining region (HCDR) sequences and three light chain complementary determining region (LCDR) sequences,
   wherein the three HCDR sequences and the three LCDR sequences are selected from the group consisting of
   (i) HCDR sequences comprising SEQ ID NOs: 20, 21 and 22, and LCDR sequences comprising SEQ ID NOs: 17, 18 and 19;
   (ii) HCDR sequences comprising SEQ ID NOs: 44, 45 and 46, and LCDR sequences comprising SEQ ID NOs: 41, 42 and 43;
   (iii) HCDR sequences comprising SEQ ID NOs: 26, 27 and 28, and LCDR sequences comprising SEQ ID NOs: 23, 24 and 25;
   (iv) HCDR sequences comprising SEQ ID NOs: 50, 51 and 52, and LCDR sequences comprising SEQ ID NOs: 47, 48 and 49;
   (v) HCDR sequences comprising SEQ ID NOs: 62, 63 and 64, and LCDR sequences comprising SEQ ID NOs: 59, 60 and 61;
   (vi) HCDR sequences comprising SEQ ID NOs: 32, 33 and 34, and LCDR sequences comprising SEQ ID NOs: 29, 30 and 31;
   (vii) HCDR sequences comprising SEQ ID NOs: 38, 39 and 40, and LCDR sequences comprising SEQ ID NOs: 35, 36 and 37; and
   (viii) HCDR sequences comprising SEQ ID NOs: 56, 57 and 58, and LCDR sequences comprising SEQ ID NOs: 53, 54 and 55.

2. The binding polypeptide of claim 1, comprising an antibody or an antigen-binding fragment thereof, optionally wherein the antibody or antigen-binding fragment thereof is human.

3. The human antibody of claim 2, wherein the antibody or antigen-binding fragment thereof is IgG1.

4. The binding polypeptide of claim 1, wherein the soluble Aβ is synaptotoxic or has a molecular weight of between about 20 kD and about 100 kD or both.

5. The binding polypeptide of claim 1, wherein the binding polypeptide specifically binds soluble Aβ derived from the brain of a subject having Alzheimer's disease or neutralizes Aβ synaptotoxicity.

6. The binding polypeptide of claim 5, wherein binding is immunoabsorption.

7. The binding polypeptide of claim 5, wherein the soluble Aβ is present in one or more soluble fractions obtained from brain derived from a subject having Alzheimer's disease.

8. The binding polypeptide of claim 5, wherein the binding polypeptide neutralizes synaptotoxicity of the soluble Aβ of brain derived from a subject having Alzheimer's disease.

9. The binding polypeptide of claim 1, wherein the binding polypeptide does not specifically bind monomeric Aβ, protofibrillar Aβ or fibrillar Aβ or a protein aggregate or an amyloid plaque present in brain derived from a subject having Alzheimer's disease.

10. A pharmaceutical composition comprising the binding polypeptide of claim 1, and a pharmaceutically acceptable carrier.

11. A method of treating Alzheimer's disease in a subject comprising administering to the subject an effective amount of the pharmaceutical composition of claim 10.

12. An isolated polynucleotide encoding the binding polypeptide of claim 1.

13. A host cell comprising the polynucleotide of claim 12.

14. A vector comprising the polynucleotide of claim 12.

15. A host cell comprising the vector of claim 14.

16. An isolated binding polypeptide that specifically binds soluble amyloid beta (Aβ), wherein the binding polypeptide comprises a heavy chain variable region (HCVR)/light chain variable region (LCVR) sequence pair selected from the group consisting of: SEQ ID NOs: 2 and 1; SEQ ID NOs: 10 and 9; SEQ ID NOs: 4 and 3; SEQ ID NOs: 12 and 11; and SEQ ID NOs: 16 and 15.

17. An isolated binding polypeptide that specifically binds soluble amyloid beta (Aβ) comprising three heavy chain complementary determining regions (HCDRs) and three light chain complementary determining regions (LCDRs), wherein the three HCDR and LCDR are selected from the group consisting of:

(i) HCDRs comprising SEQ ID NOs: 20, 21 and 22, and LCDRs comprising SEQ ID NOs: 17, 18 and 19;

(ii) HCDRs comprising SEQ ID NOs: 44, 45 and 46, and LCDRs comprising SEQ ID NOs: 41, 42 and 43;

(iii) HCDRs comprising SEQ ID NOs: 26, 27 and 28, and LCDRs comprising SEQ ID NOs: 23, 24 and 25;

(iv) HCDRs comprising SEQ ID NOs: 50, 51 and 52, and LCDRs comprising SEQ ID NOs: 47, 48 and 49;

(v) HCDRs comprising SEQ ID NOs: 62, 63 and 64, and LCDR comprising SEQ ID NOs: 59, 60 and 61.

\* \* \* \* \*